United States Patent
Schafer et al.

(10) Patent No.: US 12,064,437 B2
(45) Date of Patent: Aug. 20, 2024

(54) METHODS FOR TREATING SYSTEMIC LUPUS ERYTHEMATOSUS AND THE USE OF BIOMARKERS AS A PREDICTOR OF CLINICAL SENSITIVITY TO THERAPIES

(71) Applicant: CELGENE CORPORATION, Summit, NJ (US)

(72) Inventors: Peter H. Schafer, Belle Mead, NJ (US); Shaojun Tang, Summit, NJ (US)

(73) Assignee: CELGENE CORPORATION, Summit, NJ (US)

( * ) Notice: Subject to any disclaimer, the term of this patent is extended or adjusted under 35 U.S.C. 154(b) by 104 days.

(21) Appl. No.: 17/490,778

(22) Filed: Sep. 30, 2021

(65) Prior Publication Data

US 2022/0160720 A1   May 26, 2022

Related U.S. Application Data

(60) Provisional application No. 63/087,008, filed on Oct. 2, 2020.

(51) Int. Cl.
*A61K 31/5377*  (2006.01)
*A61P 37/00*  (2006.01)
*C12Q 1/6883*  (2018.01)

(52) U.S. Cl.
CPC .......... *A61K 31/5377* (2013.01); *A61P 37/00* (2018.01); *C12Q 1/6883* (2013.01); *C12Q 2600/158* (2013.01)

(58) Field of Classification Search
CPC .................................................. A61K 31/5377
See application file for complete search history.

(56) References Cited

U.S. PATENT DOCUMENTS

2014/0343058 A1* 11/2014 Schafer ................ C07D 401/04
                                                        514/235.2
2020/0231567 A1    7/2020 Man et al.

OTHER PUBLICATIONS

Bengtsson et al., 2012, "Pharmacokinetics, tolerability, and preliminary efficacy of paquinimod (ABR-215757), a new quinoline-3-carboxamide derivative: studies in lupus-prone mice and a multi-center, randomized, double-blind, placebo-controlled, repeat-dose, dose-ranging study in patients with systemic lupus erythematosus," Arthritis. Rheum., 64(5):1579-1588.

International Searching Authority, International Search Report and Written Opinion for International Patent Application No. PCT/US2021/052771 mailed Mar. 9, 2022 (16 pages).

* cited by examiner

*Primary Examiner* — Paul V Ward
(74) *Attorney, Agent, or Firm* — JONES DAY

(57) ABSTRACT

A method of determining a dose of a treatment compound for treating a subject having systemic lupus erythematosus (SLE), comprising obtaining a sample from the subject and measuring the gene expression level of IKZF3 and/or the gene expression levels of IFI27, IFI44, IFI44L, and RSAD2 in the sample.

18 Claims, 4 Drawing Sheets

METHODS FOR TREATING SYSTEMIC LUPUS ERYTHEMATOSUS AND THE USE OF BIOMARKERS AS A PREDICTOR OF CLINICAL SENSITIVITY TO THERAPIES

CROSS-REFERENCE TO RELATED APPLICATIONS

This application claims the benefit of U.S. Provisional Patent Application No. 63/087,008, filed Oct. 2, 2020, which is incorporated by reference herein in its entirety

1. FIELD

Provided herein, in some embodiments, are methods of using certain biomarkers in predicting and monitoring clinical sensitivity and therapeutic response to or determining dose of Compound I or a pharmaceutically acceptable salt, solvate, hydrate, stereoisomer, tautomer or racemic mixtures thereof, including (S)-3-[4-(4-morpholin-4-ylmethylbenzyloxy)-1-oxo-1,3-dihydro-isoindo-2-yl]piperidine-2,6-dione, in patients having various diseases and disorders, such as systemic lupus erythematosus (SLE). Further provided are kits for carrying out the methods. Also provided herein, in certain embodiments, are methods of determining the efficacy of a compound in treating diseases.

2. BACKGROUND

Systemic lupus erythematosus (SLE) is a multi-organ autoimmune disease of unknown etiology that has many clinical manifestations. Almost any organ can be involved, but the most common manifestations are cutaneous, musculoskeletal and renal. SLE typically affects young women of childbearing potential between the ages of 15 to 44. The prevalence of SLE is 300,000 patients in the United States and 4 million patients worldwide, with an annual incidence of 15,000 in the United States alone.

The pathogenesis of SLE likely involves an array of components associated with both genetic and environmental factors. Disease susceptibility is influenced by genes related to immune response and the major histocompatibility complex class I and II genes. Additional susceptibility stems from interactions between the hormonal environment and the hypothalamo-pituitaryadrenalaxis. In addition, the development of SLE is associated with a defective immune response which affects apoptotic cell clearance and immune complexes. The loss of immune tolerance, excess T cell help, defective B cell suppression, and the shifting of T helper 1 (Th1) to Th2 and Th17 immune responses leads to B cell hyperactivity and the production of pathogenic antibodies. External factors such as chemicals, drugs, ultraviolet light, diet and viruses also contribute to the onset of disease.

As SLE is a waxing and waning disease, it is often controlled with NSAIDs or low potency immunosuppression drugs (antimalarials and low dose corticosteroids) for milder symptomology (muscoskeletal manifestation, cutaneous manifestation and serositis). More prolonged and potent use of corticosteroids, as well as non-biologic disease modifying anti-rheumatic drugs (DMARDs), are standard treatments which are also available to treat those patients who exhibit major organ involvement. In conjunction with standard therapy, biological DMARD therapies exist to augment treatment for those patients with more extensive disease. Belimumab, a monoclonal antibody and B-lymphocyte stimulator-specific inhibitor, has recently been approved for use in conjunction with corticosteroids and other standard therapies for autoantibody-positive SLE. In addition, Rituximab, a B-cell depleter, is often used off-label as rescue medication for patients unresponsive to standard treatment.

However, there still remains a need for prophylactic or therapeutic drugs that can be used to treat or prevent SLE. A number of studies have been conducted with the aim of providing compounds that can safely and effectively be used to treat SLE. Clinical efficacy of these compounds cannot easily be correctly predicted, as it can only be measured in terms of patient response, which usually requires a minimum of several months of treatment. In view of the deficiencies of the conventional methods, there is a need to develop efficient, sensitive, and accurate methods to detect, quantify, and characterize the pharmacodynamic activity of certain compounds. The present invention satisfies these and other needs.

3. SUMMARY OF THE INVENTION

In one aspect, provided herein is a method of determining a dose of a treatment compound for treating a subject having systemic lupus erythematosus (SLE), comprising (a) obtaining a sample from the subject; (b) measuring the gene expression level of IKZF3 in the sample; and (c) determining the dose of the treatment compound to be 0.45 mg or higher per day if a score calculated based on the gene expression level of IKZF3 in the sample is higher than a reference level, wherein the treatment compound is a compound of Formula I:

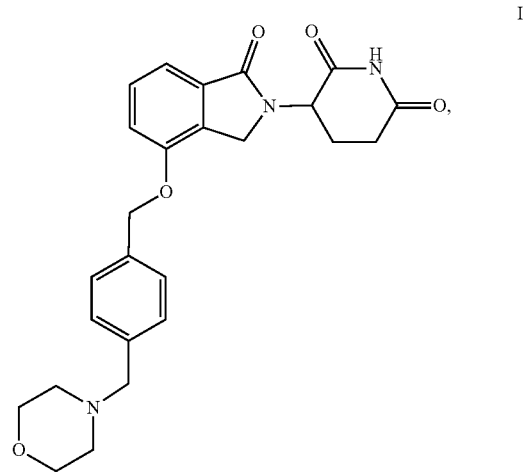 [SMILES: O=C1CCC(N2Cc3c(OCc4ccc(CN5CCOCC5)cc4)cccc3C2=O)C(=O)N1]

or a pharmaceutically acceptable salt, solvate, hydrate, stereoisomer, tautomer or racemic mixture thereof.

In some embodiments, the score is Log 2 of the gene expression level of IKZF3 relative to a reference gene in the sample, or wherein the score is Log 2 of the gene expression level of IKZF3 relative to an average gene expression level of two or more reference genes in the sample.

In some embodiments, the method comprises determining the dose of the treatment compound to be 0.45 mg or higher per day if a score is higher than −0.49.

In some embodiments, the reference gene is selected from a group consisting of TFRC, ACTB, GAPDH, and combinations thereof.

In some embodiments, the method comprises determining the dose of the treatment compound to be about 0.45 mg per day if the score is higher than the reference level. In some embodiments, the method comprises determining the dose of the treatment compound to be about 0.5 mg per day if the score is higher than the reference level. In some embodiments, the method comprises determining the dose of the treatment compound to be about 0.6 mg per day if the score is higher than the reference level. In other embodiments, the method comprises determining the dose of the treatment compound to be about 0.7 mg per day if the score is higher than the reference level.

In some embodiments, the method further comprises administering the dose of 0.45 mg or higher per day of the treatment compound to the subject.

In another aspect, provided herein is a method of treating a subject having systemic lupus erythematosus (SLE), comprising administering to the subject with a dose of a treatment compound of 0.45 mg or higher per day, wherein a score calculated based on the gene expression level of IKZF3 in a sample from the subject is higher than a reference level; and wherein the treatment compound is a compound of Formula I:

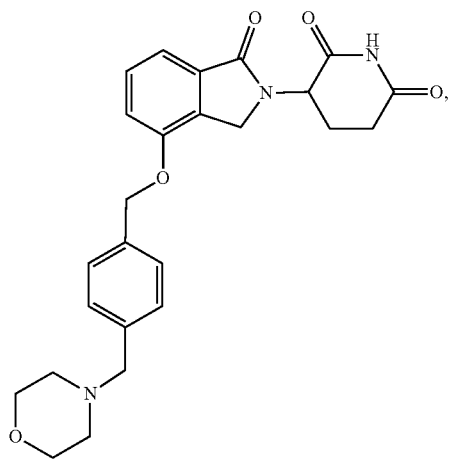

or a pharmaceutically acceptable salt, solvate, hydrate, stereoisomer, tautomer or racemic mixture thereof.

In some embodiments, the score is Log 2 of the gene expression level of IKZF3 relative to a reference gene, or wherein the score is Log 2 of the gene expression level of IKZF3 relative to an average gene expression level of two or more reference genes. In some embodiments, the reference level is −0.49. In some embodiments, the reference gene is selected from a group consisting of TFRC, ACTB, GAPDH, and combinations thereof.

In some embodiments, the dose of the treatment compound is about 0.45 mg per day. In some embodiments, the dose of the treatment compound is about 0.5 mg per day. In some embodiments, the dose of the treatment compound is about 0.6 mg per day. In other embodiments, the dose of the treatment compound is about 0.7 mg per day.

In another aspect, provided herein is a method of determining a dose of a treatment compound for treating a subject having systemic lupus erythematosus (SLE), comprising (a) obtaining a sample from the subject; (b) measuring the gene expression levels of IFI27, IFI44, IFI44L, and RSAD2 in the sample; and (c) determining the dose of the treatment compound to be 0.45 mg or higher per day or to be 0.15 mg or lower per day if a score calculated based on the gene expression levels of IFI27, IFI44, IFI44L, and RSAD2 is higher than a reference level, wherein the treatment compound is a compound of Formula I:

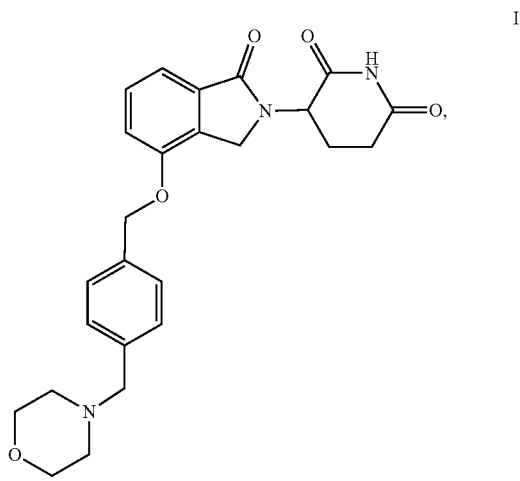 [SMILES: O=C1CCC(N2Cc3c(OCc4ccc(CN5CCOCC5)cc4)cccc3C2=O)C(=O)N1]

or a pharmaceutically acceptable salt, solvate, hydrate, stereoisomer, tautomer or racemic mixture thereof.

In some embodiments, the score is Log 2 of an average of the gene expression levels of IFI27, IFI44, IFI44L, and RSAD2 relative to a reference gene in the sample, or wherein the score is Log 2 of an average of the gene expression levels of IFI27, IFI44, IFI44L, and RSAD2 relative to an average of two or more reference genes in the sample.

In some embodiments, the method comprises determining the dose of the treatment compound to be 0.45 mg or higher per day or to be 0.15 mg or lower per day if a score is higher than −1.38.

In some embodiments, the reference gene is selected from a group consisting of TFRC, ACTB, GAPDH, and combinations thereof.

In some embodiments, the method comprises determining the dose of the treatment compound to be about 0.45 mg per day if the score is higher than the reference level. In some embodiments, the method comprises determining the dose of the treatment compound to be about 0.5 mg per day if the score is higher than the reference level. In other embodiments, the method comprises determining the dose of the treatment compound to be about 0.6 mg per day if the score is higher than the reference level. In other embodiments, the method comprises determining the dose of the treatment compound to be about 0.7 mg per day if the score is higher than the reference level. In some embodiments, the method comprises determining the dose of the treatment compound to be about 0.15 mg per day if the score is higher than the reference level. In other embodiments, the method comprises determining the dose of the treatment compound to be about 0.1 mg per day if the score is higher than the reference level. In other embodiments, the method comprises determining the dose of the treatment compound to be about 0.75 mg per day if the score is higher than the reference level. In some embodiments, the treatment compound in the daily dose described above is administered once a day. In some embodiments, the treatment compound in the daily dose described above is administered every other day. In some embodiments, the treatment compound in the daily dose described above is administered every three days. In some embodiments, the treatment compound in the daily dose described above is administered once a week. For example, in some embodiments, the dose of the treatment compound is about 0.15 mg every other day, about 0.15 mg every three days, or about 0.15 mg once a week.

In some embodiments, the method comprises administering the dose of 0.45 mg or higher per day or 0.15 mg or lower per day of the treatment compound to the subject.

In yet another aspect, provided herein is a method of treating a subject having systemic lupus erythematosus (SLE), comprising administering to the subject with a dose of a treatment compound of 0.45 mg or higher per day or 0.15 mg or lower per day, wherein a score calculated based on the gene expression levels of IFI27, IFI44, IFI44L, and RSAD2 in a sample from the subject is higher than a reference level; and wherein the treatment compound is a compound of Formula I:

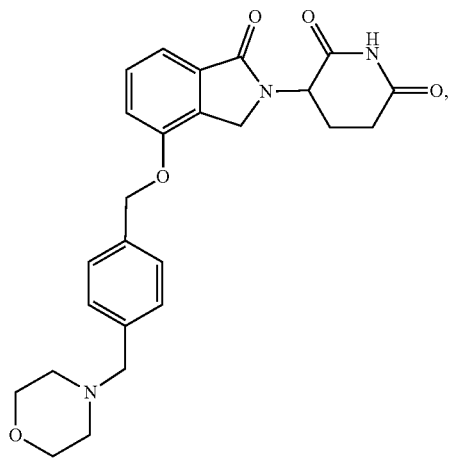

or a pharmaceutically acceptable salt, solvate, hydrate, stereoisomer, tautomer or racemic mixture thereof.

In some embodiments, the score is Log 2 of an average of the gene expression levels of IFI27, IFI44, IFI44L, and RSAD2 relative to a reference gene in the sample, or wherein the score is Log 2 of an average of the gene expression levels of IFI27, IFI44, IFI44L, and RSAD2 relative to an average of two or more reference genes in the sample. In some embodiments, the score is higher than −1.38. In some embodiments, the reference gene is selected from a group consisting of TFRC, ACTB, GAPDH, and combinations thereof.

In some embodiments, the dose of the treatment compound is about 0.45 mg per day. In some embodiments, the dose of the treatment compound is about 0.5 mg per day. In some embodiments, the dose of the treatment compound is about 0.6 mg per day. In other embodiments, the dose of the treatment compound is about 0.7 mg per day. In some embodiments, the dose of the treatment compound is about 0.15 mg per day. In other embodiments, the dose of the treatment compound is about 0.1 mg per day. In yet other embodiments, the dose of the treatment compound is about 0.075 mg per day. In some embodiments, the treatment compound in the daily dose described above is administered once a day. In some embodiments, the treatment compound in the daily dose described above is administered every other day. In some embodiments, the treatment compound in the daily dose described above is administered every three days.

In some embodiments, the treatment compound in the daily dose described above is administered once a week. For example, in some embodiments, the dose of the treatment compound is about 0.15 mg every other day, about 0.15 mg every three days, or about 0.15 mg once a week.

In yet another aspect, provided herein is a method of identifying a subject having systemic lupus erythematosus (SLE) who is likely to be responsive to a treatment compound or predicting the responsiveness of a subject having SLE to a treatment compound, comprising (a) obtaining a sample from the subject; (b) determining (i) the gene expression level of IKZF3 or (ii) the gene expression levels of IFI27, IFI44, IFI44L, and RSAD2 in the sample; and (c) diagnosing the subject as being likely to be responsive to the treatment compound if a score calculated based on the gene expression level of IKZF3 or the gene expression levels of IFI27, IFI44, IFI44L, and RSAD2 is higher than a reference level, wherein the treatment compound is a compound of Formula I:

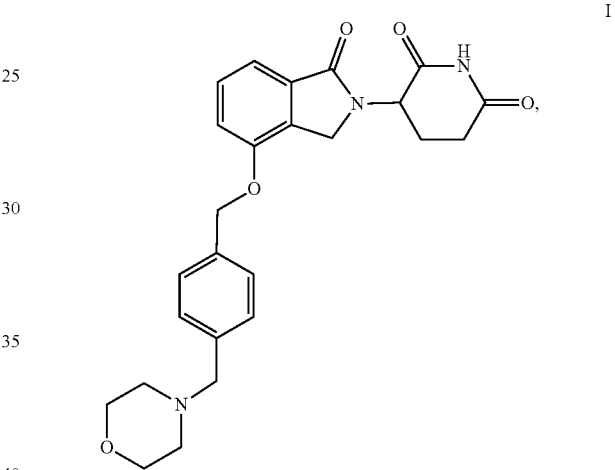

or a pharmaceutically acceptable salt, solvate, hydrate, stereoisomer, tautomer or racemic mixture thereof.

In some embodiments, the method comprises determining the gene expression level of IKZF3 and diagnosing the subject as being likely to be responsive to the treatment compound if the score calculated based on the gene expression level of IKZF3 is higher than the reference level. In some embodiments, the score is Log 2 of the gene expression level of IKZF3 relative to a reference gene in the sample, or wherein the score is Log 2 of the gene expression level of IKZF3 relative to an average gene expression level of two or more reference genes in the sample. In some embodiments, the reference level is −0.49. In some embodiments, the reference gene is selected from a group consisting of TFRC, ACTB, GAPDH, and combinations thereof.

In other embodiments, the method comprises determining the gene expression levels of IFI27, IFI44, IFI44L, and RSAD2 and diagnosing the subject as being likely to be responsive to the treatment compound if the score calculated based on the gene expression levels of IFI27, IFI44, IFI44L, and RSAD2 is higher than the reference level. In some embodiments, the score is Log 2 of an average of the gene expression levels of IFI27, IFI44, IFI44L, and RSAD2 relative to a reference gene in the sample, or wherein the score is Log 2 of an average of the gene expression levels of IFI27, IFI44, IFI44L, and RSAD2 relative to an average of two or more reference genes in the sample. In some embodiments, the reference level is −1.38. In some embodiments, the reference gene is selected from a group consisting of TFRC, ACTB, GAPDH, and combinations thereof.

In some embodiments, the method further comprises administering an effective amount of the treatment compound to the subject determined to be likely to be responsive to the treatment compound.

In yet another aspect, provided herein is a method of treating a subject having systemic lupus erythematosus (SLE) comprising administering an effective amount of a treatment compound to the subject, wherein the subject has been determined to be likely to be responsive to the treatment compound according to the method provided herein, wherein the treatment compound is a compound of Formula I:

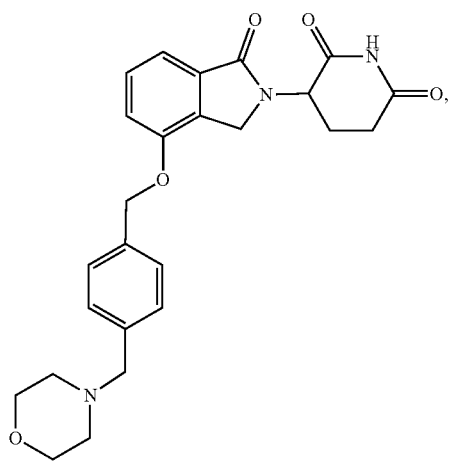

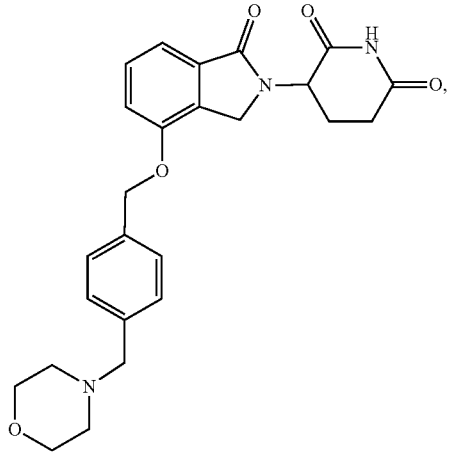

or a pharmaceutically acceptable salt, solvate, hydrate, stereoisomer, tautomer or racemic mixture thereof.

In yet another aspect, provided herein is a method of determining a dose of a treatment compound for treating a subject having systemic lupus erythematosus (SLE), comprising (a) obtaining a sample from the subject; (b) measuring (i) the gene expression level of IKZF3 and (ii) the gene expression levels of IFI27, IFI44, IFI44L, and RSAD2 in the sample; (c) determining a first score based on the gene expression level of IKZF3 and comparing the first score with a first reference level; (d) determining a second score based on the gene expression levels of IFI27, IFI44, IFI44L, and RSAD2 and comparing the second score with a second reference level; and (e) determining the dose of the treatment compound based on the first score and the second score, wherein the treatment compound is a compound of Formula I:

or a pharmaceutically acceptable salt, solvate, hydrate, stereoisomer, tautomer or racemic mixture thereof.

In some embodiments, the first score is Log 2 of the gene expression level of IKZF3 relative to a reference gene in the sample, or wherein the first score is Log 2 of the gene expression level of IKZF3 relative to an average gene expression level of two or more reference genes in the sample. In some embodiments, the first reference level is −0.49. In some embodiments, the reference gene is selected from a group consisting of TFRC, ACTB, GAPDH, and combinations thereof.

In some embodiments, the second score is Log 2 of an average of the gene expression levels of IFI27, IFI44, IFI44L, and RSAD2 relative to a reference gene in the sample, or wherein the second score is Log 2 of an average of the gene expression levels of IFI27, IFI44, IFI44L, and RSAD2 relative to an average of two or more reference genes in the sample. In some embodiments, the second reference level is −1.38. In some embodiments, the reference gene is selected from a group consisting of TFRC, ACTB, GAPDH, and combinations thereof.

In some embodiments, when the first score is higher than the first reference level and the second score is higher than the second reference level, the dose of the treatment compound is determined to be 0.45 mg or higher per day or to be 0.15 mg or lower per day.

In other embodiments, when the first score is higher than the first reference level and the second score is lower than the second reference level, the dose of the treatment compound is determined to be 0.15 mg or lower per day.

In yet other embodiments, when the first score is lower than the first reference level and the second score is higher than the second reference level, the dose of the treatment compound is determined to be 0.45 mg or higher per day.

In yet another aspect, provided herein is a method of treating a subject having systemic lupus erythematosus (SLE), comprising administering to the subject with a dose of a treatment compound, wherein the dose of the treatment compound is determined according to the method provided herein; and wherein the treatment compound is a compound of Formula I:

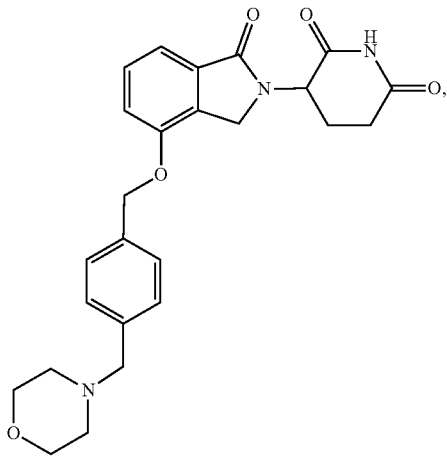

or a pharmaceutically acceptable salt, solvate, hydrate, stereoisomer, tautomer or racemic mixture thereof.

In some embodiments, the gene expression level is measured by determining the protein level. In other embodiments, the gene expression level is measured by determining the mRNA level. In yet other embodiments, the gene expression level is measured by determining the cDNA level.

In some embodiments, the compound is (S)-3-[4-(4-morpholin-4-ylmethylbenzyloxy)-1-oxo-1,3-dihydro-isoindo-2-yl]piperidine-2,6-dione or a pharmaceutically acceptable salt, solid form, solvate, hydrate, tautomer, stereoisomer or racemate thereof. In some embodiments, the compound is (S)-3-[4-(4-morpholin-4-ylmethylbenzyloxy)-1-oxo-1,3-dihydro-isoindo-2-yl]piperidine-2,6-dione. In yet other embodiments, the compound is (S)-3-[4-(4-morpholin-4-ylmethylbenzyloxy)-1-oxo-1,3-dihydro-isoindo-2-yl]piperidine-2,6-dione hydrochloride.

In yet another aspect, provided herein is a method of identifying a subject having systemic lupus erythematosus (SLE) who is likely to be responsive to a treatment compound or predicting the responsiveness of a subject having SLE to a treatment compound, comprising (a) obtaining a sample from the subject; (b) determining the presence of IKZF1 single nucleotide polymorphism (SNP) rs4917014 in the sample; and (c) diagnosing the subject as being likely to be responsive to the treatment compound if at least one copy of SNP rs4917014 is detected, wherein the treatment compound is a compound of Formula I:

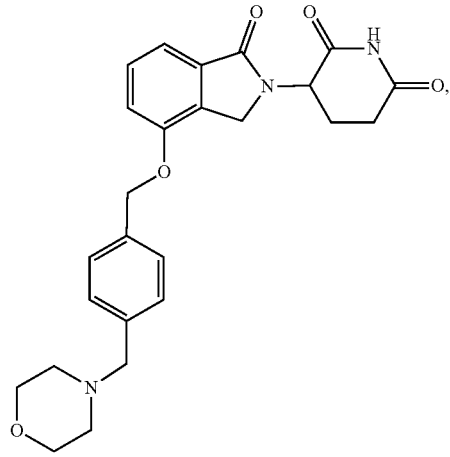

or a pharmaceutically acceptable salt, solvate, hydrate, stereoisomer, tautomer or racemic mixture thereof.

In some embodiments, the method further comprises administering an effective amount of the treatment compound to the subject determined to be likely to be responsive to the treatment compound.

In yet another aspect, provided herein is a method of treating a subject having systemic lupus erythematosus (SLE) comprising administering an effective amount of a treatment compound to the subject, wherein the subject has been determined to be likely to be responsive to the treatment compound according to the method provided herein, wherein the treatment compound is a compound of Formula I:

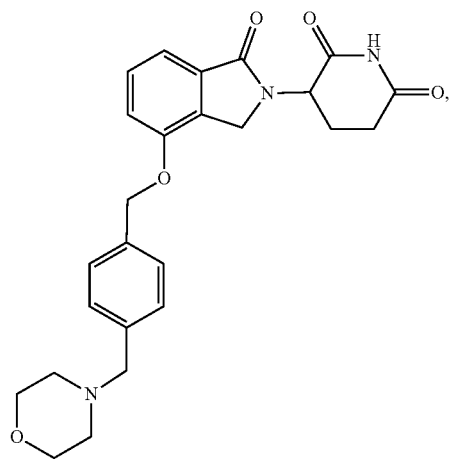

or a pharmaceutically acceptable salt, solvate, hydrate, stereoisomer, tautomer or racemic mixture thereof.

In some embodiments, the compound is (S)-3-[4-(4-morpholin-4-ylmethylbenzyloxy)-1-oxo-1,3-dihydro-isoindo-2-yl]piperidine-2,6-dione or a pharmaceutically acceptable salt, solid form, solvate, hydrate, tautomer, stereoisomer or racemate thereof. In some embodiments, the compound is (S)-3-[4-(4-morpholin-4-ylmethylbenzyloxy)-1-oxo-1,3-dihydro-isoindo-2-yl]piperidine-2,6-dione. In yet other embodiments, the compound is (S)-3-[4-(4-morpholin-4-ylmethylbenzyloxy)-1-oxo-1,3-dihydro-isoindo-2-yl]piperidine-2,6-dione hydrochloride.

In some embodiments, provided herein is a method of treating a subject having systemic lupus erythematosus (SLE), comprising administering to the subject with a dose of a treatment compound of 0.45 mg or higher per day or 0.15 mg or lower per day, wherein the subject has a high type 1 IFN expression and/or gene signature; and wherein the treatment compound is a compound of Formula I:

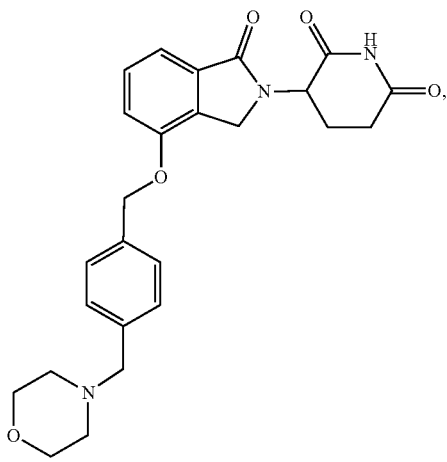

I or a pharmaceutically acceptable salt, solvate, hydrate, stereoisomer, tautomer or racemic mixture thereof.

In some embodiments, the subject is determined to have the high type 1 IFN expression and/or gene signature if a score calculated based on the gene expression levels of IFI27, IFI44, IFI44L, and RSAD2 in a sample from the subject is higher than a reference level. In some embodiments, the score is Log 2 of an average of the gene expression levels of IFI27, IFI44, IFI44L, and RSAD2 relative to a reference gene in the sample, or wherein the score is Log 2 of an average of the gene expression levels of IFI27, IFI44, IFI44L, and RSAD2 relative to an average of two or more reference genes in the sample. In some embodiments, the score is higher than −1.38. In some embodiments, the reference gene is selected from a group consisting of TFRC, ACTB, GAPDH, and combinations thereof. In some embodiments, the dose of the treatment compound is about 0.45 mg per day. In some embodiments, the dose of the treatment compound is about 0.5 mg per day. In some embodiments, the dose of the treatment compound is about 0.6 mg per day. In some embodiments, the dose of the treatment compound is about 0.7 mg per day. In some embodiments, the dose of the treatment compound is about 0.15 mg per day. In some embodiments, the dose of the treatment compound is about 0.1 mg per day. In some embodiments, the dose of the treatment compound is about 0.075 mg per day. In some embodiments, the dose of the treatment compound is about 0.15 mg every other day. In some embodiments, the dose of the treatment compound is about 0.15 mg every three days. In some embodiments, the dose of the treatment compound is about 0.15 mg once a week.

4. BRIEF DESCRIPTION OF THE FIGURES

5. DETAILED DESCRIPTION OF THE INVENTION

Figure 1:
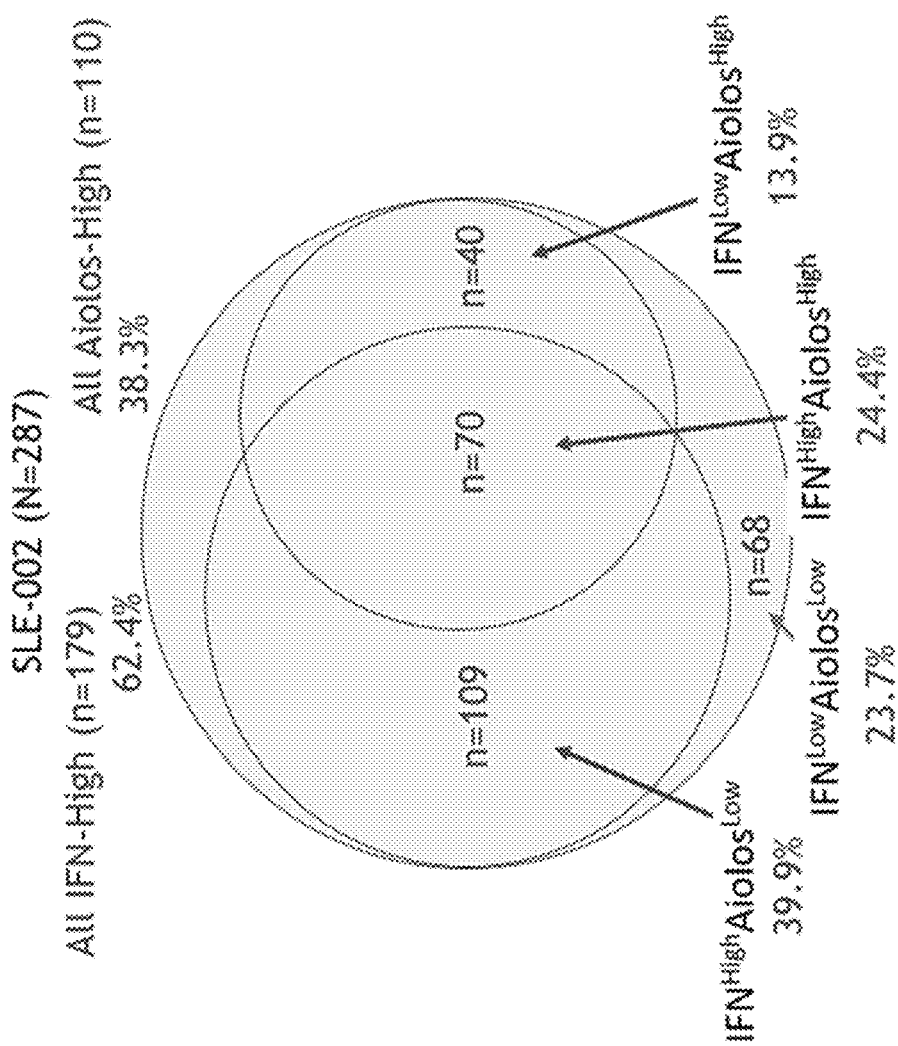
FIG. 1 shows distribution and overlap of the type 1 IFN-high and Aiolos-High patient subsets in the studies described in Example 2.

The methods provided herein are based, in part, on the discovery that the levels of certain molecules (e.g., mRNAs, cDNAs, or proteins) in a biological sample can be used to predict responsiveness of a subject having or suspected to have systemic lupus erythematosus (SLE) to a treatment compound (e.g., Compound I or a pharmaceutically acceptable salt, solvate, hydrate, stereoisomer, tautomer or racemic mixtures thereof, including (S)-3-[4-(4-morpholin-4-ylmethylbenzyloxy)-1-oxo-1,3-dihydro-isoindo-2-yl]piperidine-2,6-dione), or to determine doses of the treatment compound for the subject.

5.1 Definitions

As used herein, and unless otherwise specified, the terms "treat," "treating," and "treatment" refer to an action that occurs while a patient is suffering from a disease or disorder such as SLE, which reduces the severity of the disease or disorder or retards or slows the progression of the disease or disorder.

The term "sensitivity" or "sensitive" when made in reference to treatment with compound is a relative term which refers to the degree of effectiveness of the compound in lessening or decreasing the progress of a tumor or the disease being treated. For example, the term "increased sensitivity" when used in reference to treatment of SLE in connection with a compound refers to an increase of, at least about 5%, or more, in the effectiveness of the SLE treatment.

As used herein, the terms "compound" and "treatment compound" are used interchangeably, and include the compounds of Formula I. Non-limiting examples of compounds include those disclosed in Section 5.5 below.

As used herein, and unless otherwise specified, the term "therapeutically effective amount" of a compound is an amount sufficient to provide a therapeutic benefit in the treatment or management of a disease or disorder (e.g., SLE), or to delay or minimize one or more symptoms associated with the presence of the a disease or disorder (e.g., SLE). A therapeutically effective amount of a compound means an amount of therapeutic agent, alone or in combination with other therapies, which provides a therapeutic benefit in the treatment or management of the a disease or disorder (e.g., SLE). The term "therapeutically effective amount" can encompass an amount that improves overall therapy, reduces or avoids symptoms or causes of a disease or disorder (e.g., SLE), or enhances the therapeutic efficacy of another therapeutic agent. The term also refers to the amount of a compound that is sufficient to elicit the biological or medical response of a biological molecule (e.g., a protein, enzyme, RNA, or DNA), cell, tissue, system, animal, or human, which is being sought by a researcher, veterinarian, medical doctor, or clinician.

The term "responsiveness" or "responsive" when used in reference to a treatment refers to the degree of effectiveness of the treatment in lessening or decreasing the symptoms of a disease, e.g., SLE, being treated. For example, the term "increased responsiveness" when used in reference to a treatment of a cell or a subject refers to an increase in the effectiveness in lessening or decreasing the symptoms of the disease compared to a reference treatment (e.g., of the same cell or subject, or of a different cell or subject) when measured using any methods known in the art. In certain embodiments, the increase in the effectiveness is at least about 5%, at least about 10%, at least about 20%, at least about 30%, at least about 40%, or at least about 50%.

As used herein, the terms "effective subject response," "effective patient response," and "effective patient tumor response" refer to any increase in the therapeutic benefit to the patient.

The term "likelihood" generally refers to an increase in the probability of an event. The term "likelihood" when used in reference to the effectiveness of a treatment in a subject generally contemplates an increased probability that progress or degree of the disease will decrease.

The term "predict" generally means to determine or tell in advance. When used to "predict" the effectiveness of a treatment, for example, the term "predict" can mean that the likelihood of the outcome of the treatment can be determined at the outset, before the treatment has begun, or before the treatment period has progressed substantially.

The term "monitor," as used herein, generally refers to the overseeing, supervision, regulation, watching, tracking, or surveillance of an activity. For example, the term "monitoring the effectiveness of a compound" refers to tracking the effectiveness in treating a disease or disorder (e.g., SLE) in a patient. Similarly, the term "monitoring," when used in connection with patient compliance, either individually, or in a clinical trial, refers to the tracking or confirming that the patient is actually taking a drug being tested as prescribed. The monitoring can be performed, for example, by following the expression of mRNA or protein biomarkers.

A "biological marker" or "biomarker" is a substance whose detection indicates a particular biological state. In some embodiments, biomarkers can be determined individually.

The term "expressed" or "expression" as used herein refers to the transcription from a gene to give an RNA nucleic acid molecule at least complementary in part to a region of one of the two nucleic acid strands of the gene. The term "expressed" or "expression" as used herein also refers to the translation from the RNA molecule to give a protein, a polypeptide, or a portion thereof.

The term "level" refers to the amount, accumulation, or rate of a biomarker molecule. A level can be represented, for example, by the amount or the rate of synthesis of a messenger RNA (mRNA) encoded by a gene, the amount or the rate of synthesis of a polypeptide or protein encoded by a gene, or the amount or the rate of synthesis of a biological molecule accumulated in a cell or biological fluid. The term "level" refers to an absolute amount of a molecule in a sample or a relative amount of the molecule, determined under steady-state or non-steady-state conditions.

The terms "determining," "measuring," "evaluating," "assessing," and "assaying" as used herein generally refer to any form of measurement, and include determining whether an element is present or not. These terms include quantitative and/or qualitative determinations. Assessing may be relative or absolute. "Assessing the presence of" can include determining the amount of something present, as well as determining whether it is present or absent.

The term "sample" as used herein relates to a material or mixture of materials, typically, although not necessarily, in fluid form, containing one or more components of interest.

"Biological sample" as used herein refers to a sample obtained from a biological subject, including a sample of biological tissue or fluid origin, obtained, reached, or collected in vivo or in situ. Such samples can be, but are not limited to, organs, tissues, and cells isolated from a mammal. Exemplary biological samples include but are not limited to cell lysate, a cell culture, a cell line, a tissue, oral tissue, gastrointestinal tissue, an organ, an organelle, a biological fluid, a blood sample, a urine sample, a skin sample, and the like.

"Tautomer" as used herein refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

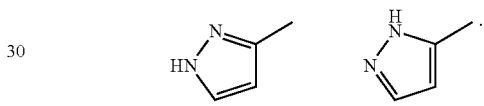

As used herein and unless otherwise indicated, the term "pharmaceutically acceptable salt" encompasses non-toxic acid and base addition salts of the compound to which the term refers. Acceptable non-toxic acid addition salts include those derived from organic and inorganic acids know in the art, which include, for example, hydrochloric acid, hydrobromic acid, phosphoric acid, sulfuric acid, methanesulphonic acid, acetic acid, tartaric acid, lactic acid, succinic acid, citric acid, malic acid, maleic acid, sorbic acid, aconitic acid, salicylic acid, phthalic acid, embolic acid, enanthic acid, and the like. Compounds that are acidic in nature are capable of forming salts with various pharmaceutically acceptable bases. The bases that can be used to prepare pharmaceutically acceptable base addition salts of such acidic compounds are those that form non-toxic base addition salts, i.e., salts containing pharmacologically acceptable cations such as, but not limited to, alkali metal or alkaline earth metal salts (calcium, magnesium, sodium, or potassium salts in particular). Suitable organic bases include, but are not limited to, N,N-dibenzylethylenediamine, chloroprocaine, choline, diethanolamine, ethylenediamine, meglumine (N-methylglucamine), lysine, and procaine.

As used herein and unless otherwise indicated, the term "solvate" means a compound provided herein or a salt thereof that further includes a stoichiometric or non-stoichiometric amount of solvent bound by non-covalent intermolecular forces. Where the solvent is water, the solvate is a hydrate.

As used herein, and unless otherwise specified, the term "stereoisomer" encompasses all enantiomerically/stereomerically pure and enantiomerically/stereomerically enriched compounds of this invention.

As used herein and unless otherwise indicated, the term "stereomerically pure" means a composition that comprises one stereoisomer of a compound and is substantially free of other stereoisomers of that compound. For example, a stereomerically pure composition of a compound having one chiral center will be substantially free of the opposite enantiomer of the compound. A stereomerically pure composition of a compound having two chiral centers will be substantially free of other diastereomers of the compound. A typical stereomerically pure compound comprises greater than about 80% by weight of one stereoisomer of the compound and less than about 20% by weight of other stereoisomers of the compound, more preferably greater than about 90% by weight of one stereoisomer of the compound and less than about 10% by weight of the other stereoisomers of the compound, even more preferably greater than about 95% by weight of one stereoisomer of the compound and less than about 5% by weight of the other stereoisomers of the compound, and most preferably greater than about 97% by weight of one stereoisomer of the compound and less than about 3% by weight of the other stereoisomers of the compound.

As used herein and unless otherwise indicated, the term "stereomerically enriched" means a composition that comprises greater than about 60% by weight of one stereoisomer of a compound, preferably greater than about 70% by weight, more preferably greater than about 80% by weight of one stereoisomer of a compound. As used herein and unless otherwise indicated, the term "enantiomerically pure" means a stereomerically pure composition of a compound having one chiral center. Similarly, the term "stereomerically enriched" means a stereomerically enriched composition of a compound having one chiral center.

It should also be noted compounds can contain unnatural proportions of atomic isotopes at one or more of the atoms. For example, the compounds may be radiolabeled with radioactive isotopes, such as for example tritium ($^3$H), iodine-125 ($^{125}$I), sulfur-35 ($^{35}$S), or carbon-14 ($^{14}$C), or may be isotopically enriched, such as with deuterium ($^2$H), carbon-13 ($^{13}$C), or nitrogen-15 ($^{15}$N). As used herein, an "isotopologue" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer and inflammation therapeutic agents, research reagents, e.g., binding assay reagents, and diagnostic agents, e.g., in vivo imaging agents. All isotopic variations of the compounds as described herein, whether radioactive or not, are intended to be encompassed within the scope of the embodiments provided herein. In some embodiments, there are provided isotopologues of the compounds, for example, the isotopologues are deuterium, carbon-13, or nitrogen-15 enriched compounds. In some embodiments, isotopologues provided herein are deuterium enriched compounds. In some embodiments, isotopologues provided herein are deuterium enriched compounds, where the deuteration occurs on the chiral center. In some embodiments, provided herein are isotopologues of the compounds of Formula I, where deuteration occurs on the chiral center. In some embodiments, provided herein are isotopologues of Compound C, where deuteration occurs on the chiral center.

The terms "polypeptide" and "protein," as used interchangeably herein, refer to a polymer of three or more amino acids in a serial array, linked through peptide bonds. The term "polypeptide" includes proteins, protein fragments, protein analogues, oligopeptides, and the like. The term "polypeptide" as used herein can also refer to a peptide. The amino acids making up the polypeptide may be naturally derived, or may be synthetic. The polypeptide can be purified from a biological sample. The polypeptide, protein, or peptide also encompasses modified polypeptides, proteins, and peptides, e.g., glycopolypeptides, glycoproteins, or glycopeptides; or lipopolypeptides, lipoproteins, or lipopeptides.

The term "antibody," "immunoglobulin," or "Ig" as used interchangeably herein, encompasses fully assembled antibodies and antibody fragments that retain the ability to specifically bind to the antigen. Antibodies provided herein include, but are not limited to, synthetic antibodies, monoclonal antibodies, polyclonal antibodies, recombinantly produced antibodies, multispecific antibodies (including bispecific antibodies), human antibodies, humanized antibodies, chimeric antibodies, intrabodies, single-chain Fvs (scFv) (e.g., including monospecific, bispecific, etc.), camelized antibodies, Fab fragments, F(ab') fragments, disulfide-linked Fvs (sdFv), anti-idiotypic (anti-Id) antibodies, and epitope-binding fragments of any of the above. In particular, antibodies provided herein include immunoglobulin molecules and immunologically active portions of immunoglobulin molecules, i.e., antigen binding domains or molecules that contain an antigen-binding site that immunospecifically binds to CRBN antigen (e.g., one or more complementarity determining regions (CDRs) of an anti-CRBN antibody). The antibodies provided herein can be of any class (e.g., IgG, IgE, IgM, IgD, and IgA) or any subclass (e.g., IgG1, IgG2, IgG3, IgG4, IgA1, and IgA2) of immunoglobulin molecule. In some embodiments, the anti-CRBN antibodies are fully human, such as fully human monoclonal CRBN antibodies. In certain embodiments, antibodies provided herein are IgG antibodies, or a subclass thereof (e.g., human IgG1 or IgG4).

The terms "nucleic acid" and "polynucleotide" are used interchangeably herein to describe a polymer of any length composed of nucleotides, e.g., deoxyribonucleotides or ribonucleotides, or compounds produced synthetically, which can hybridize with naturally occurring nucleic acids in a sequence specific manner analogous to that of two naturally occurring nucleic acids, e.g., can participate in Watson-Crick base pairing interactions. As used herein in the context of a polynucleotide sequence, the term "bases" (or "base") is synonymous with "nucleotides" (or "nucleotide"), i.e., the monomer subunit of a polynucleotide. The terms "nucleoside" and "nucleotide" are intended to include those moieties that contain not only the known purine and pyrimidine bases, but also other heterocyclic bases that have been modified. Such modifications include methylated purines or pyrimidines, acylated purines or pyrimidines, alkylated riboses or other heterocycles. In addition, the terms "nucleoside" and "nucleotide" include those moieties that contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, or are functionalized as ethers, amines, or the like. "Analogues" refer to molecules having structural features that are recognized in the literature as being mimetics, derivatives, having analogous structures, or other like terms, and include, for example, polynucleotides incorporating non-natural nucleotides, nucleotide mimetics such as 2'-modified nucleosides, peptide nucleic acids, oligomeric nucleoside phosphonates, and any polynucleotide that has added substituent groups, such as protecting groups or linking moieties.

The term "complementary" refers to specific binding between polynucleotides based on the sequences of the polynucleotides. As used herein, a first polynucleotide and a second polynucleotide are complementary if they bind to each other in a hybridization assay under stringent conditions, e.g., if they produce a given or detectable level of signal in a hybridization assay. Portions of polynucleotides are complementary to each other if they follow conventional base-pairing rules, e.g., A pairs with T (or U) and G pairs with C, although small regions (e.g., fewer than about 3 bases) of mismatch, insertion, or deleted sequence may be present.

As used herein, the term "bound" indicates direct or indirect attachment. In the context of chemical structures, "bound" (or "bonded") may refer to the existence of a chemical bond directly joining two moieties or indirectly joining two moieties (e.g., via a linking group or any other intervening portion of the molecule). The chemical bond may be a covalent bond, an ionic bond, a coordination complex, hydrogen bonding, van der Waals interactions, or hydrophobic stacking, or may exhibit characteristics of multiple types of chemical bonds. In certain instances, "bound" includes embodiments where the attachment is direct and embodiments where the attachment is indirect.

The term "capture agent" as used herein refers to an agent that binds an mRNA or protein through an interaction that is sufficient to permit the agent to bind and to concentrate the mRNA or protein from a heterogeneous mixture.

The term "probe" as used herein refers to a capture agent that is directed to a specific target mRNA biomarker sequence. Accordingly, each probe of a probe set has a respective target mRNA biomarker. A probe/target mRNA duplex is a structure formed by hybridizing a probe to its target mRNA biomarker.

The term "nucleic acid probe" or "oligonucleotide probe" refers to a nucleic acid capable of binding to a target nucleic acid of complementary sequence, such as the mRNA biomarkers provided herein, usually through complementary base pairing by forming hydrogen bond. As used herein, a probe may include natural (e.g., A, G, C, or T) or modified bases (7-deazaguanosine, inosine, etc.). In addition, the bases in a probe may be joined by a linkage other than a phosphodiester bond, so long as it does not interfere with hybridization. It will be understood by one of skill in the art that probes may bind target sequences lacking complete complementarity with the probe sequence depending upon the stringency of the hybridization conditions. The probes are preferably directly labeled with tags, for example, chromophores, lumiphores, chromogens, or indirectly labeled with biotin to which a streptavidin complex may later bind. By assaying for the presence or absence of the probe, one can detect the presence or absence of a target mRNA biomarker of interest.

The term "stringent assay conditions" refers to conditions that are compatible to produce binding pairs of nucleic acids, e.g., probes and target mRNAs, of sufficient complementarity to provide for the desired level of specificity in the assay while being generally incompatible to the formation of binding pairs between binding members of insufficient complementarity to provide for the desired specificity. The term "stringent assay conditions" generally refers to the combination of hybridization and wash conditions.

A "label" or "detectable moiety" in reference to a nucleic acid refers to a composition that, when linked with a nucleic acid, renders the nucleic acid detectable, for example, by spectroscopic, photochemical, biochemical, immunochemical, or chemical means. Exemplary labels include, but are not limited to, radioactive isotopes, magnetic beads, metallic beads, colloidal particles, fluorescent dyes, enzymes, biotin, digoxigenin, haptens, and the like. A "labeled nucleic acid or oligonucleotide probe" is generally one that is bound, either covalently through a linker or a chemical bond, or noncovalently through ionic bonds, van der Waals forces, electrostatic attractions, hydrophobic interactions, or hydrogen bonds, to a label such that the presence of the nucleic acid or probe can be detected by detecting the presence of the label bound to the nucleic acid or probe.

The term "polymerase chain reaction" or "PCR" as used herein generally refers to a procedure wherein small amounts of a nucleic acid, RNA and/or DNA, are amplified as described, for example, in U.S. Pat. No. 4,683,195. Generally, sequence information from the ends or beyond of the region of interest needs to be available, such that oligonucleotide primers can be designed; these primers will be identical or similar in sequence to opposite strands of the template to be amplified. The 5' terminal nucleotides of the two primers may coincide with the ends of the amplified material. PCR can be used to amplify specific RNA sequences, specific DNA sequences from total genomic DNA, and cDNA transcribed from total cellular RNA, bacteriophage, or plasmid sequences, etc. See generally Mullis et al., *Cold Spring Harbor Symp. Quant. Biol.* 1987, 51:263-273; *PCR Technology* (Stockton Press, NY, Erlich, ed., 1989).

The term "cycle number" or "$C_T$" when used herein in reference to PCR methods, refers to the PCR cycle number at which the fluorescence level passes a given set threshold level. The $C_T$ measurement can be used, for example, to approximate levels of mRNA in an original sample. The $C_T$ measurement is often used in terms of "$dC_T$" or the "difference in the $C_T$" score, when the $C_T$ of one nucleic acid is subtracted from the $C_T$ of another nucleic acid.

The term "about" or "approximately" means an acceptable error for a particular value as determined by one of ordinary skill in the art, which depends in part on how the value is measured or determined. In certain embodiments, the term "about" or "approximately" means within 1, 2, 3, or 4 standard deviations. In certain embodiments, the term "about" or "approximately" means within 50%, 20%, 15%, 10%, 9%, 8%, 7%, 6%, 5%, 4%, 3%, 2%, 1%, 0.5%, or 0.05% of a given value or range.

It should be noted that if there is a discrepancy between a depicted structure and a name given to that structure, the depicted structure is to be accorded more weight. In addition, if the stereochemistry of a structure or a portion of a structure is not indicated with, for example, bold or dashed lines, the structure or portion of the structure is to be interpreted as encompassing all stereoisomers of it.

The practice of the embodiments provided herein will employ, unless otherwise indicated, conventional techniques of molecular biology, microbiology, and immunology, which are within the skill of those working in the art. Such techniques are explained fully in the literature. Examples of particularly suitable texts for consultation include the following: Sambrook et al., *Molecular Cloning: A Laboratory Manual* (2d ed. 1989); Glover, ed., *DNA Cloning*, Volumes I and II (1985); Gait, ed., *Oligonucleotide Synthesis* (1984); Hames & Higgins, eds., *Nucleic Acid Hybridization* (1984); Hames & Higgins, eds., *Transcription and Translation* (1984); Freshney, ed., *Animal Cell Culture: Immobilized Cells and Enzymes* (IRL Press, 1986); *Immunochemical*

*Methods in Cell and Molecular Biology* (Academic Press, London); Scopes, *Protein Purification: Principles and Practice* (Springer Verlag, N.Y., 2d ed. 1987); and Weir & Blackwell, eds., *Handbook of Experimental Immunology*, Volumes I-IV (1986).

5.2 Biomarkers and Methods of Use Thereof

In one aspect, provided herein is a method of determining a dose of the treatment compound provided herein for treating a subject having systemic lupus erythematosus (SLE) based on the expression level of IKZF3 in a sample obtained from the subject.

More specifically, in some embodiments, the method provided herein comprises (a) obtaining a sample from the subject; (b) measuring the gene expression level of IKZF3 in the sample; and (c) determining the dose of the treatment compound based on the measurement of the gene expression level of IKZF3, wherein the treatment compound is a compound of Formula I:

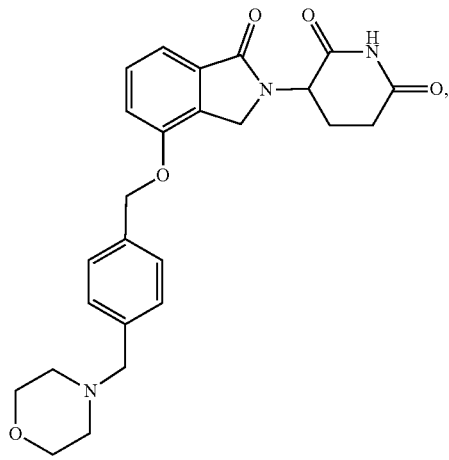

or a pharmaceutically acceptable salt, solvate, hydrate, stereoisomer, tautomer or racemic mixture thereof.

In some embodiments, the method comprises determining the dose of the treatment compound to be 0.45 mg or higher per day if a score calculated based on the gene expression level of IKZF3 in the sample is higher than a reference level.

In some embodiments, the score is Log 2 of the gene expression level of IKZF3 relative to a reference gene in the sample, or wherein the score is Log 2 of the gene expression level of IKZF3 relative to an average gene expression level of two or more reference genes in the sample. In some embodiments, the method comprises determining the dose of the treatment compound to be 0.45 mg or higher per day if a score is higher than −0.49. In some embodiments, the reference gene is selected from a group consisting of TFRC, ACTB, GAPDH, and combinations thereof. In some embodiments of various methods and kits provided herein (including those described above and in the sections below), the reference gene is a housekeeping gene.

In some embodiments, the method comprises determining the dose of the treatment compound to be about 0.45 mg per day if the score is higher than the reference level. In some embodiments, the method comprises determining the dose of the treatment compound to be about 0.5 mg per day if the score is higher than the reference level. In some embodiments, the method comprises determining the dose of the treatment compound to be about 0.6 mg per day if the score is higher than the reference level. In other embodiments, the method comprises determining the dose of the treatment compound to be about 0.7 mg per day if the score is higher than the reference level.

In some embodiments, the gene expression level is measured by determining the protein level. In other embodiments, the gene expression level is measured by determining the mRNA level. In yet other embodiments, the gene expression level is measured by determining the cDNA level.

In some embodiments, the compound is (S)-3-[4-(4-morpholin-4-ylmethylbenzyloxy)-1-oxo-1,3-dihydro-isoindo-2-yl]piperidine-2,6-dione or a pharmaceutically acceptable salt, solid form, solvate, hydrate, tautomer, stereoisomer or racemate thereof. In some embodiments, the compound is (S)-3-[4-(4-morpholin-4-ylmethylbenzyloxy)-1-oxo-1,3-dihydro-isoindo-2-yl]piperidine-2,6-dione. In yet other embodiments, the compound is (S)-3-[4-(4-morpholin-4-ylmethylbenzyloxy)-1-oxo-1,3-dihydro-isoindo-2-yl]piperidine-2,6-dione hydrochloride.

In some embodiments, the method further comprises administering the dose of 0.45 mg or higher per day of the treatment compound to the subject. In some embodiments, the method further comprises administering the dose of about 0.45 mg per day of the treatment compound to the subject. In some embodiments, the method further comprises administering the dose of about 0.5 mg per day of the treatment compound to the subject. In some embodiments, the method further comprises administering the dose of about 0.55 mg per day of the treatment compound to the subject. In some embodiments, the method further comprises administering the dose of about 0.6 mg per day of the treatment compound to the subject. In some embodiments, the method further comprises administering the dose of about 0.65 mg per day of the treatment compound to the subject. In some embodiments, the method further comprises administering the dose of about 0.7 mg per day of the treatment compound to the subject. In some embodiments, the method further comprises administering the dose of about 0.75 mg per day of the treatment compound to the subject. In some embodiments, the method further comprises administering the dose of about 0.8 mg per day of the treatment compound to the subject.

Thus, provided herein in some embodiments is a method of treating a subject having systemic lupus erythematosus (SLE), comprising administering to the subject with a dose of a treatment compound of 0.45 mg or higher per day, wherein a score calculated based on the gene expression level of IKZF3 in a sample from the subject is higher than a reference level; and wherein the treatment compound is a compound of Formula I:

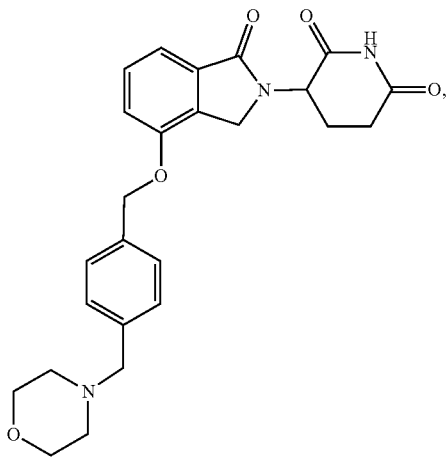

or a pharmaceutically acceptable salt, solvate, hydrate, stereoisomer, tautomer or racemic mixture thereof.

In some embodiments, the score is Log 2 of the gene expression level of IKZF3 relative to a reference gene, or wherein the score is Log 2 of the gene expression level of IKZF3 relative to an average gene expression level of two or more reference genes. In some embodiments, the reference level is −0.49. In some embodiments, the reference gene is selected from a group consisting of TFRC, ACTB, GAPDH, and combinations thereof.

In some embodiments, the dose of the treatment compound is about 0.45 mg per day. In some embodiments, the dose of the treatment compound is about 0.5 mg per day. In some embodiments, the dose of the treatment compound is about 0.6 mg per day. In other embodiments, the dose of the treatment compound is about 0.7 mg per day.

In some embodiments, provided herein is a method of treating a subject having systemic lupus erythematosus (SLE), comprising administering to the subject with a dose of a treatment compound of 0.45 mg or higher per day or 0.15 mg or lower per day, wherein the subject has a high type 1 IFN expression and/or gene signature; and wherein the treatment compound is a compound of Formula I:

I

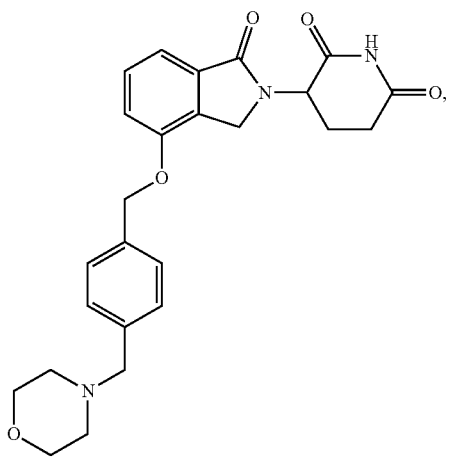

or a pharmaceutically acceptable salt, solvate, hydrate, stereoisomer, tautomer or racemic mixture thereof.

In another aspect, provided herein is a method of determining a dose of the treatment compound provided herein for treating a subject having systemic lupus erythematosus (SLE) based on a high type 1 IFN expression and/or gene signature. In some embodiments, the type 1 IFN expression and/or gene signature is determined based on the expression level of IFI27, IFI44, IFI44L, and RSAD2 in a sample from the subject.

More specifically, in some embodiments, the method comprises (a) obtaining a sample from the subject; (b) measuring the gene expression levels of IFI27, IFI44, IFI44L, and RSAD2 in the sample; and (c) determining the dose of the treatment compound based on the measurement in step (b), wherein the treatment compound is a compound of Formula I:

I or a pharmaceutically acceptable salt, solvate, hydrate, stereoisomer, tautomer or racemic mixture thereof.

In some embodiments, the method comprises determining the dose of the treatment compound to be 0.45 mg or higher per day or to be 0.15 mg or lower per day if a score calculated based on the gene expression levels of IFI27, IFI44, IFI44L, and RSAD2 is higher than a reference level.

Type 1 INF expression/signature can be determined based on any known methods in the field. In some embodiments, the score is Log 2 of an average of the gene expression levels of IFI27, IFI44, IFI44L, and RSAD2 relative to a reference gene in the sample, or wherein the score is Log 2 of an average of the gene expression levels of IFI27, IFI44, IFI44L, and RSAD2 relative to an average of two or more reference genes in the sample. In some embodiments, the method comprises determining the dose of the treatment compound to be 0.45 mg or higher per day or to be 0.15 mg or lower per day if a score is higher than −1.38. In some embodiments, the reference gene is selected from a group consisting of TFRC, ACTB, GAPDH, and combinations thereof.

In some embodiments, the method comprises determining the dose of the treatment compound to be about 0.45 mg per day if the score is higher than the reference level. In some embodiments, the method comprises determining the dose of the treatment compound to be about 0.5 mg per day if the score is higher than the reference level. In other embodiments, the method comprises determining the dose of the treatment compound to be about 0.6 mg per day if the score is higher than the reference level. In other embodiments, the method comprises determining the dose of the treatment compound to be about 0.7 mg per day if the score is higher than the reference level. In some embodiments, the method comprises determining the dose of the treatment compound to be about 0.15 mg per day if the score is higher than the reference level. In other embodiments, the method comprises determining the dose of the treatment compound to be about 0.1 mg per day if the score is higher than the reference level. In other embodiments, the method comprises determining the dose of the treatment compound to be about 0.75 mg per day if the score is higher than the reference level. The frequency of the treatment can be adjusted, for example, once daily, every other day, every three days, or once a week. For example, in some embodiments, the method comprises determining the dose of the treatment compound to be about 0.15 mg daily, about 0.15 mg every other day, about 0.15 mg every three days, or about 0.15 mg once a week, if the score is higher than the reference level.

In some embodiments, the gene expression level is measured by determining the protein level. In other embodiments, the gene expression level is measured by determining the mRNA level. In yet other embodiments, the gene expression level is measured by determining the cDNA level.

In some embodiments, the compound is (S)-3-[4-(4-morpholin-4-ylmethylbenzyloxy)-1-oxo-1,3-dihydro-isoindo-2-yl]piperidine-2,6-dione or a pharmaceutically acceptable salt, solid form, solvate, hydrate, tautomer, stereoisomer or racemate thereof. In some embodiments, the compound is (S)-3-[4-(4-morpholin-4-ylmethylbenzyloxy)-1-oxo-1,3-dihydro-isoindo-2-yl]piperidine-2,6-dione. In yet other embodiments, the compound is (S)-3-[4-(4-morpholin-4-ylmethylbenzyloxy)-1-oxo-1,3-dihydro-isoindo-2-yl]piperidine-2,6-dione hydrochloride.

In some embodiments, the method comprises administering the dose of 0.45 mg or higher per day or 0.15 mg or lower per day of the treatment compound to the subject. In some embodiments, the method further comprises administering the dose of about 0.45 mg per day of the treatment compound to the subject. In some embodiments, the method further comprises administering the dose of about 0.5 mg per day of the treatment compound to the subject. In some embodiments, the method further comprises administering the dose of about 0.55 mg per day of the treatment compound to the subject. In some embodiments, the method further comprises administering the dose of about 0.6 mg per day of the treatment compound to the subject. In some embodiments, the method further comprises administering the dose of about 0.65 mg per day of the treatment compound to the subject. In some embodiments, the method further comprises administering the dose of about 0.7 mg per day of the treatment compound to the subject. In some embodiments, the method further comprises administering the dose of about 0.75 mg per day of the treatment compound to the subject. In some embodiments, the method further comprises administering the dose of about 0.8 mg per day of the treatment compound to the subject. In some embodiments, the method further comprises administering the dose of about 0.15 mg per day of the treatment compound to the subject. In some embodiments, the method further comprises administering the dose of about 0.11 mg per day of the treatment compound to the subject. In some embodiments, the method further comprises administering the dose of about 0.10 mg per day of the treatment compound to the subject. In some embodiments, the method further comprises administering the dose of about 0.08 mg per day of the treatment compound to the subject. In some embodiments, the method further comprises administering the dose of about 0.075 mg per day of the treatment compound to the subject. In some embodiments, the method further comprises administering the dose of about 0.06 mg per day of the treatment compound to the subject. The frequency of the treatment can be adjusted, for example, once daily, every other day, every three days, or once a week. For example, in some embodiments, the method comprises administering about 0.15 mg of the treatment compound daily, about 0.15 mg of the treatment compound every other day, about 0.15 mg of the treatment compound every three days, or about 0.15 mg of the treatment compound once a week.

Thus, provided herein in some embodiments is a method of treating a subject having systemic lupus erythematosus (SLE), comprising administering to the subject with a dose of a treatment compound of 0.45 mg or higher per day or 0.15 mg or lower per day, wherein the subject is determined to have the high type 1 IFN expression and/or gene signature, and wherein the treatment compound is a compound of Formula I:

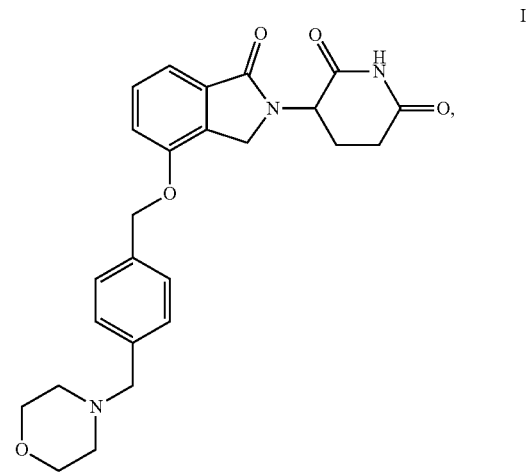 [SMILES: O=C1CCC(N2Cc3c(OCc4ccc(CN5CCOCC5)cc4)cccc3C2=O)C(=O)N1]

or a pharmaceutically acceptable salt, solvate, hydrate, stereoisomer, tautomer or racemic mixture thereof.

In some embodiments, the subject is determined to have the high type 1 IFN expression and/or gene signature if a score calculated based on the gene expression levels of IFI27, IFI44, IFI44L, and RSAD2 in a sample from the subject is higher than a reference level. In some embodiments, the score is Log 2 of an average of the gene expression levels of IFI27, IFI44, IFI44L, and RSAD2 relative to a reference gene in the sample, or wherein the score is Log 2 of an average of the gene expression levels of IFI27, IFI44, IFI44L, and RSAD2 relative to an average of two or more reference genes in the sample. In some embodiments, the score is higher than −1.38. In some embodiments, the reference gene is selected from a group consisting of TFRC, ACTB, GAPDH, and combinations thereof.

In some embodiments, the dose of the treatment compound is about 0.45 mg per day. In some embodiments, the dose of the treatment compound is about 0.5 mg per day. In some embodiments, the dose of the treatment compound is about 0.6 mg per day. In other embodiments, the dose of the treatment compound is about 0.7 mg per day. In some embodiments, the dose of the treatment compound is about 0.15 mg per day. In other embodiments, the dose of the treatment compound is about 0.1 mg per day. In yet other embodiments, the dose of the treatment compound is about 0.075 mg per day. The frequency of the treatment can be adjusted, for example, once daily, every other day, every three days, or once a week. For example, in some embodiments, the method comprises administering about 0.15 mg of the treatment compound daily, about 0.15 mg of the treatment compound every other day, about 0.15 mg of the treatment compound every three days, or about 0.15 mg of the treatment compound once a week.

In yet another aspect, provided herein is a method of identifying a subject having systemic lupus erythematosus (SLE) who is likely to be responsive to a treatment compound or predicting the responsiveness of a subject having SLE to a treatment compound, comprising (a) obtaining a sample from the subject; (b) determining the gene expression level of IKZF3; and (c) diagnosing the subject as being likely to be responsive to the treatment compound if a score calculated based on the gene expression level of IKZF3 is higher than a reference level, wherein the treatment compound is a compound of Formula I:

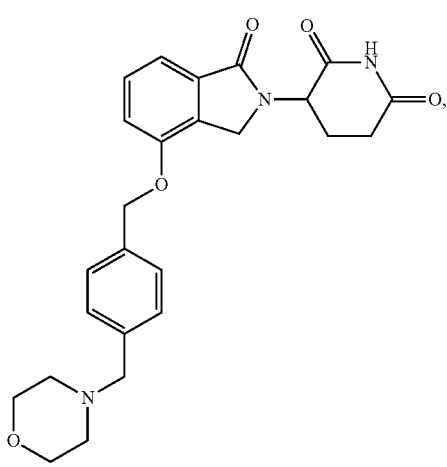

or a pharmaceutically acceptable salt, solvate, hydrate, stereoisomer, tautomer or racemic mixture thereof.

In some embodiments, the method comprises determining the gene expression level of IKZF3 and diagnosing the subject as being likely to be responsive to the treatment compound if the score calculated based on the gene expression level of IKZF3 is higher than the reference level. In some embodiments, the score is Log 2 of the gene expression level of IKZF3 relative to a reference gene in the sample, or wherein the score is Log 2 of the gene expression level of IKZF3 relative to an average gene expression level of two or more reference genes in the sample. In some embodiments, the reference level is −0.49. In some embodiments, the reference gene is selected from a group consisting of TFRC, ACTB, GAPDH, and combinations thereof.

In some embodiments, the gene expression level is measured by determining the protein level. In other embodiments, the gene expression level is measured by determining the mRNA level. In yet other embodiments, the gene expression level is measured by determining the cDNA level.

In some embodiments, the compound is (S)-3-[4-(4-morpholin-4-ylmethylbenzyloxy)-1-oxo-1,3-dihydro-isoindo-2-yl]piperidine-2,6-dione or a pharmaceutically acceptable salt, solid form, solvate, hydrate, tautomer, stereoisomer or racemate thereof. In some embodiments, the compound is (S)-3-[4-(4-morpholin-4-ylmethylbenzyloxy)-1-oxo-1,3-dihydro-isoindo-2-yl]piperidine-2,6-dione. In yet other embodiments, the compound is (S)-3-[4-(4-morpholin-4-ylmethylbenzyloxy)-1-oxo-1,3-dihydro-isoindo-2-yl]piperidine-2,6-dione hydrochloride.

In some embodiments, the method further comprises administering an effective amount of the treatment compound to the subject determined to be likely to be responsive to the treatment compound.

In yet another aspect, provided herein is a method of identifying a subject having systemic lupus erythematosus (SLE) who is likely to be responsive to a treatment compound or predicting the responsiveness of a subject having SLE to a treatment compound, comprising (a) obtaining a sample from the subject; (b) determining the gene expression levels of IFI27, IFI44, IFI44L, and RSAD2 in the sample; and (c) diagnosing the subject as being likely to be responsive to the treatment compound if a score calculated based on the gene expression levels of IFI27, IFI44, IFI44L, and RSAD2 is higher than a reference level, wherein the treatment compound is a compound of Formula I:

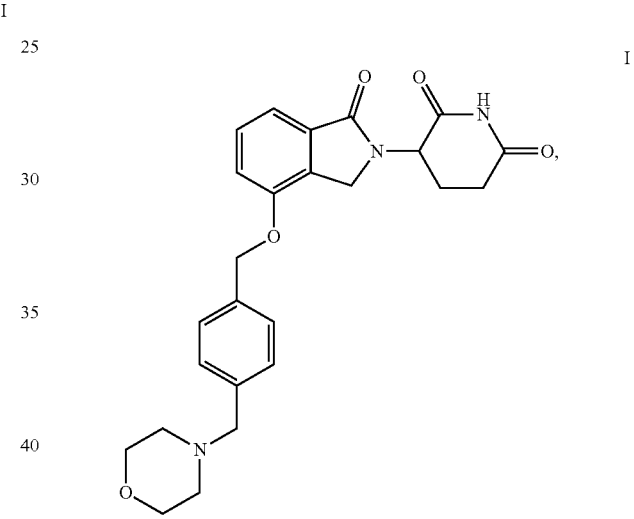

or a pharmaceutically acceptable salt, solvate, hydrate, stereoisomer, tautomer or racemic mixture thereof.

In other embodiments, the method comprises determining the gene expression levels of IFI27, IFI44, IFI44L, and RSAD2 and diagnosing the subject as being likely to be responsive to the treatment compound if the score calculated based on the gene expression levels of IFI27, IFI44, IFI44L, and RSAD2 is higher than the reference level. In some embodiments, the score is Log 2 of an average of the gene expression levels of IFI27, IFI44, IFI44L, and RSAD2 relative to a reference gene in the sample, or wherein the score is Log 2 of an average of the gene expression levels of IFI27, IFI44, IFI44L, and RSAD2 relative to an average of two or more reference genes in the sample. In some embodiments, the reference level is −1.38. In some embodiments, the reference gene is selected from a group consisting of TFRC, ACTB, GAPDH, and combinations thereof.

In some embodiments, the gene expression level is measured by determining the protein level. In other embodiments, the gene expression level is measured by determining the mRNA level. In yet other embodiments, the gene expression level is measured by determining the cDNA level.

In some embodiments, the compound is (S)-3-[4-(4-morpholin-4-ylmethylbenzyloxy)-1-oxo-1,3-dihydro-isoindo-2-yl]piperidine-2,6-dione or a pharmaceutically acceptable salt, solid form, solvate, hydrate, tautomer, stereoisomer or racemate thereof. In some embodiments, the compound is (S)-3-[4-(4-morpholin-4-ylmethylbenzyloxy)-1-oxo-1,3-dihydro-isoindo-2-yl]piperidine-2,6-dione. In yet other embodiments, the compound is (S)-3-[4-(4-morpholin-4-ylmethylbenzyloxy)-1-oxo-1,3-dihydro-isoindo-2-yl]piperidine-2,6-dione hydrochloride.

In some embodiments, the method further comprises administering an effective amount of the treatment compound to the subject determined to be likely to be responsive to the treatment compound. Thus, in some embodiments, provided herein is a method of treating a subject having systemic lupus erythematosus (SLE) comprising administering an effective amount of a treatment compound to the subject, wherein the subject has been determined to be likely to be responsive to the treatment compound according to the method provided herein, wherein the treatment compound is a compound of Formula I:

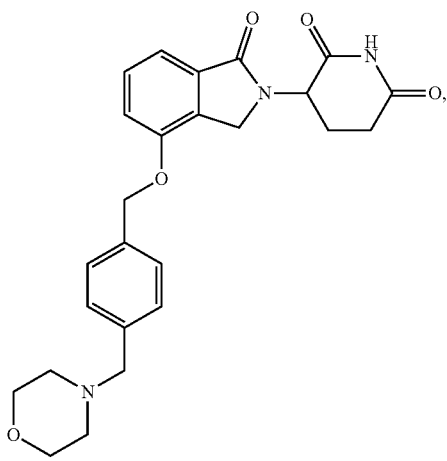

I or a pharmaceutically acceptable salt, solvate, hydrate, stereoisomer, tautomer or racemic mixture thereof.

In yet another aspect, provided herein is a method of determining a dose of a treatment compound provided herein for treating a subject having systemic lupus erythematosus (SLE) based on the expression levels of IKZF3, IFI27, IFI44, IFI44L, and RSAD2.

More specifically, in some embodiments, the method comprises (a) obtaining a sample from the subject; (b) measuring (i) the gene expression level of IKZF3 and (ii) the gene expression levels of IFI27, IFI44, IFI44L, and RSAD2 in the sample; (c) determining a first score based on the gene expression level of IKZF3 and comparing the first score with a first reference level; (d) determining a second score based on the gene expression levels of IFI27, IFI44, IFI44L, and RSAD2 and comparing the second score with a second reference level; and (e) determining the dose of the treatment compound based on the first score and the second score, wherein the treatment compound is a compound Formula I:

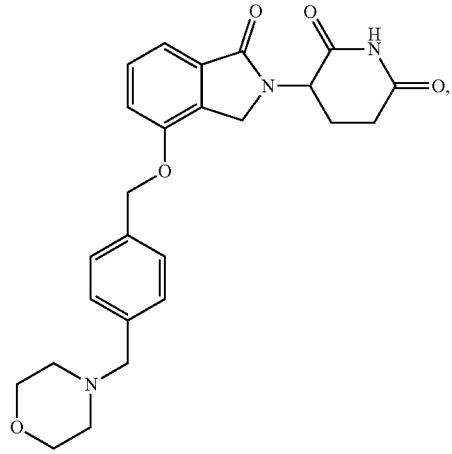

I or a pharmaceutically acceptable salt, solvate, hydrate, stereoisomer, tautomer or racemic mixture thereof.

In some embodiments, the first score is Log 2 of the gene expression level of IKZF3 relative to a reference gene in the sample, or wherein the first score is Log 2 of the gene expression level of IKZF3 relative to an average gene expression level of two or more reference genes in the sample. In some embodiments, the first reference level is −0.49. In some embodiments, the reference gene is selected from a group consisting of TFRC, ACTB, GAPDH, and combinations thereof.

In some embodiments, the second score is Log 2 of an average of the gene expression levels of IFI27, IFI44, IFI44L, and RSAD2 relative to a reference gene in the sample, or wherein the second score is Log 2 of an average of the gene expression levels of IFI27, IFI44, IFI44L, and RSAD2 relative to an average of two or more reference genes in the sample. In some embodiments, the second reference level is −1.38. In some embodiments, the reference gene is selected from a group consisting of TFRC, ACTB, GAPDH, and combinations thereof.

In some embodiments, when the first score is higher than the first reference level and the second score is higher than the second reference level, the dose of the treatment compound is determined to be 0.45 mg or higher per day or to be 0.15 mg or lower per day. In some embodiments, the method comprises determining the dose of the treatment compound to be about 0.45 mg per day if the score is higher than the reference level. In some embodiments, the method comprises determining the dose of the treatment compound to be about 0.5 mg per day if the score is higher than the reference level. In other embodiments, the method comprises determining the dose of the treatment compound to be about 0.6 mg per day if the score is higher than the reference level. In other embodiments, the method comprises determining the dose of the treatment compound to be about 0.7 mg per day if the score is higher than the reference level. In some embodiments, the method comprises determining the dose of the treatment compound to be about 0.15 mg per day if the score is higher than the reference level. In other embodiments, the method comprises determining the dose of the treatment compound to be about 0.1 mg per day if the score is higher than the reference level. In other embodiments, the method comprises determining the dose of the treatment compound to be about 0.75 mg per day if the score is higher than the reference level. In other embodiments, the method comprises determining the dose of the treatment compound to be about 0.15 mg every other day if the score is higher than the reference level. In other embodiments, the method comprises determining the dose of the treatment compound to be about 0.15 mg every three days if the score is higher than the reference level. In other embodiments, the method comprises determining the dose of the treatment compound to be about 0.15 mg once a week if the score is higher than the reference level.

In other embodiments, when the first score is higher than the first reference level and the second score is lower than the second reference level, the dose of the treatment compound is determined to be 0.15 mg or lower per day. In some embodiments, the method comprises determining the dose of the treatment compound to be about 0.15 mg per day if the score is higher than the reference level. In other embodiments, the method comprises determining the dose of the treatment compound to be about 0.1 mg per day if the score is higher than the reference level. In other embodiments, the method comprises determining the dose of the treatment compound to be about 0.75 mg per day if the score is higher than the reference level.

In yet other embodiments, when the first score is lower than the first reference level and the second score is higher than the second reference level, the dose of the treatment compound is determined to be 0.45 mg or higher per day. In some embodiments, the method comprises determining the dose of the treatment compound to be about 0.45 mg per day if the score is higher than the reference level. In some embodiments, the method comprises determining the dose of the treatment compound to be about 0.5 mg per day if the score is higher than the reference level. In other embodiments, the method comprises determining the dose of the treatment compound to be about 0.6 mg per day if the score is higher than the reference level. In other embodiments, the method comprises determining the dose of the treatment compound to be about 0.7 mg per day if the score is higher than the reference level.

In yet another aspect, provided herein is a method of treating a subject having systemic lupus erythematosus (SLE), comprising administering to the subject with a dose of a treatment compound, wherein the dose of the treatment compound is determined according to the method provided herein; and wherein the treatment compound is a compound of Formula I:

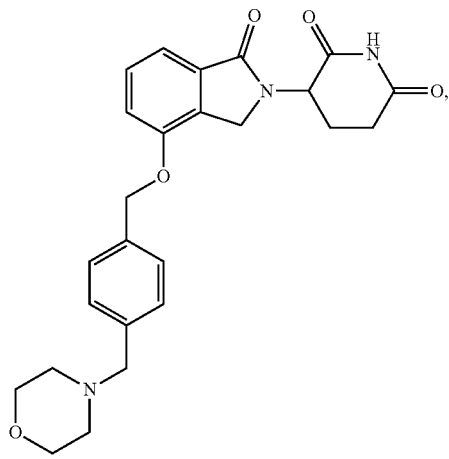

I or a pharmaceutically acceptable salt, solvate, hydrate, stereoisomer, tautomer or racemic mixture thereof.

In some embodiments, the gene expression level is measured by determining the protein level. In other embodiments, the gene expression level is measured by determining the mRNA level. In yet other embodiments, the gene expression level is measured by determining the cDNA level.

In some embodiments, the compound is (S)-3-[4-(4-morpholin-4-ylmethylbenzyloxy)-1-oxo-1,3-dihydro-isoindo-2-yl]piperidine-2,6-dione or a pharmaceutically acceptable salt, solid form, solvate, hydrate, tautomer, stereoisomer or racemate thereof. In some embodiments, the compound is (S)-3-[4-(4-morpholin-4-ylmethylbenzyloxy)-1-oxo-1,3-dihydro-isoindo-2-yl]piperidine-2,6-dione. In yet other embodiments, the compound is (S)-3-[4-(4-morpholin-4-ylmethylbenzyloxy)-1-oxo-1,3-dihydro-isoindo-2-yl]piperidine-2,6-dione hydrochloride.

In yet another aspect, provided herein is a method of identifying a subject having systemic lupus erythematosus (SLE) who is likely to be responsive to a treatment compound or predicting the responsiveness of a subject having SLE to a treatment compound based on the presence of one or two copies of a single nucleotide polymorphism (SNP) of IKZF1, i.e., rs4917014. As shown in Section 6 below, a SLE patient is more likely to be responsive to the treatment with the present compound when at least one copy of this SNP (rs4917014) is detected.

More specifically, in some embodiments, the method comprises (a) obtaining a sample from the subject; (b) determining the presence of IKZF1 single nucleotide polymorphism (SNP) rs4917014 in the sample; and (c) diagnosing the subject as being likely to be responsive to the treatment compound if at least one copy of SNP rs4917014 is detected, wherein the treatment compound is a compound of Formula I:

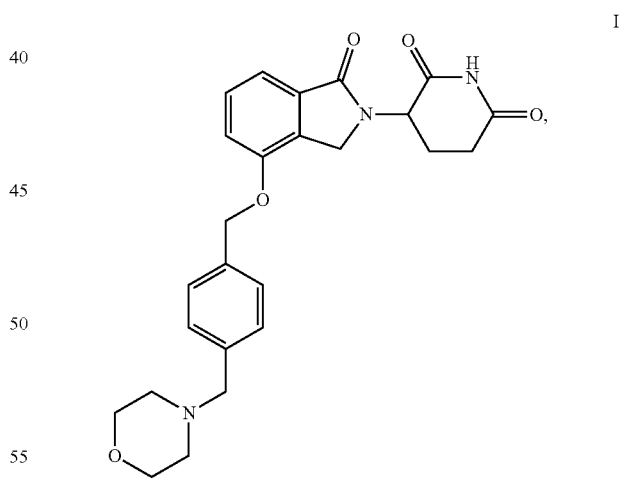

I or a pharmaceutically acceptable salt, solvate, hydrate, stereoisomer, tautomer or racemic mixture thereof. In some embodiments, the method further comprises administering an effective amount of the treatment compound to the subject determined to be likely to be responsive to the treatment compound.

In some embodiments, provided herein is a method of treating a subject having systemic lupus erythematosus (SLE) comprising administering an effective amount of a treatment compound to the subject, wherein the subject has been determined to be likely to be responsive to the treatment compound according to the method provided herein, wherein the treatment compound is a compound of Formula I:

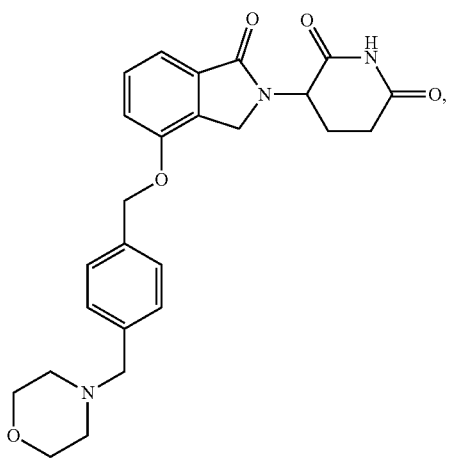

or a pharmaceutically acceptable salt, solvate, hydrate, stereoisomer, tautomer or racemic mixture thereof.

In some embodiments, the compound is (S)-3-[4-(4-morpholin-4-ylmethylbenzyloxy)-1-oxo-1,3-dihydro-isoindo-2-yl]piperidine-2,6-dione or a pharmaceutically acceptable salt, solid form, solvate, hydrate, tautomer, stereoisomer or racemate thereof. In some embodiments, the compound is (S)-3-[4-(4-morpholin-4-ylmethylbenzyloxy)-1-oxo-1,3-dihydro-isoindo-2-yl]piperidine-2,6-dione. In yet other embodiments, the compound is (S)-3-[4-(4-morpholin-4-ylmethylbenzyloxy)-1-oxo-1,3-dihydro-isoindo-2-yl]piperidine-2,6-dione hydrochloride.

In another aspect, provided herein is a use of the treatment compound provided herein in a method provided herein. In yet another aspect, provided herein is the treatment compound provided herein for use in a method provided herein. In yet another aspect, provided herein is a use of the treatment compound for the manufacture of a medicament for the therapeutic and/or prophylactic treatment provided herein. In some embodiments, the treatment compound is a compound of Formula I, or a pharmaceutically acceptable salt, solvate, hydrate, stereoisomer, tautomer or racemic mixture thereof.

In some embodiments, provided herein is a treatment compound for use in treating a subject having systemic lupus erythematosus (SLE), wherein the dose of the treatment compound is determined according a method provided herein.

For example, in some embodiments, provided herein is a treatment compound for use in treating a subject having systemic lupus erythematosus (SLE), wherein the compound is used at a dose of 0.45 mg or higher per day, wherein a score calculated based on the gene expression level of IKZF3 in a sample from the subject is higher than a reference level; and wherein the treatment compound is a compound of Formula I or a pharmaceutically acceptable salt, solvate, hydrate, stereoisomer, tautomer or racemic mixture thereof.

In some embodiments, the score is Log 2 of the gene expression level of IKZF3 relative to a reference gene, or wherein the score is Log 2 of the gene expression level of IKZF3 relative to an average gene expression level of two or more reference genes. In some embodiments, the reference level is −0.49. In some embodiments, the reference gene is selected from a group consisting of TFRC, ACTB, GAPDH, and combinations thereof. In some embodiments, the dose of the treatment compound is about 0.45 mg per day. In some embodiments, the dose of the treatment compound is about 0.5 mg per day. In some embodiments, the dose of the treatment compound is about 0.6 mg per day. In some embodiments, the dose of the treatment compound is about 0.7 mg per day.

In some embodiments, provided herein is a treatment compound for use in treating a subject having systemic lupus erythematosus (SLE), wherein the treatment compound is used at a dose of 0.45 mg or higher per day or 0.15 mg or lower per day, wherein a score calculated based on the gene expression levels of IFI27, IFI44, IFI44L, and RSAD2 in a sample from the subject is higher than a reference level; and wherein the treatment compound is a compound of Formula I or a pharmaceutically acceptable salt, solvate, hydrate, stereoisomer, tautomer or racemic mixture thereof. In some embodiments, the score is Log 2 of an average of the gene expression levels of IFI27, IFI44, IFI44L, and RSAD2 relative to a reference gene in the sample, or wherein the score is Log 2 of an average of the gene expression levels of IFI27, IFI44, IFI44L, and RSAD2 relative to an average of two or more reference genes in the sample. In some embodiments, the score is higher than −1.38. In some embodiments, the reference gene is selected from a group consisting of TFRC, ACTB, GAPDH, and combinations thereof. In some embodiments, the dose of the treatment compound is about 0.45 mg per day. In some embodiments, the dose of the treatment compound is about 0.5 mg per day. In some embodiments, the dose of the treatment compound is about 0.6 mg per day. In some embodiments, the dose of the treatment compound is about 0.7 mg per day. In some embodiments, the dose of the treatment compound is about 0.15 mg per day, wherein optionally, the dose of the treatment compound is about 0.15 mg every other day, about 0.15 mg every three days, or about 0.15 mg once a week. In some embodiments, the dose of the treatment compound is about 0.1 mg per day. In some embodiments, the dose of the treatment compound is about 0.075 mg per day.

In some embodiments, provided herein is a treatment compound for use in treating a subject having systemic lupus erythematosus (SLE), wherein the treatment compound is used at a dose of a treatment compound of 0.45 mg or higher per day or 0.15 mg or lower per day, wherein the subject has a high type 1 IFN expression and/or gene signature; and wherein the treatment compound is a compound of Formula I or a pharmaceutically acceptable salt, solvate, hydrate, stereoisomer, tautomer or racemic mixture thereof. In some embodiments, the subject is determined to have the high type 1 IFN expression and/or gene signature if a score calculated based on the gene expression levels of IFI27, IFI44, IFI44L, and RSAD2 in a sample from the subject is higher than a reference level. In some embodiments, the score is Log 2 of an average of the gene expression levels of IFI27, IFI44, IFI44L, and RSAD2 relative to a reference gene in the sample, or wherein the score is Log 2 of an average of the gene expression levels of IFI27, IFI44, IFI44L, and RSAD2 relative to an average of two or more reference genes in the sample. In some embodiments, the score is higher than −1.38. In some embodiments, the reference gene is selected from a group consisting of TFRC, ACTB, GAPDH, and combinations thereof. In some embodiments, the dose of the treatment compound is about 0.45 mg per day. In some embodiments, the dose of the treatment compound is about 0.5 mg per day. In some embodiments, the dose of the treatment compound is about 0.6 mg per day. In some embodiments, the dose of the treatment compound is about 0.7 mg per day. In some embodiments, the dose of the treatment compound is about 0.15 mg per day, wherein optionally, the dose of the treatment compound is about 0.15 mg every other day, about 0.15 mg every three days, or about 0.15 mg once a week. In some embodiments, the dose of the treatment compound is about 0.1 mg per day. In some embodiments, the dose of the treatment compound is about 0.075 mg per day.

In some embodiments of the various methods provided herein (e.g., as described above), the method comprises treating, preventing, and/or managing systemic lupus erythematosus (SLE), or a symptom thereof, by administering a therapeutically or prophylactically effective amount of Compound I, or a pharmaceutically acceptable salt, solvate, hydrate, stereoisomer, tautomer or racemic mixtures thereof, to a patient having SLE.

In one embodiment, provided herein are methods of treating, preventing, and/or managing SLE or a symptom thereof, comprising administering a therapeutically effective amount of (S)-3-[4-(4-morpholin-4-ylmethylbenzyloxy)-1-oxo-1,3-dihydro-isoindo-2-yl]piperidine-2,6-dione, or a pharmaceutically acceptable salt or solvate thereof, to a patient having SLE.

In one embodiment, provided herein are methods of preventing SLE or a symptom thereof, comprising administering an effective amount of Compound I, or a pharmaceutically acceptable salt, solvate, hydrate, stereoisomer, tautomer or racemic mixtures thereof, to a patient at risk of having SLE. In one embodiment, provided herein are methods of preventing SLE or a symptom thereof, comprising administering an effective amount of (S)-3-[4-(4-morpholin-4-ylmethylbenzyloxy)-1-oxo-1,3-dihydro-isoindo-2-yl]piperidine-2,6-dione, or a pharmaceutically acceptable salt or solvate thereof, to a patient at risk of having SLE.

The phrase "Systemic lupus erythematosus" is interchangeably used herein with SLE and lupus and refers to all manifestations of the disease as known in the art (including remissions and flares). In SLE, abnormal hyperactivity of B lymphocytes and massive abnormal production of immunoglobulin gamma (IgG) auto-antibodies play a key role. This pathological process results in sequestration and destruction of Ig-coated cells, fixation and cleaving of complement proteins, and release of chemotaxins, vasoactive peptides and destructive enzymes into tissues (Hahn B H. Systemic Lupus Erythematosus. In: Kasper D L, Braunwald E, Fauci A S, Hauser S L, Longo D L, Jameson, J L, editors. In: *Harrison's Principles of Internal Medicine* (16th edition). New York (US): McGraw-Hill; 2005. pp. 1960-1967).

Symptoms of SLE vary from person to person, and may come and go. In most patients, the symptoms include joint pain and swelling. Frequently affected joints are the fingers, hands, wrists, and knees. Some patients develop arthritis. Other common symptoms include: chest pain when taking a deep breath, fatigue, fever with no other cause, general discomfort, uneasiness, or ill feeling (malaise), hair loss, mouth sores, swollen lymph nodes, sensitivity to sunlight, skin rash—a "butterfly" rash over the cheeks and bridge of the nose affects about half of people with SLE, in some patients, the rash gets worse in sunlight, and the rash may also be widespread.

Other symptoms depend on what part of the body is affected, and may include the following:
Brain and nervous system: headaches, numbness, tingling, seizures, vision problems, personality changes,
Digestive tract: abdominal pain, nausea, and vomiting,
Heart: abnormal heart rhythms (arrhythmias),
Lung: coughing up blood and difficulty breathing, and
Skin: patchy skin color, fingers that change color when cold (Raynaud's phenomenon).

In one embodiment, only skin symptoms are manifested in SLE, i.e., discoid lupus. In one embodiment, SLE is skin predominant SLE.

In one embodiment, provided herein are methods of treating moderate, severe, or very severe SLE. The term "severe SLE" as used herein refers to an SLE condition where the patient has one or more severe or life-threatening symptoms (such as hemolytic anemia, extensive heart or lung involvement, kidney disease, or central nervous system involvement).

Further provided herein are methods for achieving one or more clinical endpoints associated with SLE comprising administering an effective amount of Compound I, or a pharmaceutically acceptable salt, solvate, hydrate, stereoisomer, tautomer or racemic mixtures thereof, to a patient in need thereof.

Further provided herein are methods for increasing the overall survival, objective response rate, time to progression, progression-free survival and/or time-to-treatment failure of a patient having SLE comprising administering an effective amount of Compound I, or a pharmaceutically acceptable salt, solvate, hydrate, stereoisomer, tautomer or racemic mixtures thereof, to the patient.

The dose of Compound I, or a pharmaceutically acceptable salt, solvate, hydrate, stereoisomer, tautomer or racemic mixtures thereof, to be administered to a patient can be variable and subject to the judgment of a health-care practitioner. Doses of Compound I, or a pharmaceutically acceptable salt, solvate, hydrate, stereoisomer, tautomer or racemic mixtures thereof, vary depending on factors such as: specific indication or symptoms to be treated, prevented, or managed; age and condition of a patient; and amount of second active agent used, if any. In general, Compound I, or a pharmaceutically acceptable salt, solvate, hydrate, stereoisomer, tautomer or racemic mixtures thereof, can be administered one to four or more times a day in a dose of about 0.005 mg/kg of a patient's body weight to about 10 mg/kg of a patient's body weight in a patient, but the above dosage may be properly varied depending on the age, body weight and medical condition of the patient and the type of administration. In one embodiment, the dose is about 0.01 mg/kg of a patient's body weight to about 5 mg/kg of a patient's body weight, about 0.05 mg/kg of a patient's body weight to about 1 mg/kg of a patient's body weight, about 0.1 mg/kg of a patient's body weight to about 0.75 mg/kg of a patient's body weight or about 0.25 mg/kg of a patient's body weight to about 0.5 mg/kg of a patient's body weight.

In one embodiment, one dose is given per day. In any given case, the amount of Compound I or a pharmaceutically acceptable salt, solvate, hydrate, stereoisomer, tautomer or racemic mixtures thereof administered will depend on such factors as the solubility of the active component, the formulation used and the route of administration. In one embodiment, application of a topical concentration provides intracellular exposures or concentrations of about 0.01-10 µM.

In certain embodiments, Compound I or a pharmaceutically acceptable salt, solvate, hydrate, stereoisomer, tautomer or racemic mixtures thereof is used in an amount of from about 0.1 mg to about 1000 mg per day, and can be adjusted in a conventional fashion (e.g., the same amount administered each day of the treatment, prevention or management period), in cycles (e.g., one week on, one week off), or in an amount that increases or decreases over the course of treatment, prevention, or management. In other embodiments, the dose can be from about 1 mg to about 300 mg, from about 0.1 mg to about 150 mg, from about 1 mg to about 200 mg, from about 10 mg to about 100 mg, from about 0.1 mg to about 50 mg, from about 1 mg to about 50 mg, from about 10 mg to about 50 mg, from about 20 mg to about 30 mg, or from about 1 mg to about 20 mg. In other embodiments, the dose can be from about 0.1 mg to about 100 mg, from about 0.1 mg to about 50 mg, from about 0.1 mg to about 25 mg, from about 0.1 mg to about 20 mg, from about 0.1 mg to about 15 mg, from about 0.1 mg to about 10 mg, from about 0.1 mg to about 7.5 mg, from about 0.1 mg to about 5 mg, from about 0.1 mg to about 4 mg, from about 0.1 mg to about 3 mg, from about 0.1 mg to about 2 mg, or from about 1 mg to about 1 mg.

In some embodiments, Compound 1A, or a pharmaceutically acceptable salt or solvate thereof, is administered. In one embodiment, the dose of Compound 1A, or a pharmaceutically acceptable salt or solvate thereof, is 0.3 mg given every other day. In one embodiment, the dose of Compound 1A, or a pharmaceutically acceptable salt or solvate thereof, is 0.3 mg given everyday. In one embodiment, the dose of Compound 1A, or a pharmaceutically acceptable salt or solvate thereof, is 0.6 mg and 0.3 mg given on alternating days. In one embodiment, the dose of Compound 1A, or a pharmaceutically acceptable salt or solvate thereof, is 0.6 mg given everyday.

In some embodiment, patients are started on high dose treatment, and if significant adverse effects persist, doses are adjusted, i.e., lowered, accordingly. For example, patients may start on a dose of 0.6 mg given everyday of Compound 1A, or a pharmaceutically acceptable salt or solvate thereon, and if significant adverse effects persist, then may adjust the dose in a step-wise fashion to 0.6 mg and 0.3 mg given on alternating days, then to 0.3 mg given everyday, and to 0.3 mg given every other day.

Compound I, or a pharmaceutically acceptable salt, solvate, hydrate, stereoisomer, tautomer or racemic mixtures thereof, can be combined with other pharmacologically active compounds ("second active agents") in methods and compositions provided herein. Certain combinations may work synergistically in the treatment of SLE, and conditions and symptoms associated with SLE. Compound I, or a pharmaceutically acceptable salt, solvate, hydrate, stereoisomer, tautomer or racemic mixtures thereof, can also work to alleviate adverse effects associated with certain second active agents, and vice versa.

One or more second active ingredients or agents can be used in the methods and compositions provided herein. Second active agents can be large molecules (e.g., proteins) or small molecules (e.g., synthetic inorganic, organometallic, or organic molecules).

In another embodiment, the method of treatment provided herein comprises the administration of a second therapeutic agent, wherein the second therapeutic agent is an anti-inflammatory drug, e.g., a steroidal anti-inflammatory drug, or a non-steroidal anti-inflammatory drug (NSAID), acetaminophen, naproxen, ibuprofen, acetylsalicylic acid, and the like. In a more specific embodiment in which an NSAID is administered, a proton pump inhibitor (PPI), e.g., omeprazole may also administered. In one embodiment, the antiinflammatory agent is a corticosteroid. In another embodiment, the antiinflammatory agent is colchicine.

In another embodiment, the second therapeutic agent is an immunomodulatory compound or an immunosuppressant compound such as azathioprine (Imuran™, Azasan™), methotrexate (Rheumatrex™, Trexall™), penicillamine (Depen™, Cuprimine™), cyclophosphamide (Cytoxan™), mycophenalate (CellCept™, Myfortic™), bosentan (Tracleer®), prednisone (Deltasone™, Liquid Pred™), and a PDE5 inhibitor. In another embodiment, where the affected individual has digital ulcerations and pulmonary hypertension, a vasodilator such as prostacyclin (iloprost) may be administered.

In another embodiment, the second therapeutic agent is an HDAC inhibitor, such as romidepsin, vorinostat, panobinostat, valproic acid, or belinostat; or a biological agent, such as an interleukin, an immunomodulatory monoclonal antibody, or bacillus Calmette-Guérin (BCG).

In another embodiment, the second therapeutic agent is an inhibitor of ActRII receptors or an activin-ActRII inhibitor. Inhibitors of ActRII receptors include ActRIIA inhibitors and ActRIIB inhibitors. Inhibitors of ActRII receptors can be polypeptides comprising activin-binding domains of ActRII. In certain embodiments, the activin-binding domain comprising polypeptides are linked to an Fc portion of an antibody (i.e., a conjugate comprising an activin-binding domain comprising polypeptide of an ActRII receptor and an Fc portion of an antibody is generated). In certain embodiments, the activin-binding domain is linked to an Fc portion of an antibody via a linker, e.g., a peptide linker.

Examples of non-antibody proteins selected for activin or ActRIIA binding and methods for design and selection of the same are found in WO/2002/088171, WO/2006/055689, WO/2002/032925, WO/2005/037989, US 2003/0133939, and US 2005/0238646, each of which is incorporated herein by reference in its entirety.

In one embodiment, the inhibitor of ActRII receptors is ACE-11. In another embodiment, the inhibitor of ActRII receptors is ACE-536.

In another embodiment, the second therapeutic agent is an agent that is conventionally used to treat SLE. Examples of such agents include, but are not limited to, an NSAID, a corticosteroid, a non-biologic disease modifying anti-rheumatic drug (DMARD), and a biological DMARD therapy (e.g., belimumab and rituximab).

Any combination of the above therapeutic agents, suitable for treatment of SLE or symptoms thereof, can be administered. Such therapeutic agents can be administered in any combination with Compound I, or a pharmaceutically acceptable salt, solvate, hydrate, stereoisomer, tautomer or racemic mixtures thereof, at the same time or as a separate course of treatment.

In certain embodiments, Compound I, or a pharmaceutically acceptable salt, solvate, hydrate, stereoisomer, tautomer or racemic mixtures thereof, is cyclically administered to a patient. Cycling therapy involves the administration of an active agent for a period of time, followed by a rest (i.e., discontinuation of the administration) for a period of time, and repeating this sequential administration. Cycling therapy can reduce the development of resistance to one or more of the therapies, avoid or reduce the side effects of one of the therapies, and/or improve the efficacy of the treatment.

Consequently, in one embodiment, a compound provided herein is administered daily in a single or divided doses in a four to six week cycle with a rest period of about a week or two weeks. Cycling therapy further allows the frequency, number, and length of dosing cycles to be increased. Thus, another embodiment encompasses the administration of a compound provided herein for more cycles than are typical when it is administered alone. In yet another embodiment, a compound provided herein is administered for a greater number of cycles than would typically cause dose-limiting toxicity in a patient to whom a second active ingredient is not also being administered.

In one embodiment, a compound provided herein is administered daily and continuously for three or four weeks at a dose of from about 0.03 mg to about 10 mg per day, followed by a rest of one or two weeks. In other embodiments, the dose can be from about 0.1 mg to about 8 mg, from about 0.3 mg to about 6 mg, from about 1 mg to about 4 mg, or about 2 mg, followed by a rest.

In one embodiment, a compound provided herein and a second active ingredient are administered orally, with administration of the compound provided herein occurring 30 to 60 minutes prior to the second active ingredient, during a cycle of four to six weeks. In another embodiment, the combination of a compound provided herein and a second active ingredient is administered by intravenous infusion over about 90 minutes every cycle.

Typically, the number of cycles during which the combination treatment is administered to a patient will be from about one to about 24 cycles, from about two to about 16 cycles, or from about four to about three cycles.

5.3. Methods of Detecting and Quantifying Biomarkers

In certain embodiments, provided herein are methods of detecting and quantifying the protein level of biomarker from a biological sample, comprising contacting proteins within the sample with a first antibody that immunospecifically binds to the biomarker protein. In some embodiments, the methods provided herein further comprise (i) contacting the biomarker protein bound to the first antibody with a second antibody with a detectable label, wherein the second antibody immunospecifically binds to the biomarker protein, and wherein the second antibody immunospecifically binds to a different epitope on the biomarker protein than the first antibody; (ii) detecting the presence of the second antibody bound to the biomarker protein; and (iii) determining the amount of the biomarker protein based on the amount of detectable label in the second antibody. In other embodiments, the methods provided herein further comprise (i) contacting the biomarker protein bound to the first antibody with a second antibody with a detectable label, wherein the second antibody immunospecifically binds to the first antibody; (ii) detecting the presence of the second antibody bound to the first antibody; and (iii) determining the amount of the biomarker protein based on the amount of detectable label in the second antibody.

In certain embodiments, provided herein are methods of detecting and quantifying the RNA (e.g., mRNA) level of a biomarker from a biological sample, comprising: (a) obtaining RNA from the sample; (b) contacting the RNA with a primer that specifically binds to a sequence in the RNA to generate a first DNA molecule having a sequence complementary to said RNA; (c) amplifying the DNA corresponding to a segment of a gene encoding the biomarker; and (d) determining the RNA level of the biomarker based on the amount of the amplified DNA.

In certain embodiments of the various methods provided herein, the two or more of the steps are performed sequentially. In other embodiments of the methods provided herein, two or more of the steps are performed in parallel (e.g., at the same time).

5.3.1 Methods of Determining mRNA Levels in a Sample

Several methods of detecting or quantitating mRNA levels are known in the art. Exemplary methods include, but are not limited to, northern blots, ribonuclease protection assays, PCR-based methods, and the like. The mRNA sequence of a biomarker can be used to prepare a probe that is at least partially complementary to the mRNA sequence. The probe can then be used to detect the mRNA in a sample, using any suitable assay, such as PCR-based methods, northern blotting, a dipstick assay, and the like.

In other embodiments, a nucleic acid assay for testing for compound activity in a biological sample can be prepared. An assay typically contains a solid support and at least one nucleic acid contacting the support, where the nucleic acid corresponds to at least a portion of an mRNA that has altered expression during a compound treatment in a patient, such as the mRNA of a biomarker. The assay can also have a means for detecting the altered expression of the mRNA in the sample.

The assay method can be varied depending on the type of mRNA information desired. Exemplary methods include but are not limited to Northern blots and PCR-based methods (e.g., qRT-PCR). Methods such as qRT-PCR can also accurately quantitate the amount of the mRNA in a sample.

Any suitable assay platform can be used to determine the presence of mRNA in a sample. For example, an assay may be in the form of a dipstick, a membrane, a chip, a disk, a test strip, a filter, a microsphere, a slide, a multi-well plate, or an optical fiber. An assay system may have a solid support on which a nucleic acid corresponding to the mRNA is attached. The solid support may comprise, for example, a plastic, silicon, a metal, a resin, glass, a membrane, a particle, a precipitate, a gel, a polymer, a sheet, a sphere, a polysaccharide, a capillary, a film, a plate, or a slide. The assay components can be prepared and packaged together as a kit for detecting an mRNA.

The nucleic acid can be labeled, if desired, to make a population of labeled mRNAs. In general, a sample can be labeled using methods that are well known in the art (e.g., using DNA ligase, terminal transferase, or by labeling the RNA backbone, etc.). See, e.g., Ausubel et al., *Short Protocols in Molecular Biology* (Wiley & Sons, 3rd ed. 1995); Sambrook et al., *Molecular Cloning: A Laboratory Manual* (Cold Spring Harbor, N.Y., 3rd ed. 2001). In some embodiments, the sample is labeled with fluorescent label. Exemplary fluorescent dyes include, but are not limited to, xanthene dyes, fluorescein dyes (e.g., fluorescein isothiocyanate (FITC), 6-carboxyfluorescein (FAM), 6 carboxy-2',4',7',4,7-hexachlorofluorescein (HEX), 6-carboxy-4',5'-dichloro-2',7'-dimethoxyfluorescein (JOE)), rhodamine dyes (e.g., rhodamine 110 (R110), N,N,N',N'-tetramethyl-6-carboxyrhodamine (TAMRA), 6-carboxy-X-rhodamine (ROX), 5-carboxyrhodamine 6G (R6G5 or G5), 6-carboxyrhodamine 6G (R6G6 or G6)), cyanine dyes (e.g., Cy3, Cy5 and Cy7), Alexa dyes (e.g., Alexa-fluor-555), coumarin, Diethylaminocoumarin, umbelliferone, benzimide dyes (e.g., Hoechst 33258), phenanthridine dyes (e.g., Texas Red), ethidium dyes, acridine dyes, carbazole dyes, phenoxazine dyes, porphyrin dyes, polymethine dyes, BODIPY dyes, quinoline dyes, Pyrene, Fluorescein Chlorotriazinyl, eosin dyes, Tetramethylrhodamine, Lissamine, Napthofluorescein, and the like.

The nucleic acids may be present in specific, addressable locations on a solid support, each corresponding to at least a portion of mRNA sequences that are differentially expressed upon treatment of a compound in a cell or a patient.

A typical mRNA assay method can contain the steps of 1) obtaining surface-bound subject probes; 2) hybridizing a population of mRNAs to the surface-bound probes under conditions sufficient to provide for specific binding; (3) post-hybridization washing to remove nucleic acids not specifically bound to the surface-bound probes; and (4) detecting the hybridized mRNAs. The reagents used in each of these steps and their conditions for use may vary depending on the particular application.

Hybridization can be carried out under suitable hybridization conditions, which may vary in stringency as desired. Typical conditions are sufficient to produce probe/target complexes on a solid surface between complementary binding members, i.e., between surface-bound subject probes and complementary mRNAs in a sample. In certain embodiments, stringent hybridization conditions may be employed.

Hybridization is typically performed under stringent hybridization conditions. Standard hybridization techniques (e.g., under conditions sufficient to provide for specific binding of target mRNAs in the sample to the probes) are described in Kallioniemi et al., *Science* 1992, 258:818-821 and International Patent Application Publication No. WO 93/18186. Several guides to general techniques are available, e.g., Tijssen, *Hybridization with Nucleic Acid Probes*, Parts I and II (Elsevier, Amsterdam 1993). For descriptions of techniques suitable for in situ hybridizations, see Gall et al., *Meth. Enzymol.* 1981, 21:470-480; Angerer et al., *Genetic Engineering: Principles and Methods*, Vol 7, pgs 43-65 (Plenum Press, New York, Setlow and Hollaender, eds. 1985). Selection of appropriate conditions, including temperature, salt concentration, polynucleotide concentration, hybridization time, stringency of washing conditions, and the like will depend on experimental design, including source of sample, identity of capture agents, degree of complementarity expected, etc., and may be determined as a matter of routine experimentation for those of ordinary skill in the art.

Those of ordinary skill will readily recognize that alternative but comparable hybridization and wash conditions can be utilized to provide conditions of similar stringency.

After the mRNA hybridization procedure, the surface bound polynucleotides are typically washed to remove unbound nucleic acids. Washing may be performed using any convenient washing protocol, where the washing conditions are typically stringent, as described above. The hybridization of the target mRNAs to the probes is then detected using standard techniques.

Other methods, such as PCR-based methods, can also be used to detect the expression of CRBN or a protein that is directly or indirectly affected by CRBN. Examples of PCR methods can be found in U.S. Pat. No. 6,927,024, which is incorporated by reference herein in its entirety. Examples of RT-PCR methods can be found in U.S. Pat. No. 7,122,799, which is incorporated by reference herein in its entirety. A method of fluorescent in situ PCR is described in U.S. Pat. No. 7,186,507, which is incorporated by reference herein in its entirety.

In some embodiments, quantitative Reverse Transcription-PCR (qRT-PCR) can be used for both the detection and quantification of RNA targets (Bustin et al., *Clin. Sci.* 2005, 109:365-379). Quantitative results obtained by qRT-PCR are generally more informative than qualitative data. Thus, in some embodiments, qRT-PCR-based assays can be useful to measure mRNA levels during cell-based assays. The qRT-PCR method is also useful to monitor patient therapy. Examples of qRT-PCR-based methods can be found, for example, in U.S. Pat. No. 7,101,663, which is incorporated by reference herein in its entirety.

In contrast to regular reverse transcriptase-PCR and analysis by agarose gels, qRT-PCR gives quantitative results. An additional advantage of qRT-PCR is the relative ease and convenience of use. Instruments for qRT-PCR, such as the Applied Biosystems 7500, are available commercially, so are the reagents, such as TaqMan® Sequence Detection Chemistry. For example, TaqMan® Gene Expression Assays can be used, following the manufacturer's instructions. These kits are pre-formulated gene expression assays for rapid, reliable detection and quantification of human, mouse, and rat mRNA transcripts. An exemplary qRT-PCR program, for example, is 50° C. for 2 minutes, 95° C. for 10 minutes, 40 cycles of 95° C. for 15 seconds, then 60° C. for 1 minute.

To determine the cycle number at which the fluorescence signal associated with a particular amplicon accumulation crosses the threshold (referred to as the $C_T$), the data can be analyzed, for example, using 7500 Real-Time PCR System Sequence Detection software vs. using the comparative $C_T$ relative quantification calculation method. Using this method, the output is expressed as a fold-change of expression levels. In some embodiments, the threshold level can be selected to be automatically determined by the software. In some embodiments, the threshold level is set to be above the baseline but sufficiently low to be within the exponential growth region of an amplification curve.

5.3.2 Methods of Determining Polypeptide or Protein Levels in a Sample

Several protein detection and quantization methods can be used to measure the level of a biomarker. Any suitable protein quantization method can be used. In some embodiments, antibody-based methods are used. Exemplary methods that can be used include, but are not limited to, immunoblotting (Western blot), ELISA, immunohistochemistry, flow cytometry, cytometry bead array, mass spectroscopy, and the like. Several types of ELISA are commonly used, including direct ELISA, indirect ELISA, and sandwich ELISA.

5.4. Subjects, Samples, and Types of Cells

In certain embodiments, the various methods provided herein use samples (e.g., biological samples) from subjects or individuals (e.g., patients). The subject can be a patient, such as, a patient with a SLE. The subject can be a mammal, for example, a human. The subject can be male or female, and can be an adult, a child, or an infant. Samples can be analyzed at a time during an active phase of SLE, or when the SLE is inactive. In certain embodiments, more than one sample from a subject can be obtained.

In certain embodiments, the sample used in the methods provided herein comprises body fluids from a subject. Non-limiting examples of body fluids include blood (e.g., whole blood), blood plasma, amniotic fluid, aqueous humor, bile, cerumen, cowper's fluid, pre-ejaculatory fluid, chyle, chyme, female ejaculate, interstitial fluid, lymph, menses, breast milk, mucus, pleural fluid, pus, saliva, sebum, semen, serum, sweat, tears, urine, vaginal lubrication, vomit, water, feces, internal body fluids (including cerebrospinal fluid surrounding the brain and the spinal cord), synovial fluid, intracellular fluid (the fluid inside cells), and vitreous humour (the fluid in the eyeball). In some embodiments, the sample is a blood sample. The blood sample can be obtained using conventional techniques as described in, e.g., Innis et al, eds., *PCR Protocols* (Academic Press, 1990). White blood cells can be separated from blood samples using conventional techniques or commercially available kits, e.g., RosetteSep kit (Stein Cell Technologies, Vancouver, Canada). Sub-populations of white blood cells, e.g., mononuclear cells, B cells, T cells, monocytes, granulocytes, or lymphocytes, can be further isolated using conventional techniques, e.g., magnetically activated cell sorting (MACS) (Miltenyi Biotec, Auburn, California) or fluorescently activated cell sorting (FACS) (Becton Dickinson, San Jose, California).

In one embodiment, the blood sample is from about 0.1 mL to about 10.0 mL, from about 0.2 mL to about 7 mL, from about 0.3 mL to about 5 mL, from about 0.4 mL to about 3.5 mL, or from about 0.5 mL to about 3 mL. In another embodiment, the blood sample is about 0.3, about 0.4, about 0.5, about 0.6, about 0.7, about 0.8, about 0.9, about 1.0, about 1.5, about 2.0, about 2.5, about 3.0, about 3.5, about 4.0, about 4.5, about 5.0, about 6.0, about 7.0, about 8.0, about 9.0, or about 10.0 mL.

In some embodiments, the sample used in the present methods comprises a biopsy (e.g., a tumor biopsy). The biopsy can be from any organ or tissue, for example, skin, liver, lung, heart, colon, kidney, bone marrow, teeth, lymph node, hair, spleen, brain, breast, or other organs. Any biopsy technique known by those skilled in the art can be used for isolating a sample from a subject, for instance, open biopsy, close biopsy, core biopsy, incisional biopsy, excisional biopsy, or fine needle aspiration biopsy.

In one embodiment, the sample used in the methods provided herein is obtained from the subject prior to the subject receiving a treatment for the disease or disorder. In another embodiment, the sample is obtained from the subject during the subject receiving a treatment for the disease or disorder. In another embodiment, the sample is obtained from the subject after the subject receiving a treatment for the disease or disorder. In various embodiments, the treatment comprises administering a compound (e.g., a compound provided in Section 5.5 below) to the subject.

In certain embodiments, the sample used in the methods provided herein comprises a plurality of cells. In certain embodiments, the number of cells used in the methods provided herein can range from a single cell to about $10^9$ cells. In some embodiments, the number of cells used in the methods provided herein is about $1 \times 10^4$, about $5 \times 10^4$, about $1 \times 10^5$, about $5 \times 10^5$, about $1 \times 10^6$, about $5 \times 10^6$, about $1 \times 10^7$, about $5 \times 10^7$, about $1 \times 10^8$, about $5 \times 10^8$, or about $1 \times 10^9$.

The number and type of cells collected from a subject can be monitored, for example, by measuring changes in cell surface markers using standard cell detection techniques such as flow cytometry, cell sorting, immunocytochemistry (e.g., staining with tissue specific or cell-marker specific antibodies), fluorescence activated cell sorting (FACS), magnetic activated cell sorting (MACS), by examining the morphology of cells using light or confocal microscopy, and/or by measuring changes in gene expression using techniques well known in the art, such as PCR and gene expression profiling. These techniques can be used, too, to identify cells that are positive for one or more particular markers.

In certain embodiments, subsets of cells are used in the methods provided herein. Methods of sorting and isolating specific populations of cells are well-known in the art and can be based on cell size, morphology, or intracellular or extracellular markers. Such methods include, but are not limited to, flow cytometry, flow sorting, FACS, bead based separation such as magnetic cell sorting, size-based separation (e.g., a sieve, an array of obstacles, or a filter), sorting in a microfluidics device, antibody-based separation, sedimentation, affinity adsorption, affinity extraction, density gradient centrifugation, laser capture microdissection, etc. Fluorescence activated cell sorting (FACS) is a well-known method for separating particles, including cells, based on the fluorescent properties of the particles (Kamarch, *Methods Enzymol.* 1987, 151:150-165). Laser excitation of fluorescent moieties in the individual particles results in a small electrical charge allowing electromagnetic separation of positive and negative particles from a mixture. In one embodiment, cell surface marker-specific antibodies or ligands are labeled with distinct fluorescent labels. Cells are processed through the cell sorter, allowing separation of cells based on their ability to bind to the antibodies used. FACS sorted particles may be directly deposited into individual wells of 96-well or 384-well plates to facilitate separation and cloning.

In one embodiment, RNA (e.g., mRNA) or protein is purified from a tumor, and the presence or absence of a biomarker is measured by gene or protein expression analysis. In certain embodiments, the presence or absence of a biomarker is measured by quantitative real-time PCR (qRT-PCR), microarray, flow cytometry, or immunofluorescence. In other embodiments, the presence or absence of a biomarker is measured by ELISA or other similar methods known in the art.

5.5 Compounds

In certain embodiments, Compound I for use in the methods provided herein, including the combination therapy, and in compositions provided herein is a compound of formula:

Compound I

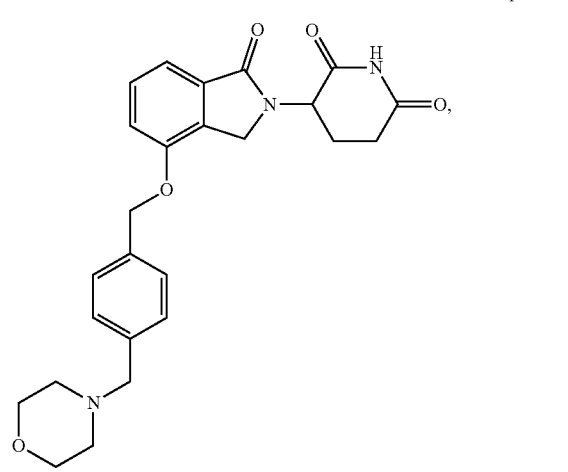

or a pharmaceutically acceptable salt, solvate, hydrate, stereoisomer, tautomer or racemic mixtures thereof.

In one embodiment, the compound is (S)-3-[4-(4-morpholin-4-ylmethyl-benzyloxy)-1-oxo-1,3-dihydro-isoindol-2-yl]-piperidine-2,6-dione, having the following structure:

Compound IA

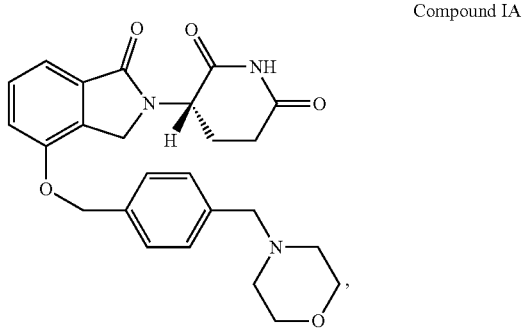 [SMILES: O=C1CC[C@H](N2Cc3c(OCc4ccc(CN5CCOCC5)cc4)cccc3C2=O)C(=O)N1]

or a pharmaceutically acceptable salt, solvate, hydrate, or tautomer thereof.

In one embodiment, the compound is (S)-3-[4-(4-morpholin-4-ylmethyl-benzyloxy)-1-oxo-1,3-dihydro-isoindol-2-yl]-piperidine-2,6-dione.

In one embodiment, the compound is a pharmaceutically acceptable salt of (S)-3-[4-(4-morpholin-4-ylmethyl-benzyloxy)-1-oxo-1,3-dihydro-isoindol-2-yl]-piperidine-2,6-dione.

In one embodiment, the compound is (S)-3-[4-(4-morpholin-4-ylmethyl-benzyloxy)-1-oxo-1,3-dihydro-isoindol-2-yl]-piperidine-2,6-dione hydrochloride.

In one embodiment, the compound is (R)-3-[4-(4-morpholin-4-ylmethyl-benzyloxy)-1-oxo-1,3-dihydro-isoindol-2-yl]-piperidine-2,6-dione, having the following structure:

Compound IB

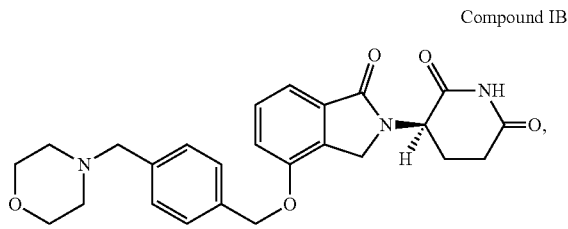 [SMILES: O=C1CC[C@@H](N2Cc3c(OCc4ccc(CN5CCOCC5)cc4)cccc3C2=O)C(=O)N1]

or a pharmaceutically acceptable salt, solvate, hydrate, or tautomer thereof.

In one embodiment, the compound is (R)-3-[4-(4-morpholin-4-ylmethyl-benzyloxy)-1-oxo-1,3-dihydro-isoindol-2-yl]-piperidine-2,6-dione.

In one embodiment, the compound is a pharmaceutically acceptable salt of (R)-3-[4-(4-morpholin-4-ylmethyl-benzyloxy)-1-oxo-1,3-dihydro-isoindol-2-yl]-piperidine-2,6-dione.

In one embodiment, the compound is selected from 3-[4-(4-morpholin-4-ylmethyl-benzyloxy)-1-oxo-1,3-dihydro-isoindol-2-yl]-piperidine-2,6-dione, 3-[4-(4-morpholin-4-ylmethylbenzyloxy)-1-oxo-1,3-dihydro-isoindo-2-yl]piperidine-2,6-dione hydrochloride, (R)-3-[4-(4-morpholin-4-ylmethylbenzyloxy)-1-oxo-1,3-dihydro-isoindo-2-yl]piperidine-2,6-dione, (R)-3-[4-(4-morpholin-4-ylmethylbenzyloxy)-1-oxo-1,3-dihydro-isoindo-2-yl]piperidine-2,6-dione hydrochloride, (S)-3-[4-(4-morpholin-4-ylmethylbenzyloxy)-1-oxo-1,3-dihydro-isoindo-2-yl]piperidine-2,6-dione and (S)-3-[4-(4-morpholin-4-ylmethylbenzyloxy)-1-oxo-1,3-dihydro-isoindo-2-yl]piperidine-2,6-dione hydrochloride.

Compound I, or a pharmaceutically acceptable salt, solvate, hydrate, stereoisomer, tautomer or racemic mixtures thereof, can be prepared by methods known to one of skill in the art, for example, according to the procedure described in US Publication No. 2011/0196150, the entirety of which is incorporated herein by reference.

An exemplary method for preparation is described in Example 1.

The various compounds provided herein contain one or more chiral centers, and can exist as mixtures of enantiomers (e.g., racemic mixtures) or mixtures of diastereomers. The methods provided herein encompass the use of stereomerically pure forms of such compounds as well as mixtures of those forms. For example, mixtures comprising equal or unequal amounts of the enantiomers of a particular compound may be used in methods provided herein. These isomers may be asymmetrically synthesized or resolved using standard techniques, such as chiral columns or chiral resolving agents. See, Jacques et al., *Enantiomers, Racemates and Resolutions* (Wiley-Interscience, New York, 1981); Wilen et al., *Tetrahedron* 1977, 33:2725-2736; Eliel, *Stereochemistry of Carbon Compounds* (McGraw-Hill, NY, 1962); Wilen, *Tables of Resolving Agents and Optical Resolutions*, p. 268 (Eliel, ed., Univ. of Notre Dame Press, Notre Dame, Ind., 1972).

Also provided herein are isotopically enriched analogs of the compounds provided herein. Isotopic enrichment (for example, deuteration) of pharmaceuticals to improve pharmacokinetics ("PK"), pharmacodynamics ("PD"), and toxicity profiles, has been demonstrated previously with some classes of drugs. See, for example, Lijinsky et. al., *Food Cosmet. Toxicol.*, 20: 393 (1982); Lijinsky et. al., *J. Nat. Cancer Inst.*, 69: 1127 (1982); Mangold et. al., *Mutation Res.* 308: 33 (1994); Gordon et. al., *Drug Metab. Dispos.*, 15: 589 (1987); Zello et. al., *Metabolism*, 43: 487 (1994); Gately et. al., *J. Nucl. Med.*, 27: 388 (1986); Wade D, *Chem. Biol. Interact.* 117: 191 (1999).

Without being limited by any particular theory, isotopic enrichment of a drug can be used, for example, to (1) reduce or eliminate unwanted metabolites, (2) increase the half-life of the parent drug, (3) decrease the number of doses needed to achieve a desired effect, (4) decrease the amount of a dose necessary to achieve a desired effect, (5) increase the formation of active metabolites, if any are formed, and/or (6) decrease the production of deleterious metabolites in specific tissues and/or create a more effective drug and/or a safer drug for combination therapy, whether the combination therapy is intentional or not.

Replacement of an atom for one of its isotopes often will result in a change in the reaction rate of a chemical reaction. This phenomenon is known as the Kinetic Isotope Effect ("KIE"). For example, if a C—H bond is broken during a rate-determining step in a chemical reaction (i.e. the step with the highest transition state energy), substitution of a deuterium for that hydrogen will cause a decrease in the reaction rate and the process will slow down. This phenomenon is known as the Deuterium Kinetic Isotope Effect ("DKIE"). (See, e.g., Foster et al., Adv. Drug Res., vol. 14, pp. 1-36 (1985); Kushner et al., Can. J. Physiol. Pharmacol., vol. 77, pp. 79-88 (1999)).

The magnitude of the DKIE can be expressed as the ratio between the rates of a given reaction in which a C—H bond is broken, and the same reaction where deuterium is substituted for hydrogen. The DKIE can range from about 1 (no isotope effect) to very large numbers, such as 50 or more, meaning that the reaction can be fifty, or more, times slower when deuterium is substituted for hydrogen. Without being limited by a particular theory, high DKIE values may be due in part to a phenomenon known as tunneling, which is a consequence of the uncertainty principle. Tunneling is ascribed to the small mass of a hydrogen atom, and occurs because transition states involving a proton can sometimes form in the absence of the required activation energy. Because deuterium has more mass than hydrogen, it statistically has a much lower probability of undergoing this phenomenon.

Tritium ("T") is a radioactive isotope of hydrogen, used in research, fusion reactors, neutron generators and radiopharmaceuticals. Tritium is a hydrogen atom that has 2 neutrons in the nucleus and has an atomic weight close to 3. It occurs naturally in the environment in very low concentrations, most commonly found as $T_2O$. Tritium decays slowly (half-life=12.3 years) and emits a low energy beta particle that cannot penetrate the outer layer of human skin. Internal exposure is the main hazard associated with this isotope, yet it must be ingested in large amounts to pose a significant health risk. As compared with deuterium, a lesser amount of tritium must be consumed before it reaches a hazardous level. Substitution of tritium ("T") for hydrogen results in yet a stronger bond than deuterium and gives numerically larger isotope effects.

Similarly, substitution of isotopes for other elements, including, but not limited to, $^{13}C$ or $^{14}C$ for carbon, $^{33}S$, $^{34}S$, or $^{36}S$ for sulfur, $^{15}N$ for nitrogen, and $^{17}O$ or $^{18}O$ for oxygen, will provide a similar kinetic isotope effects.

Isotopic enrichment at certain positions of a compound provided herein may produce a detectable KIE that affects the pharmacokinetic, pharmacologic, and/or toxicological profiles of a compound provided herein in comparison with a similar compound having a natural isotopic composition. In one embodiment, the deuterium enrichment is performed on the site of C—H bond cleavage during metabolism.

5.6 Pharmaceutical Compositions

Pharmaceutical compositions can be used in the preparation of individual, single unit dosage forms. Pharmaceutical compositions and dosage forms provided herein comprise a compound provided herein, or a pharmaceutically acceptable salt, solvate, hydrate, stereoisomer, racemate, clathrate, or prodrug thereof. Pharmaceutical compositions and dosage forms can further comprise one or more excipients.

Pharmaceutical compositions and dosage forms provided herein can also comprise one or more additional active ingredients. Examples of optional second, or additional, active ingredients are disclosed above.

Single unit dosage forms provided herein are suitable for oral, mucosal (e.g., nasal, sublingual, vaginal, buccal, or rectal), parenteral (e.g., subcutaneous, intravenous, bolus injection, intramuscular, or intraarterial), topical (e.g., eye drops or other ophthalmic preparations), transdermal or transcutaneous administration to a patient. Examples of dosage forms include, but are not limited to: tablets; caplets; capsules, such as soft elastic gelatin capsules; cachets; troches; lozenges; dispersions; suppositories; powders; aerosols (e.g., nasal sprays or inhalers); gels; liquid dosage forms suitable for oral or mucosal administration to a patient, including suspensions (e.g., aqueous or non-aqueous liquid suspensions, oil-in-water emulsions, or a water-in-oil liquid emulsions), solutions, and elixirs; liquid dosage forms suitable for parenteral administration to a patient; eye drops or other ophthalmic preparations suitable for topical administration; and sterile solids (e.g., crystalline or amorphous solids) that can be reconstituted to provide liquid dosage forms suitable for parenteral administration to a patient.

The composition, shape, and type of dosage forms will typically vary depending on their use. For example, a dosage form used in the acute treatment of a disease may contain larger amounts of one or more of the active ingredients it comprises than a dosage form used in the chronic treatment of the same disease. Similarly, a parenteral dosage form may contain smaller amounts of one or more of the active ingredients it comprises than an oral dosage form used to treat the same disease. These and other ways in which specific dosage forms are used will vary from one another will be readily apparent to those skilled in the art. See, e.g., *Remington's Pharmaceutical Sciences*, 20$^{th}$ ed., Mack Publishing, Easton PA (2000).

In one embodiment, pharmaceutical compositions and dosage forms comprise one or more excipients. Suitable excipients are well known to those skilled in the art of pharmacy, and non-limiting examples of suitable excipients are provided herein. Whether a particular excipient is suitable for incorporation into a pharmaceutical composition or dosage form depends on a variety of factors well known in the art including, but not limited to, the way in which the dosage form will be administered to a patient. For example, oral dosage forms such as tablets may contain excipients not suited for use in parenteral dosage forms. The suitability of a particular excipient may also depend on the specific active ingredients in the dosage form. For example, the decomposition of some active ingredients may be accelerated by some excipients such as lactose, or when exposed to water. Active ingredients that comprise primary or secondary amines are particularly susceptible to such accelerated decomposition. Consequently, provided are pharmaceutical compositions and dosage forms that contain little, if any, lactose other mono- or di-saccharides. As used herein, the term "lactose-free" means that the amount of lactose present, if any, is insufficient to substantially increase the degradation rate of an active ingredient.

Lactose-free compositions can comprise excipients that are well known in the art and are listed, for example, in the *U.S. Pharmacopeia* (USP) 25-NF20 (2002). In general, lactose-free compositions comprise active ingredients, a binder/filler, and a lubricant in pharmaceutically compatible and pharmaceutically acceptable amounts. In one embodiment, lactose-free dosage forms comprise active ingredients, microcrystalline cellulose, pre-gelatinized starch, and magnesium stearate.

Also provided are anhydrous pharmaceutical compositions and dosage forms comprising active ingredients, since water can facilitate the degradation of some compounds. For example, the addition of water (e.g., 5%) is widely accepted in the pharmaceutical arts as a means of simulating long-term storage in order to determine characteristics such as shelf-life or the stability of formulations over time. See, e.g., Jens T. Carstensen, *Drug Stability: Principles & Practice*, 2d. Ed., Marcel Dekker, NY, NY, 1995, pp. 379-80. In effect, water and heat accelerate the decomposition of some compounds. Thus, the effect of water on a formulation can be of great significance since moisture and/or humidity are commonly encountered during manufacture, handling, packaging, storage, shipment, and use of formulations.

Anhydrous pharmaceutical compositions and dosage forms can be prepared using anhydrous or low moisture containing ingredients and low moisture or low humidity conditions. Pharmaceutical compositions and dosage forms that comprise lactose and at least one active ingredient that comprises a primary or secondary amine are anhydrous if substantial contact with moisture and/or humidity during manufacturing, packaging, and/or storage is expected.

An anhydrous pharmaceutical composition should be prepared and stored such that its anhydrous nature is maintained. Accordingly, anhydrous compositions are, in one embodiment, packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

Also provided are pharmaceutical compositions and dosage forms that comprise one or more compounds that reduce the rate by which an active ingredient will decompose. Such compounds, which are referred to herein as "stabilizers," include, but are not limited to, antioxidants such as ascorbic acid, pH buffers, or salt buffers.

Like the amounts and types of excipients, the amounts and specific types of active ingredients in a dosage form may differ depending on factors such as, but not limited to, the route by which it is to be administered to patients. In one embodiment, dosage forms comprise a compound provided herein in an amount of from about 0.10 to about 500 mg. In other embodiments, dosage forms comprise a compound provided herein in an amount of about 0.1, 1, 2, 5, 7.5, 10, 12.5, 15, 17.5, 20, 25, 50, 100, 150, 200, 250, 300, 350, 400, 450, or 500 mg.

In other embodiments, dosage forms comprise the second active ingredient in an amount of 1 to about 1000 mg, from about 5 to about 500 mg, from about 10 to about 350 mg, or from about 50 to about 200 mg. Of course, the specific amount of the second active agent will depend on the specific agent used, the diseases or disorders being treated or managed, and the amount(s) of a compound provided herein, and any optional additional active agents concurrently administered to the patient.

Oral Dosage Forms

Pharmaceutical compositions that are suitable for oral administration can be provided as discrete dosage forms, such as, but not limited to, tablets (e.g., chewable tablets), caplets, capsules, and liquids (e.g., flavored syrups). Such dosage forms contain predetermined amounts of active ingredients, and may be prepared by methods of pharmacy well known to those skilled in the art. See generally, *Remington's Pharmaceutical Sciences,* 20th ed., Mack Publishing, Easton PA (2000).

Oral dosage forms provided herein are prepared by combining the active ingredients in an intimate admixture with at least one excipient according to conventional pharmaceutical compounding techniques. Excipients can take a wide variety of forms depending on the form of preparation desired for administration. For example, excipients suitable for use in oral liquid or aerosol dosage forms include, but are not limited to, water, glycols, oils, alcohols, flavoring agents, preservatives, and coloring agents. Examples of excipients suitable for use in solid oral dosage forms (e.g., powders, tablets, capsules, and caplets) include, but are not limited to, starches, sugars, micro-crystalline cellulose, diluents, granulating agents, lubricants, binders, and disintegrating agents.

In one embodiment, oral dosage forms are tablets or capsules, in which case solid excipients are employed. In another embodiment, tablets can be coated by standard aqueous or nonaqueous techniques. Such dosage forms can be prepared by any of the methods of pharmacy. In general, pharmaceutical compositions and dosage forms are prepared by uniformly and intimately admixing the active ingredients with liquid carriers, finely divided solid carriers, or both, and then shaping the product into the desired presentation if necessary.

For example, a tablet can be prepared by compression or molding. Compressed tablets can be prepared by compressing in a suitable machine the active ingredients in a free-flowing form such as powder or granules, optionally mixed with an excipient. Molded tablets can be made by molding in a suitable machine a mixture of the powdered compound moistened with an inert liquid diluent.

Examples of excipients that can be used in oral dosage forms provided herein include, but are not limited to, binders, fillers, disintegrants, and lubricants. Binders suitable for use in pharmaceutical compositions and dosage forms include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof.

Suitable forms of microcrystalline cellulose include, but are not limited to, the materials sold as AVICEL-PH-101, AVICEL-PH-103 AVICEL RC-581, AVICEL-PH-105 (available from FMC Corporation, American Viscose Division, Avicel Sales, Marcus Hook, PA), and mixtures thereof. An specific binder is a mixture of microcrystalline cellulose and sodium carboxymethyl cellulose sold as AVICEL RC-581. Suitable anhydrous or low moisture excipients or additives include AVICEL-PH-103™ and Starch 1500 LM.

Examples of fillers suitable for use in the pharmaceutical compositions and dosage forms provided herein include, but are not limited to, talc, calcium carbonate (e.g., granules or powder), microcrystalline cellulose, powdered cellulose, dextrates, kaolin, mannitol, silicic acid, sorbitol, starch, pre-gelatinized starch, and mixtures thereof. The binder or filler in pharmaceutical compositions is, in one embodiment, present in from about 50 to about 99 weight percent of the pharmaceutical composition or dosage form.

Disintegrants may be used in the compositions to provide tablets that disintegrate when exposed to an aqueous environment. Tablets that contain too much disintegrant may disintegrate in storage, while those that contain too little may not disintegrate at a desired rate or under the desired conditions. Thus, a sufficient amount of disintegrant that is neither too much nor too little to detrimentally alter the release of the active ingredients may be used to form solid oral dosage forms. The amount of disintegrant used varies based upon the type of formulation, and is readily discernible to those of ordinary skill in the art. In one embodiment, pharmaceutical compositions comprise from about 0.5 to about 15 weight percent of disintegrant, or from about 1 to about 5 weight percent of disintegrant.

Disintegrants that can be used in pharmaceutical compositions and dosage forms include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

Lubricants that can be used in pharmaceutical compositions and dosage forms include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laureate, agar, and mixtures thereof. Additional lubricants include, for example, a syloid silica gel (AEROSIL200, manufactured by W.R. Grace Co. of Baltimore, MD), a coagulated aerosol of synthetic silica (marketed by Degussa Co. of Plano, TX), CAB-O-SIL (a pyrogenic silicon dioxide product sold by Cabot Co. of Boston, MA), and mixtures thereof. If used at all, lubricants may be used in an amount of less than about 1 weight percent of the pharmaceutical compositions or dosage forms into which they are incorporated.

In one embodiment, a solid oral dosage form comprises a compound provided herein, anhydrous lactose, microcrystalline cellulose, polyvinylpyrrolidone, stearic acid, colloidal anhydrous silica, and gelatin.

Controlled Release Dosage Forms

Active ingredients such as the compounds provided herein can be administered by controlled release means or by delivery devices that are well known to those of ordinary skill in the art. Examples include, but are not limited to, those described in U.S. Pat. Nos. 3,845,770; 3,916,899; 3,536,809; 3,598,123; and 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; 6,699,500 each of which is incorporated herein by reference. Such dosage forms can be used to provide slow or controlled release of one or more active ingredients using, for example, hydropropylmethyl cellulose, other polymer matrices, gels, permeable membranes, osmotic systems, multilayer coatings, microparticles, liposomes, microspheres, or a combination thereof to provide the desired release profile in varying proportions. Suitable controlled release formulations known to those of ordinary skill in the art, including those described herein, can be readily selected for use with the active ingredients provided herein. Thus, the compositions provided encompass single unit dosage forms suitable for oral administration such as, but not limited to, tablets, capsules, gelcaps, and caplets that are adapted for controlled release.

All controlled release pharmaceutical products have a common goal of improving drug therapy over that achieved by their non controlled counterparts. Ideally, the use of an optimally designed controlled release preparation in medical treatment is characterized by a minimum of drug substance being employed to cure or control the condition in a minimum amount of time. Advantages of controlled release formulations include extended activity of the drug, reduced dosage frequency, and increased subject compliance. In addition, controlled release formulations can be used to affect the time of onset of action or other characteristics, such as blood levels of the drug, and can thus affect the occurrence of side (e.g., adverse) effects.

Most controlled release formulations are designed to initially release an amount of drug (active ingredient) that promptly produces the desired therapeutic effect, and gradually and continually release of other amounts of drug to maintain this level of therapeutic or prophylactic effect over an extended period of time. In order to maintain this constant level of drug in the body, the drug must be released from the dosage form at a rate that will replace the amount of drug being metabolized and excreted from the body. Controlled release of an active ingredient can be stimulated by various conditions including, but not limited to, pH, temperature, enzymes, water, or other physiological conditions or compounds.

In certain embodiments, the drug may be administered using intravenous infusion, an implantable osmotic pump, a transdermal patch, liposomes, or other modes of administration. In one embodiment, a pump may be used (see, Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used. In yet another embodiment, a controlled release system can be placed in a subject at an appropriate site determined by a practitioner of skill, i.e., thus requiring only a fraction of the systemic dose (see, e.g., Goodson, Medical Applications of Controlled Release, vol. 2, pp. 115-138 (1984)). Other controlled release systems are discussed in the review by Langer (*Science* 249:1527-1533 (1990)). The active ingredient can be dispersed in a solid inner matrix, e.g., polymethylmethacrylate, polybutylmethacrylate, plasticized or unplasticized polyvinylchloride, plasticized nylon, plasticized polyethyleneterephthalate, natural rubber, polyisoprene, polyisobutylene, polybutadiene, polyethylene, ethylene-vinylacetate copolymers, silicone rubbers, polydimethylsiloxanes, silicone carbonate copolymers, hydrophilic polymers such as hydrogels of esters of acrylic and methacrylic acid, collagen, cross-linked polyvinylalcohol and cross-linked partially hydrolyzed polyvinyl acetate, that is surrounded by an outer polymeric membrane, e.g., polyethylene, polypropylene, ethylene/propylene copolymers, ethylene/ethyl acrylate copolymers, ethylene/vinylacetate copolymers, silicone rubbers, polydimethyl siloxanes, neoprene rubber, chlorinated polyethylene, polyvinylchloride, vinylchloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, that is insoluble in body fluids. The active ingredient then diffuses through the outer polymeric membrane in a release rate controlling step. The percentage of active ingredient in such parenteral compositions is highly dependent on the specific nature thereof, as well as the needs of the subject.

Parenteral Dosage Forms

Parenteral dosage forms can be administered to patients by various routes including, but not limited to, subcutaneous, intravenous (including bolus injection), intramuscular, and intraarterial. In some embodiments, administration of a parenteral dosage form bypasses patients' natural defenses against contaminants, and thus, in these embodiments, parenteral dosage forms are sterile or capable of being sterilized prior to administration to a patient. Examples of parenteral dosage forms include, but are not limited to, solutions ready for injection, dry products ready to be dissolved or suspended in a pharmaceutically acceptable vehicle for injection, suspensions ready for injection, and emulsions.

Suitable vehicles that can be used to provide parenteral dosage forms are well known to those skilled in the art. Examples include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate.

Compounds that increase the solubility of one or more of the active ingredients disclosed herein can also be incorporated into the parenteral dosage forms. For example, cyclodextrin and its derivatives can be used to increase the solubility of a compound provided herein. See, e.g., U.S. Pat. No. 5,134,127, which is incorporated herein by reference.

Topical and Mucosal Dosage Forms

Topical and mucosal dosage forms provided herein include, but are not limited to, sprays, aerosols, solutions, emulsions, suspensions, eye drops or other ophthalmic preparations, or other forms known to one of skill in the art. See, e.g., Remington's Pharmaceutical Sciences, 16$^{th}$, 18$^{th}$ and 20$^{th}$ eds., Mack Publishing, Easton PA (1980, 1990 and 2000); and Introduction to Pharmaceutical Dosage Forms, 4th ed., Lea & Febiger, Philadelphia (1985). Dosage forms suitable for treating mucosal tissues within the oral cavity can be formulated as mouthwashes or as oral gels.

Suitable excipients (e.g., carriers and diluents) and other materials that can be used to provide topical and mucosal dosage forms encompassed herein are well known to those skilled in the pharmaceutical arts, and depend on the particular tissue to which a given pharmaceutical composition or dosage form will be applied. In one embodiment, excipients include, but are not limited to, water, acetone, ethanol, ethylene glycol, propylene glycol, butane-1,3-diol, isopropyl myristate, isopropyl palmitate, mineral oil, and mixtures thereof to form solutions, emulsions or gels, which are non-toxic and pharmaceutically acceptable. Moisturizers or humectants can also be added to pharmaceutical compositions and dosage forms. Examples of additional ingredients are well known in the art. See, e.g., Remington's Pharmaceutical Sciences, 16$^{th}$, 18$^{th}$ and 20$^{th}$ eds., Mack Publishing, Easton PA (1980, 1990 and 2000).

The pH of a pharmaceutical composition or dosage form may also be adjusted to improve delivery of one or more active ingredients. Also, the polarity of a solvent carrier, its ionic strength, or tonicity can be adjusted to improve delivery. Compounds such as stearates can also be added to pharmaceutical compositions or dosage forms to alter the hydrophilicity or lipophilicity of one or more active ingredients so as to improve delivery. In other embodiments, stearates can serve as a lipid vehicle for the formulation, as an emulsifying agent or surfactant, or as a delivery-enhancing or penetration-enhancing agent. In other embodiments, salts, solvates, hydrates, prodrugs, clathrates, or stereoisomers of the active ingredients can be used to further adjust the properties of the resulting composition.

5.7 Kits

In one aspect, provided herein is a kit for a method provided herein.

In some embodiments, provided herein is a kit of determining a dose of a treatment compound for treating a subject having systemic lupus erythematosus (SLE), wherein the kit comprises the agents for obtaining a sample from the subject; and measuring the gene expression level of IKZF3 in the sample, wherein the treatment compound is a compound of Formula I:

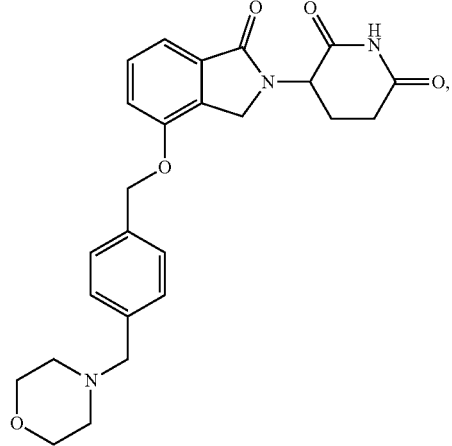

or a pharmaceutically acceptable salt, solvate, hydrate, stereoisomer, tautomer or racemic mixture thereof.

In some embodiments, the kit further comprises an instruction for determining the dose of the treatment compound to be 0.45 mg or higher per day if a score calculated based on the gene expression level of IKZF3 in the sample is higher than a reference level. In some embodiments, the score is Log 2 of the gene expression level of IKZF3 relative to a reference gene in the sample, or wherein the score is Log 2 of the gene expression level of IKZF3 relative to an average gene expression level of two or more reference genes in the sample. In some embodiments, the reference gene is selected from a group consisting of TFRC, ACTB, GAPDH, and combinations thereof.

In other embodiments, provided herein is a kit of determining a dose of a treatment compound for treating a subject having systemic lupus erythematosus (SLE), comprising agents for obtaining a sample from the subject; and measuring the gene expression levels of IFI27, IFI44, IFI44L, and RSAD2 in the sample; wherein the treatment compound is a compound of Formula I:

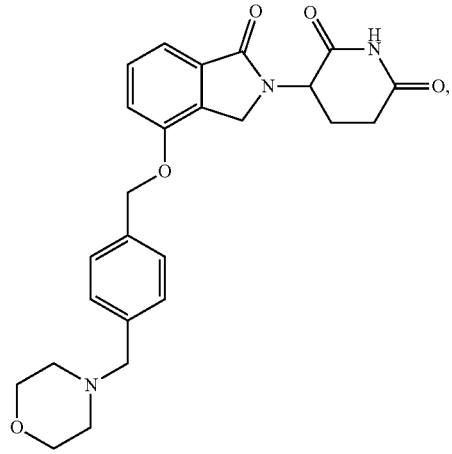

or a pharmaceutically acceptable salt, solvate, hydrate, stereoisomer, tautomer or racemic mixture thereof.

In some embodiments, the kit further comprises an instruction for determining the dose of the treatment compound to be 0.45 mg or higher per day or to be 0.15 mg or lower per day if a score calculated based on the gene expression levels of IFI27, IFI44, IFI44L, and RSAD2 is higher than a reference level. In some embodiments, the score is Log 2 of an average of the gene expression levels of IFI27, IFI44, IFI44L, and RSAD2 relative to a reference gene in the sample, or wherein the score is Log 2 of an average of the gene expression levels of IFI27, IFI44, IFI44L, and RSAD2 relative to an average of two or more reference genes in the sample. In some embodiments, the reference gene is selected from a group consisting of TFRC, ACTB, GAPDH, and combinations thereof.

In yet other embodiments, provided herein is a kit for identifying a subject having systemic lupus erythematosus (SLE) who is likely to be responsive to a treatment compound or predicting the responsiveness of a subject having SLE to a treatment compound, comprising agents for obtaining a sample from the subject; and determining (i) the gene expression level of IKZF3 or (ii) the gene expression levels of IFI27, IFI44, IFI44L, and RSAD2 in the sample, wherein the treatment compound is a compound of Formula I:

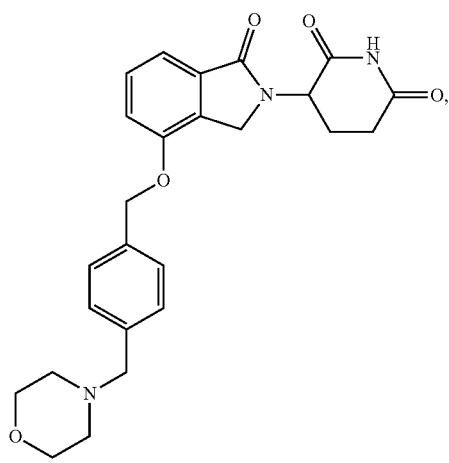

or a pharmaceutically acceptable salt, solvate, hydrate, stereoisomer, tautomer or racemic mixture thereof.

In some embodiments, the kit further comprises an instruction for diagnosing the subject as being likely to be responsive to the treatment compound if a score calculated based on the gene expression level of IKZF3 or the gene expression levels of IFI27, IFI44, IFI44L, and RSAD2 is higher than a reference level. In some embodiments, the instruction comprises determining the gene expression level of IKZF3 and diagnosing the subject as being likely to be responsive to the treatment compound if the score calculated based on the gene expression level of IKZF3 is higher than the reference level. In some embodiments, the score is Log 2 of the gene expression level of IKZF3 relative to a reference gene in the sample, or wherein the score is Log 2 of the gene expression level of IKZF3 relative to an average gene expression level of two or more reference genes in the sample. In some embodiments, the reference level is −0.49. In some embodiments, the reference gene is selected from a group consisting of TFRC, ACTB, GAPDH, and combinations thereof.

In other embodiments, the instruction comprises determining the gene expression levels of IFI27, IFI44, IFI44L, and RSAD2 and diagnosing the subject as being likely to be responsive to the treatment compound if the score calculated based on the gene expression levels of IFI27, IFI44, IFI44L, and RSAD2 is higher than the reference level. In some embodiments, the score is Log 2 of an average of the gene expression levels of IFI27, IFI44, IFI44L, and RSAD2 relative to a reference gene in the sample, or wherein the score is Log 2 of an average of the gene expression levels of IFI27, IFI44, IFI44L, and RSAD2 relative to an average of two or more reference genes in the sample. In some embodiments, the reference level is −1.38. In some embodiments, the reference gene is selected from a group consisting of TFRC, ACTB, GAPDH, and combinations thereof.

In yet other embodiments, provided herein is a kit for determining a dose of a treatment compound for treating a subject having systemic lupus erythematosus (SLE), comprising agents for (a) obtaining a sample from the subject; (b) measuring (i) the gene expression level of IKZF3 and (ii) the gene expression levels of IFI27, IFI44, IFI44L, and RSAD2 in the sample; wherein the treatment compound is a compound of Formula I:

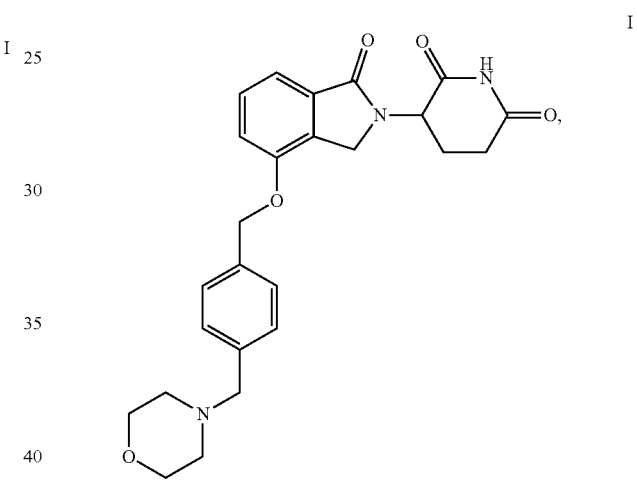

or a pharmaceutically acceptable salt, solvate, hydrate, stereoisomer, tautomer or racemic mixture thereof.

In some embodiments, the kit further comprises an instruction for determining a first score based on the gene expression level of IKZF3 and comparing the first score with a first reference level; determining a second score based on the gene expression levels of IFI27, IFI44, IFI44L, and RSAD2 and comparing the second score with a second reference level; and determining the dose of the treatment compound based on the first score and the second score. In some embodiments, the first score is Log 2 of the gene expression level of IKZF3 relative to a reference gene in the sample, or wherein the first score is Log 2 of the gene expression level of IKZF3 relative to an average gene expression level of two or more reference genes in the sample. In some embodiments, the first reference level is −0.49. In some embodiments, the reference gene is selected from a group consisting of TFRC, ACTB, GAPDH, and combinations thereof. In some embodiments, the second score is Log 2 of an average of the gene expression levels of IFI27, IFI44, IFI44L, and RSAD2 relative to a reference gene in the sample, or wherein the second score is Log 2 of an average of the gene expression levels of IFI27, IFI44, IFI44L, and RSAD2 relative to an average of two or more reference genes in the sample. In some embodiments, the second reference level is −1.38. In some embodiments, the reference gene is selected from a group consisting of TFRC, ACTB, GAPDH, and combinations thereof.

In some embodiments, the instruction comprises that when the first score is higher than the first reference level and the second score is higher than the second reference level, the dose of the treatment compound is determined to be 0.45 mg or higher per day or to be 0.15 mg or lower per day.

In other embodiments, the instruction comprises that when the first score is higher than the first reference level and the second score is lower than the second reference level, the dose of the treatment compound is determined to be 0.15 mg or lower per day.

In yet other embodiments, the instruction comprises that when the first score is lower than the first reference level and the second score is higher than the second reference level, the dose of the treatment compound is determined to be 0.45 mg or higher per day.

In yet another aspect, provided herein is a kit for identifying a subject having systemic lupus erythematosus (SLE) who is likely to be responsive to a treatment compound or predicting the responsiveness of a subject having SLE to a treatment compound, comprising agents for (a) obtaining a sample from the subject; (b) determining the presence of IKZF1 single nucleotide polymorphism (SNP) rs4917014 in the sample, wherein the treatment compound is a compound of Formula I:

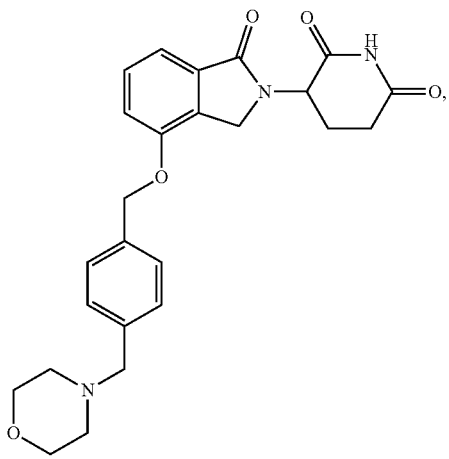

I or a pharmaceutically acceptable salt, solvate, hydrate, stereoisomer, tautomer or racemic mixture thereof.

In some embodiments, the kit further comprises an instruction of diagnosing the subject as being likely to be responsive to the treatment compound if at least one copy of SNP rs4917014 is detected.

In some embodiments, the compound is (S)-3-[4-(4-morpholin-4-ylmethylbenzyloxy)-1-oxo-1,3-dihydro-isoindo-2-yl]piperidine-2,6-dione or a pharmaceutically acceptable salt, solid form, solvate, hydrate, tautomer, stereoisomer or racemate thereof. In some embodiments, the compound is (S)-3-[4-(4-morpholin-4-ylmethylbenzyloxy)-1-oxo-1,3-dihydro-isoindo-2-yl]piperidine-2,6-dione. In yet other embodiments, the compound is (S)-3-[4-(4-morpholin-4-ylmethylbenzyloxy)-1-oxo-1,3-dihydro-isoindo-2-yl]piperidine-2,6-dione hydrochloride.

In some embodiments, the kit comprises agents for determining the protein level. In other embodiments, the kit comprises agents for determining the mRNA level. In yet other embodiments, the kit comprises agents for determining the cDNA level.

In certain embodiments, provided herein is a kit for detecting the mRNA level of one or more biomarkers. In certain embodiments, the kit comprises one or more probes that bind specifically to the mRNAs of the one or more biomarkers. In certain embodiments, the kit further comprises a washing solution. In certain embodiments, the kit further comprises reagents for performing a hybridization assay, mRNA isolation or purification means, detection means, as well as positive and negative controls. In certain embodiments, the kit further comprises an instruction for using the kit. The kit can be tailored for in-home use, clinical use, or research use.

In certain embodiments, provided herein is a kit for detecting the protein level of one or more biomarkers. In certain embodiments, the kits comprises a dipstick coated with an antibody that recognizes the protein biomarker, washing solutions, reagents for performing the assay, protein isolation or purification means, detection means, as well as positive and negative controls. In certain embodiments, the kit further comprises an instruction for using the kit. The kit can be tailored for in-home use, clinical use, or research use.

Such a kit can employ, for example, a dipstick, a membrane, a chip, a disk, a test strip, a filter, a microsphere, a slide, a multi-well plate, or an optical fiber. The solid support of the kit can be, for example, a plastic, silicon, a metal, a resin, glass, a membrane, a particle, a precipitate, a gel, a polymer, a sheet, a sphere, a polysaccharide, a capillary, a film, a plate, or a slide. The biological sample can be, for example, a cell culture, a cell line, a tissue, an organ, an organelle, a biological fluid, a blood sample, a urine sample, or a skin sample.

In another embodiment, the kit comprises a solid support, nucleic acids attached to the support, where the nucleic acids are complementary to at least 20, 50, 100, 200, 350, or more bases of mRNA, and a means for detecting the expression of the mRNA in a biological sample.

In a specific embodiment, the pharmaceutical or assay kit comprises, in a container, a compound or a pharmaceutical composition thereof, and further comprises, in one or more containers, components for isolating RNA. In another specific embodiment, the pharmaceutical or assay kit comprises, in a container, a compound or a pharmaceutical composition, and further comprises, in one or more containers, components for conducting RT-PCR, qRT-PCR, deep sequencing, or microarray In certain embodiments, the kits provided herein employ means for detecting the expression of a biomarker by quantitative real-time PCR (qRT-PCR), microarray, flow cytometry, or immunofluorescence. In other embodiments, the expression of the biomarker is measured by ELISA-based methodologies or other similar methods known in the art.

In another specific embodiment, the pharmaceutical or assay kit comprises, in a container, a compound or a pharmaceutical composition thereof, and further comprises, in one or more containers, components for isolating protein. In another specific embodiment, the pharmaceutical or assay kit comprises, in a container, a compound or a pharmaceutical composition, and further comprises, in one or more containers, components for conducting flow cytometry or ELISA.

In another aspect, provided herein are kits for measuring biomarkers that supply the materials necessary to measure the abundance of one or more gene products of the biomarkers or a subset of the biomarkers (e.g., one, two, three, four, five, or more biomarkers) provided herein. Such kits may comprise materials and reagents required for measuring RNA or protein. In some embodiments, such kits include microarrays, wherein the microarray is comprised of oligonucleotides and/or DNA and/or RNA fragments which hybridize to one or more gene products of the biomarkers or a subset of the biomarkers provided herein, or any combination thereof. In some embodiments, such kits may include primers for PCR of either the RNA product or the cDNA copy of the RNA product of the biomarkers or a subset of the biomarkers, or both. In some embodiments, such kits may include primers for PCR as well as probes for qPCR. In some embodiments, such kits may include multiple primers and multiple probes, wherein some of the probes have different fluorophores so as to permit simultaneously measuring multiple gene products of the biomarkers or a subset of the biomarkers provided herein. In some embodiments, such kits may further include materials and reagents for creating cDNA from RNA. In some embodiments, such kits may include antibodies specific for the protein products of the biomarkers or a subset of the biomarkers provided herein. Such kits may additionally comprise materials and reagents for isolating RNA and/or proteins from a biological sample. In addition, such kits may include materials and reagents for synthesizing cDNA from RNA isolated from a biological sample. In some embodiments, such kits may include a computer program product embedded on computer readable media for predicting whether a patient is clinically sensitive to a compound. In some embodiments, the kits may include a computer program product embedded on a computer readable media along with instructions.

In some embodiments, such kits measure the expression of one or more nucleic acid products of the biomarkers or a subset of the biomarkers provided herein. In accordance with this embodiment, the kits may comprise materials and reagents that are necessary for measuring the expression of particular nucleic acid products of the biomarkers or a subset of the biomarkers provided herein. For example, a microarray or RT-PCR kit may be produced for a specific condition and contain only those reagents and materials necessary for measuring the levels of specific RNA transcript products of the biomarkers or a subset of the biomarkers provided herein, to predict whether a patient is clinically sensitive to a compound. Alternatively, in some embodiments, the kits can comprise materials and reagents necessary for measuring the expression of particular nucleic acid products of genes other than the biomarkers provided herein. For example, in certain embodiments, the kits comprise materials and reagents necessary for measuring the expression levels of 1, 2, 3, 4, 5, 6, 7, 8, 9, 10, 15, 20, 25, 30, 35, 40, 45, 50, or more of the genes of the biomarkers provided herein, in addition to reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more genes other than the biomarkers provided herein. In other embodiments, the kits contain reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more of the biomarkers provided herein, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not the biomarkers provided herein. In certain embodiments, the kits contain reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more of the genes of the biomarkers provided herein, and 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 genes that are not the biomarkers provided herein.

For nucleic acid microarray kits, the kits generally comprise probes attached to a solid support surface. In one such embodiment, probes can be either oligonucleotides or longer probes including probes ranging from 150 nucleotides to 800 nucleotides in length. The probes may be labeled with a detectable label. In a specific embodiment, the probes are specific for one or more of the gene products of the biomarkers provided herein. The microarray kits may comprise instructions for performing the assay and methods for interpreting and analyzing the data resulting from performing the assay. In a specific embodiment, the kits comprise instructions for predicting whether a patient is clinically sensitive to a compound. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own suitable container.

In certain embodiments, a nucleic acid microarray kit comprises materials and reagents necessary for measuring the expression levels of 1, 2, 3, 4, 5, 6, 7, 8, 9, 10, 15, 20, 25, 30, 35, 40, 45, 50, or more of the genes of the biomarkers provided herein, or a combination thereof, in addition to reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more genes other than those of the biomarkers provided herein. In other embodiments, a nucleic acid microarray kit contains reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more of the genes of the biomarkers provided herein, or any combination thereof, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not of the biomarkers provided herein. In another embodiment, a nucleic acid microarray kit contains reagents and materials necessary for measuring the expression levels of at least 1, at least 2, at least 3, at least 4, at least 5, at least 6, at least 7, at least 8, at least 9, at least 10, at least 15, at least 20, at least 25, at least 30, at least 35, at least 40, at least 45, at least 50, or more of the genes of the biomarkers provided herein, or any combination thereof, and 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000, or 500-1000 genes that are not of the biomarkers provided herein.

For quantitative PCR, the kits generally comprise preselected primers specific for particular nucleic acid sequences. The quantitative PCR kits may also comprise enzymes suitable for amplifying nucleic acids (e.g., polymerases such as Taq polymerase), deoxynucleotides, and buffers needed for amplification reaction. The quantitative PCR kits may also comprise probes specific for the nucleic acid sequences associated with or indicative of a condition. The probes may or may not be labeled with a fluorophore. The probes may or may not be labeled with a quencher molecule. In some embodiments, the quantitative PCR kits also comprise components suitable for reverse-transcribing RNA, including enzymes (e.g., reverse transcriptases such as AMV, MMLV, and the like) and primers for reverse transcription along with deoxynucleotides and buffers needed for reverse transcription reaction. Each component of the quantitative PCR kit is generally in its own suitable container. Thus, these kits generally comprise distinct containers suitable for each individual reagent, enzyme, primer and probe. Further, the quantitative PCR kits may comprise instructions for performing the reaction and methods for interpreting and analyzing the data resulting from performing the reaction. In a specific embodiment, the kits contain instructions for predicting whether a patient is clinically sensitive to a compound.

For antibody-based kits, the kit can comprise, for example: (1) a first antibody (which may or may not be attached to a solid support) that binds to a peptide, polypeptide or protein of interest; and, optionally, (2) a second, different antibody that binds to either the first antibody or the peptide, polypeptide, or protein, and is conjugated to a detectable label (e.g., a fluorescent label, radioactive isotope, or enzyme). In a specific embodiment, the peptide, polypeptide, or protein of interest is associated with or indicative of a condition (e.g., a disease). The antibody-based kits may also comprise beads for conducting immunoprecipitation. Each component of the antibody-based kits is generally in its own suitable container. Thus, these kits generally comprise distinct containers suitable for each antibody and reagent. Further, the antibody-based kits may comprise instructions for performing the assay and methods for interpreting and analyzing the data resulting from performing the assay. In a specific embodiment, the kits contain instructions for predicting whether a patient is clinically sensitive to a compound.

In one embodiment, a kit provided herein comprises a compound provided herein, or a pharmaceutically acceptable salt, solvate, stereoisomer, isotopologue, prodrug, hydrate, co-crystal, clathrate, or a polymorph thereof. Kits may further comprise additional active agents, including but not limited to those disclosed herein.

Kits provided herein may further comprise devices that are used to administer the active ingredients. Examples of such devices include, but are not limited to, syringes, drip bags, patches, and inhalers.

Kits may further comprise cells or blood for transplantation, as well as pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles include, but are not limited to, water for injection USP; aqueous vehicles (such as, but not limited to, sodium chloride injection, Ringer's injection, dextrose injection, dextrose and sodium chloride injection, and lactated Ringer's injection); water-miscible vehicles (such as, but not limited to, ethyl alcohol, polyethylene glycol, and polypropylene glycol); and non-aqueous vehicles (such as, but not limited to, corn oil, cottonseed oil, peanut oil, sesame oil, ethyl oleate, isopropyl myristate, and benzyl benzoate).

In certain embodiments of the methods and kits provided herein, solid phase supports are used for purifying proteins, labeling samples, or carrying out the solid phase assays. Examples of solid phases suitable for carrying out the methods disclosed herein include beads, particles, colloids, single surfaces, tubes, multi-well plates, microtiter plates, slides, membranes, gels, and electrodes. When the solid phase is a particulate material (e.g., a bead), it is, in one embodiment, distributed in the wells of multi-well plates to allow for parallel processing of the solid phase supports.

It is noted that any combination of the above-listed embodiments, for example, with respect to one or more reagents, such as, without limitation, nucleic acid primers, solid support, and the like, are also contemplated in relation to any of the various methods and/or kits provided herein.

Certain embodiments of the invention are illustrated by the following non-limiting examples.

6. EXAMPLES

The examples below are carried out using standard techniques, which are well known and routine to those of skill in the art, except where otherwise described in detail. The examples are intended to be merely illustrative.

6.1 Example 1: Preparation of (S)-3-[4-(4-morpholin-4-ylmethylbenzyloxy)-1-oxo-1,3-dihydro-isoindo-2-yl]piperidine-2,6-dione Hydrochloride

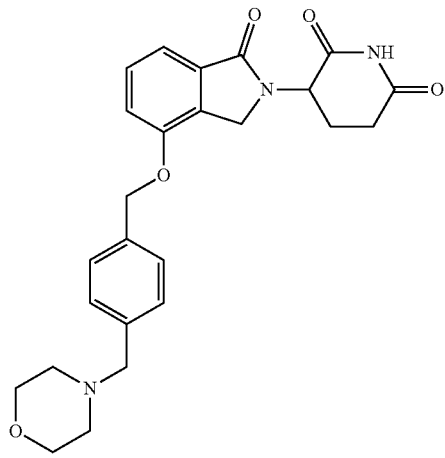 [SMILES: O=C1CCC(N2Cc3c(OCc4ccc(CN5CCOCC5)cc4)cccc3C2=O)C(=O)N1]

(1) 3-Hydroxy-2-methyl-benzoic Acid Methyl Ester

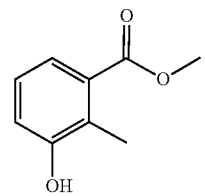

3-Hydroxy-2-methylbenzoic acid (105 g, 690 mmol) was added to MeOH (800 mL) in a 2 L three neck round bottom flask equipped with condenser, thermometer and stirring bar followed by the addition of MeOH (250 ml). H$_2$SO$_4$ (10 mL, 180 mmol) was added to above solution. The reaction mixture was stirred at 62° C. for 17 hours. The solvent was removed in vacuo. The residue (200 mL) was added to water (600 mL) slowly at room temperature and a white solid was formed. The suspension was stirred in an ice bath for 30 minutes and filtered. The solid was washed with water (5×250 mL) and dried to give 3-hydroxy-2-methyl-benzoic acid methyl ester as a white solid (100 g, 87% yield). The compound was used in the next step without further purification: LCMS MH=167; $^1$H NMR (DMSO-d$_6$) δ 2.28 (s, 3H, CH$_3$), 3.80 (s, 3H, CH$_3$), 6.96-7.03 (m, 1H, Ar), 7.09 (t, J=7.8 Hz, 1H, Ar), 7.14-7.24 (m, 1H, Ar), 9.71 (s, 1H, OH).

(2) 3-(tert-Butyl-dimethyl-silanyloxy)-2-methyl-benzoic Acid Methyl Ester

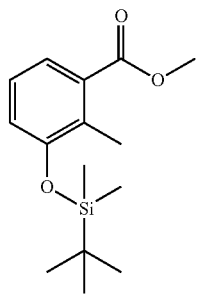 [SMILES: COC(=O)c1cccc(O[Si](C)(C)C(C)(C)C)c1C]

To a 1 L three neck RB flask equipped with stirring bar and thermometer, were added DMF (300 mL), methyl 3-hydroxy-2-methylbenzoate (90 g, 542 mmol) and imidazole (92 g, 1,354 mmol). TBDMS-Cl (90 g, 596 mmol) was added to the above solution in portions to control the internal temp between 15-19° C. over 20 minutes, and after addition, the internal temp dropped below 1° C. The ice bath was removed and the reaction mixture was stirred at room temperature for 16 hours. The reaction mixture was added to ice water (500 mL), and the resulting solution was divided into two portions (700 mL×2). Each portion was extracted with EtOAc (700 mL). Each organic layer was washed with cold water (350 mL) and brine (350 mL). Organic layers were combined and dried by MgSO$_4$. The combined organic layer was concentrated to give 3-(tert-butyl-dimethyl-silanyloxy)-2-methyl-benzoic acid methyl ester as a light brown oil (160 g, 100% crude yield). The compound was used in the next step without further purification: LCMS MH=281; $^1$H NMR (DMSO-d$_6$) δ −0.21 (s, 6H, CH$_3$, CH$_3$), 0.73-0.84 (m, 9H, CH$_3$, CH$_3$, CH$_3$), 2.10 (s, 3H, CH$_3$), 3.60 (s, 3H, CH$_3$), 6.82 (dd, 1H, Ar), 6.97 (t, J=7.9 Hz, 1H, Ar), 7.13 (dd, J=1.1, 7.7 Hz, 1H, Ar).

(3) 2-Bromomethyl-3-(tert-butyl-dimethyl-silanyloxy)-benzoic Acid Methyl Ester

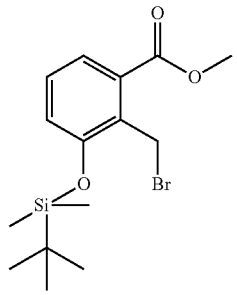 [SMILES: COC(=O)c1cccc(O[Si](C)(C)C(C)(C)C)c1CBr]

NBS (49.8 g, 280 mmol) was added to methyl 3-(tert-butyl dimethylsilyloxy)-2-methylbenzoate (78.4 g, 280 mmol) in methyl acetate (500 mL) at room temperature to give an orange colored suspension. The resulting reaction mixture was heated in an oil bath at 40° C. and shined by 300 wt sunlight bulb at reflux for 4 hours. The reaction mixture was cooled down and washed by Na$_2$SO$_3$ solution (2×600 mL, 50% saturated concentration), water (500 mL) and brine (600 mL). The organic layer was dried by MgSO$_4$ and decolorized by charcoal. The organic layer was concentrated to give 2-bromomethyl-3-(tert-butyl-dimethyl-silanyloxy)-benzoic acid methyl ester as a light brown oil (96 g, 91% crude yield). The compound was used in the next step without further purification: LCMS M-Br=279; $^1$H NMR (DMSO-d$_6$) δ 0.05-0.11 (m, 6H, CH$_3$, CH$_3$), 0.82 (s, 9H, CH$_3$, CH$_3$, CH$_3$), 3.65 (s, 3H, CH$_3$), 4.74 (s, 2H, CH$_2$), 6.94 (dd, J=1.3, 8.1 Hz, 1H, Ar), 7.10-7.20 (m, 1H, Ar), 7.21-7.29 (m, 1H, Ar).

(4) 4-Carbamoyl-butyric Acid Methyl Ester

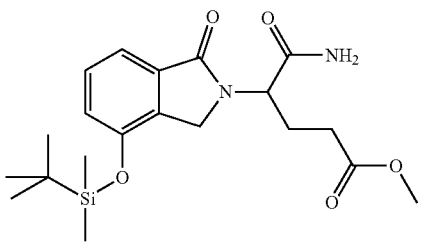 [SMILES: COC(=O)CCC(C(N)=O)N1Cc2c(O[Si](C)(C)C(C)(C)C)cccc2C1=O]

To a stirred solution of methyl 2-(bromomethyl)-3-(tert-butyldimethylsilyloxy)benzoate (137.5 g, 325 mmol) in acetonitrile (1100 mL) in a 2 L round bottom flask, was added methyl 4,5-diamino-5-oxopentanoate hydrochloride (70.4 g, 358 mmol). To the suspension was added DIPEA (119 ml, 683 mmol) through an addition funnel over 10 minutes and the suspension was stirred at room temperature for 1 hour before the mixture was heated in an oil bath at 40° C. for 23 hours. The reaction mixture was concentrated under vacuo. The residue was stirred in ether (600 mL), and a white solid precipitated out. The mixture was filtered and the solid was washed with ether (400 mL). The filtrate was washed with HCl (1N, 200 mL), NaHCO$_3$ (sat. 200 mL) and brine (250 mL). The aqueous acid layer and basic layer were kept separately. Then the solid was further washed with ether (250 mL) and the liquid was washed with above acid solution and basic solution. The two organic layers were combined and concentrated under vacuo to give 4-[4-(tert-Butyl-dimethyl-silanyloxy)-1-oxo-1,3-dihydro-isoindol-2-yl]-4-carbamoyl-butyric acid methyl ester as a brown oil (152 g, 115% crude yield, 77% purity by H NMR). The compound was used in the next step without further purification: LCMS MH=407.

(5) 4-Carbamoyl-4-(4-hydroxy-1-oxo-1,3-dihydro-isoindol-2-yl)-butyric Acid Methyl Ester

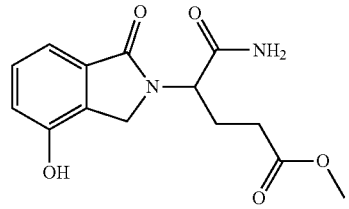 [SMILES: COC(=O)CCC(C(N)=O)N1Cc2c(O)cccc2C1=O]

To a stirred cold solution of methyl 5-amino-4-(4-(tert-butyldimethylsilyloxy)-1-oxoisoindolin-2-yl)-5-oxopentanoate (152 g, 288 mmol) in DMF (500 mL) and water (55 mL), was added by $K_2CO_3$ (19.89 g, 144 mmol) by portions over 5 minutes. The resulting reaction mixture was stirred at room temperature for 40 minutes. The reaction mixture was cooled in an ice bath. To the mixture, HCl (12M, 23.99 ml, 288 mmol) was added slowly. After the addition, acetonitrile (280 mL) was added to the mixture and a solid precipitated out. The mixture was stirred at room temperature for 10 minutes and filtered. The solid was washed with acetonitrile (50 mL×4). The filtrate was concentrated under high vacuo to give a yellow oil (168 g). The oil was dissolved in acetonitrile (600 mL) and stirred at room temperature for 10 minutes. The mixture was filtered and the solid was washed with acetonitrile (25 mL×2). The filtrate was concentrated under high vacuo to give a yellow oil (169 g), which was added to a mixture of water (1200 mL) and ether (1000 mL). The mixture was stirred for 3 minutes and the layers were separated. The aqueous solution was concentrated under high vacuo and the residue was stirred in acetonitrile (160 mL) and a white solid was formed after overnight stirring. The mixture was filtered to give 4-carbamoyl-4-(4-hydroxy-1-oxo-1,3-dihydro-isoindol-2-yl)-butyric acid methyl ester as a white solid (46 g, 54% yield). The filtrate was concentrated and the residue was further crystallized in acetonitrile (60 mL) to give more 4-carbamoyl-4-(4-hydroxy-1-oxo-1,3-dihydro-isoindol-2-yl)-butyric acid methyl ester as a white solid (11.7 g, 14% yield). The filtrate was concentrated and the residue was purified by ISCO chromatography to give more 4-carbamoyl-4-(4-hydroxy-1-oxo-1,3-dihydro-isoindol-2-yl)-butyric acid methyl ester as a white solid (13.2 g, 15% yield). The total product obtained was 70.9 g in 83% yield: LCMS MH=293; $^1$H NMR (DMSO-$d_6$) δ 1.95-2.34 (m, 4H, $CH_2$, $CH_2$), 3.51 (s, 3H, $CH_3$), 4.32 (d, J=17.6 Hz, 1H, CHH), 4.49 (d, J=17.4 Hz, 1H, CHH), 4.73 (dd, J=4.7, 10.2 Hz, 1H, CHH), 6.99 (dd, J=0.8, 7.9 Hz, 1H, Ar), 7.10-7.23 (m, 2H, Ar, NHH), 7.25-7.38 (m, 1H, Ar), 7.58 (s, 1H, NHH), 10.04 (s, 1H, OH).

(6) 3-(4-((4-(morpholinomethyl)benzyl)oxy)-1-oxoisoindolin-2-yl)piperidine-2,6-dione

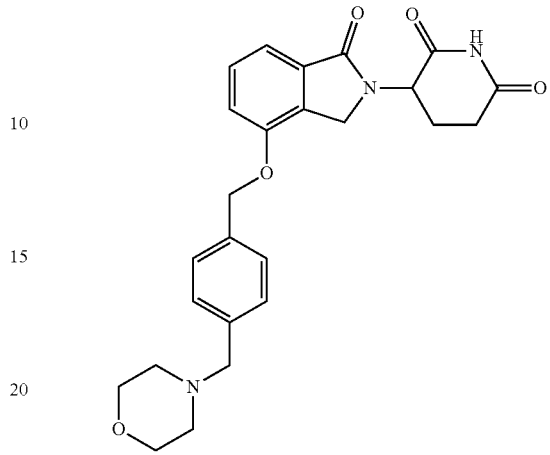

Step 1: To the solution of 3-(4-hydroxy-1-oxo-1,3-dihydro-isoindol-2-yl)-piperidine-2,6-dione (2.5 g, 8.56 mmol) in THF (60 mL) was added triphenyl phosphine (polymer supported 1.6 mmol/g, 12 g, 18.8 mmol). The mixture was stirred at room temperature for 15 minutes. Diisopropyl azodicarboxylate (3.96 mL, 18.8 mmol) was added at 0° C., and the mixture was stirred at 0° C. for 30 minutes. (4-Morpholin-4-ylmethyl-phenyl)-methanol (2.62 g, 12.4 mmol) was added at 0° C., and the mixture was allowed to warm to room temperature and stirred at room temperature overnight. The reaction mixture was filtered, and the filtrate was concentrated. The resulting oil was purified on silica gel column eluted with methylene chloride and methanol (gradient, product came out at 6% methanol) to give 4-carbamoyl-4-[4-(4-morpholin-4-ylmethyl-benzyloxy)-1-oxo-1,3-dihydro-isoindol-2-yl]-butyric acid methyl ester (2.2 g, 54% yield). The product was used in the next step without further purification.

Step 2: To the THF solution (50 mL) of 4-carbamoyl-4-[4-(4-morpholin-4-ylmethyl-benzyloxy)-1-oxo-1,3-dihydro-isoindol-2-yl]-butyric acid methyl ester (2.2 g, 4.57 mmol) was added potassium tert-butoxide (0.51 g, 4.57 mmol) at 0° C. The mixture was stirred at 0° C. for 10 minutes and was quenched with 1N HCl (5 mL, 5 mmol) followed by saturated $NaHCO_3$ (25 mL). The mixture was extracted with EtOAc (2×50 mL). The organic layer was washed with water (30 mL), brine (30 mL), dried over $MgSO_4$ and concentrated. To the resulting solid was added EtOAc (10 mL) followed by hexane (10 mL) under stirring. The suspension was filtered to give 3-(4-((4-(morpholinomethyl)benzyl)oxy)-1-oxoisoindolin-2-yl)piperidine-2,6-dione as white solid (1.5 g, 73% yield). HPLC: Waters Symmetry $C_{18}$, 5 μm, 3.9×150 mm, 1 mL/min, 240 nm, gradient to 95/5 acetonitrile/0.1% $H_3PO_4$ in 5 min: $t_R$=4.78 min (97.5%); mp: 210-212° C.; $^1$H NMR (DMSO-$d_6$) δ 1.86-2.09 (m, 1H, CHH), 2.29-2.38 (m, 4H, $CH_2$, $CH_2$), 2.44 (dd, J=4.3, 13.0 Hz, 1H, CHH), 2.53-2.64 (m, 1H, CHH), 2.82-2.99 (m, 1H, CHH), 3.46 (s, 2H, $CH_2$), 3.52-3.61 (m, 4H, $CH_2$, $CH_2$), 4.18-4.51 (m, 2H, $CH_2$), 5.11 (dd, J=5.0, 13.3 Hz, 1H, NCH), 5.22 (s, 2H, $CH_2$), 7.27-7.38 (m, 5H, Ar), 7.40-7.53 (m, 3H, Ar), 10.98 (s, 1H, NH) $^{13}$C NMR (DMSO-$d_6$) δ 22.36, 31.21, 45.09, 51.58, 53.14, 62.10, 66.17, 69.41, 114.97, 115.23, 127.64, 128.99, 129.81, 129.95, 133.31, 135.29, 137.68, 153.50, 168.01, 170.98, 172.83; LCMS: 465; Anal Calcd for $C_{25}H_{27}N_3O_5$+0.86 $H_2O$: C, 64.58; H, 6.23; N, 9.04; Found: C, 64.77; H, 6.24; N, 8.88.

(S)-3-(4-((4-(morpholinomethyl)benzyl)oxy)-1-oxoisoindolin-2-yl)piperidine-2,6-dione and (R)-3-(4-((4-(morpholinomethyl)benzyl)oxy)-1-oxoisoindolin-2-yl)piperidine-2,6-dione were prepared from 3-(4-((4-(morpholinomethyl)benzyl)oxy)-1-oxoisoindolin-2-yl)piperidine-2,6-dione through chiral separation.

6.2 Example 2: Biomarker-Enriched Patient Subsets

The pharmacokinetics, pharmacodynamics (PD), efficacy, and safety of oral iberdomide ((S)-3-[4-({4-[(morpholin-4-yl)methyl]phenyl}methoxy)-1-oxo-1,3-dihydro-2H-isoindol-2-yl]piperidine-2,6-dione-hydrogen chloride (1/1)) were evaluated in a phase 2b study in subjects with active autoantibody-positive SLE.

Adult SLE patients (N=288) with a ≥6-month history of SLE and SLE Disease Activity Index (SLEDAI 2K) ≥6 were randomized to placebo (n=83) or iberdomide 0.15 mg QD (n=42), 0.3 mg QD (n=82), or 0.45 mg QD (n=81). Clinical response was determined by the SLE Responder Index 4 (SRI-4) at week 24 for all patients and within pre-specified biomarker-enriched subsets based on expression of Ikaros, Aiolos, the Type 1 IFN signature (IFI27, IFI44, IFI44L, RSAD2), and other gene modules measured from fingerstick blood collected at baseline (Modular Immune Profile Test, DxTerity Diagnostics, Inc.). The primary objective of the study was to evaluate the clinical efficacy of 3 doses of iberdomide (0.45 mg once per day [QD], 0.30 mg QD, or 0.15 mg QD) compared to placebo, for the treatment of active SLE using the SLE Responder Index at Week 24.

Among all subjects with baseline gene expression data (N=287), 179 subjects (62.4%) were Type 1 IFN-High, and 110 subjects (38.3%) were Aiolos-High. These patient subsets were partially overlapping. The Type 1 IFN-High is 39.1% contained within the Aiolos-High subset, and the Aiolos-High subset is 63.6% contained within the IFN-High subset. There were 109 subjects (39.9%) who fit into the $IFN^{High}Aiolos^{Low}$ population, and 40 subjects (13.9%) who fit into the $IFN^{Low}Aiolos^{High}$ population. There were 70 subjects (24.4%) who fit into the $IFN^{High}Aiolos^{High}$ "double-positive" population. Conversely, there was an outlying subpopulation of 68 subjects (23.7%) who were $IFN^{Low}Aiolos^{Low}$, a "double-negative" population (FIG. 1). Treatment Effects in Subgroups Based on Baseline mRNA and DNA Subgroup analyses of SRI(4) response based on baseline mRNA and DNA expression showed larger effect sizes (with suggestion of a trend) compared with overall subjects for IKZF3 high (0.45 mg QD iberdomide), Type 1 IFN high (0.15 mg and 0.45 mg QD iberdomide), and Ikaros IFN module high (0.45 mg QD iberdomide) (Table 1).

TABLE 1

Percentage of Subjects Who Achieve SRI(4) at Week 24 by Baseline mRNA and DNA Subgroup (ITT Population)

| Population Iberdomide - Placebo Comparison | Placebo | Iberdomide | | |
|---|---|---|---|---|
| | | 0.15 mg QD | 0.30 mg QD | 0.45 mg QD |
| Overall Subjects, n/m (%)[a] | 29/83 (34.9) | 20/42 (47.6) | 33/82 (40.2) | 44/81 (54.3) |
| Stratified Difference (%) (95% CI)[b] | | 11.4 (−6.57, 29.00) | 5.0 (−9.77, 19.48) | 19.4 (4.12, 33.42) |
| P-value[b] | | 0.214 | 0.512 | 0.011 |
| IKZF1: High, n/m (%)[a] | 21/56 (37.5) | 12/28 (42.9) | 21/53 (39.6) | 35/64 (54.7) |
| Stratified Difference (%) (95% CI)[b] | | 7.0 (−14.36, 28.68) | 2.4 (−15.87, 20.58) | 16.1 (−1.76, 32.65) |
| P-value[b] | | 0.531 | 0.801 | 0.070 |
| IKZF3: High, n/m (%)[a] | 9/27 (33.3) | 5/14 (35.7) | 9/32 (28.1) | 23/36 (63.9) |
| Stratified Difference (%) (95% CI)[b] | | 2.2 (−24.82, 31.94) | −7.1 (−31.13, 16.94) | 32.9 (7.74, 52.90) |
| P-value[b] | | >0.999 | 0.580 | 0.011 |
| Type 1 IFN: High, n/m (%)[a] | 16/48 (33.3) | 15/25 (60.0) | 21/49 (42.9) | 34/57 (59.6) |
| Stratified Difference (%) (95% CI)[b] | | 25.6 (1.54, 46.35) | 10.6 (−8.93, 29.11) | 26.8 (7.49, 43.54) |
| P-value[b] | | 0.032 | 0.292 | 0.006 |
| Ikaros IFN: High, n/m (%)[a] | 17/49 (34.7) | 16/30 (53.3) | 21/49 (42.9) | 36/62 (58.1) |
| Stratified Difference (%) (95% CI)[b] | | 18.6 (−3.69, 39.05) | 8.9 (−10.47, 27.36) | 24.3 (5.45, 40.76) |
| P-value[b] | | 0.098 | 0.375 | 0.010 |
| T cell Exhaustion: Low, n/m (%)[a] | 23/60 (38.3) | 13/29 (44.8) | 28/65 (43.1) | 39/66 (59.1) |
| Stratified Difference (%) (95% CI)[b] | | 5.4 (−15.51, 26.63) | 4.7 (−12.69, 21.53) | 21.9 (4.30, 37.77) |
| P-value[b] | | 0.627 | 0.600 | 0.013 |
| B cell: High, n/m (%)[a] | 17/46 (37.0) | 8/24 (33.3) | 19/49 (38.8) | 30/54 (55.6) |
| Stratified Difference (%) (95% CI)[b] | | −0.7 (−22.56, 22.94) | 4.5 (−15.06, 23.69) | 20.4 (0.74, 38.01) |
| P-value[b] | | 0.952 | 0.658 | 0.039 |
| IKZF1 Status of SNP rs4917014: 1 or 2 Copies, n/m (%)[a] | 12/41 (29.3) | 11/21 (52.4) | 18/46 (39.1) | 20/36 (55.6) |

TABLE 1-continued

Percentage of Subjects Who Achieve SRI(4) at Week 24 by Baseline mRNA and DNA Subgroup (ITT Population)

| Population Iberdomide - Placebo Comparison | Placebo | Iberdomide | | |
|---|---|---|---|---|
| | | 0.15 mg QD | 0.30 mg QD | 0.45 mg QD |
| Stratified Difference (%) (95% CI)[b] | | 23.0 (−2.36, 46.07) | 7.9 (−12.18, 26.84) | −0.94, 41.03 |
| P-value[b] | | 0.078 | 0.444 | 0.047 |

CI = confidence interval;
IFN = interferon;
IKZF1 = Ikaros family zinc finger 1;
IKZF3 = Ikaros family zinc finger 3;
ITT = intent to treat;
n/m = number of subjects with the result/number of subjects in the assessed population;
QD = once daily;
QD = once daily;
SNP = single nucleotide polymorphism;
SRI = Systemic Lupus Erythematosus Responder Index.
[a]Analysis based on intent-to-treat population and nonresponder imputation. Subjects with insufficient data for response determination at the given time point were considered nonresponders.
[b]Stratified difference in proportions and 2-sided 95% Newcombe CI for the difference using the CMH weights, and 2-sided p-value from the CMH test (or an exact test). If 1 and only 1 of the 2 treatment groups being compared had no subject in a stratum, the stratified analysis was not performed and unstratified Newcombe CI for the difference and p-value from the chi-square test (or the Barnard's unconditional exact test) were provided instead and denoted with an asterisk (*); if both treatment groups being compared had no subject in a statum, the stratified analysis stratified analysis stratified by the remainign strata.
Note:
Stratification was based on baseline oral corticosteroid dose (≥10 mg/day and <10 mg/day) and screening SLEDAI 2K score (≥10 points and <10 points).

The best response rates were observed in the Type 1 IFN-High and Aiolos-High subsets. Results within the Ikaros Type 1 IFN-High subset were very similar to those of the Type 1 IFN-High subset, due to the essentially identical patient populations identified by these two gene modules.

Figure 2:
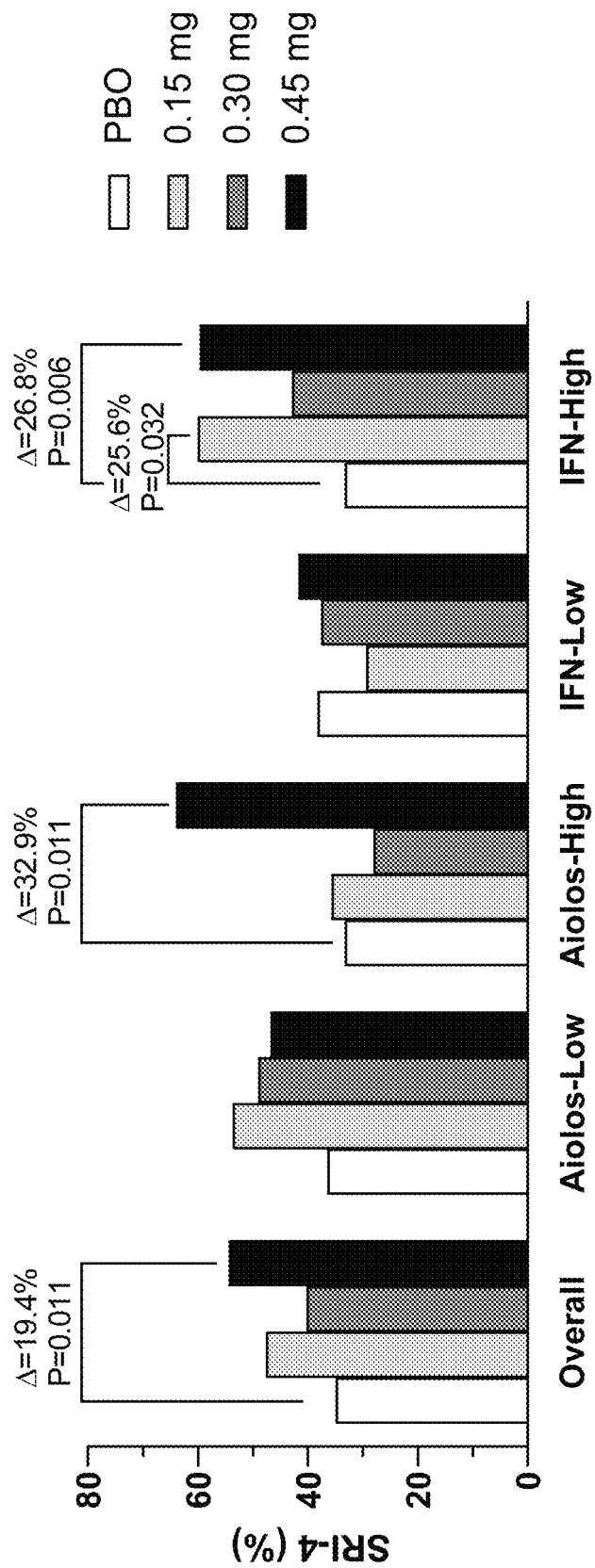
FIG. 2 shows week 24 SRI-4 clinical response rates in patient subsets defined by Aiolos and Type 1 IFN gene signature status at baseline (Aiolos=IKZF3; Type 1 IFN gene signature=IFI27, IFI44, IFI44L, RSAD2; Δ=treatment effect (stratified difference vs. placebo)).

As shown in FIG. 2, the high dose of iberdomide (0.45 mg) had a significant SRI-4 treatment effect versus placebo among patients within the baseline Aiolos-High subset (32.9%; P=0.011). There was no significant efficacy of the low dose (0.15 mg) or mid dose (0.3 mg) of iberdomide within the Aiolos-high subset.

Within the baseline Type 1 IFN-High subset, the low dose 0.15 mg dose had a significant SRI-4 treatment effect versus placebo of 25.6% (P=0.032), and the high dose 0.45 mg had a significant SRI-4 treatment effect versus placebo of 26.8% (P=0.006) (FIG. 2).

Figure 3:
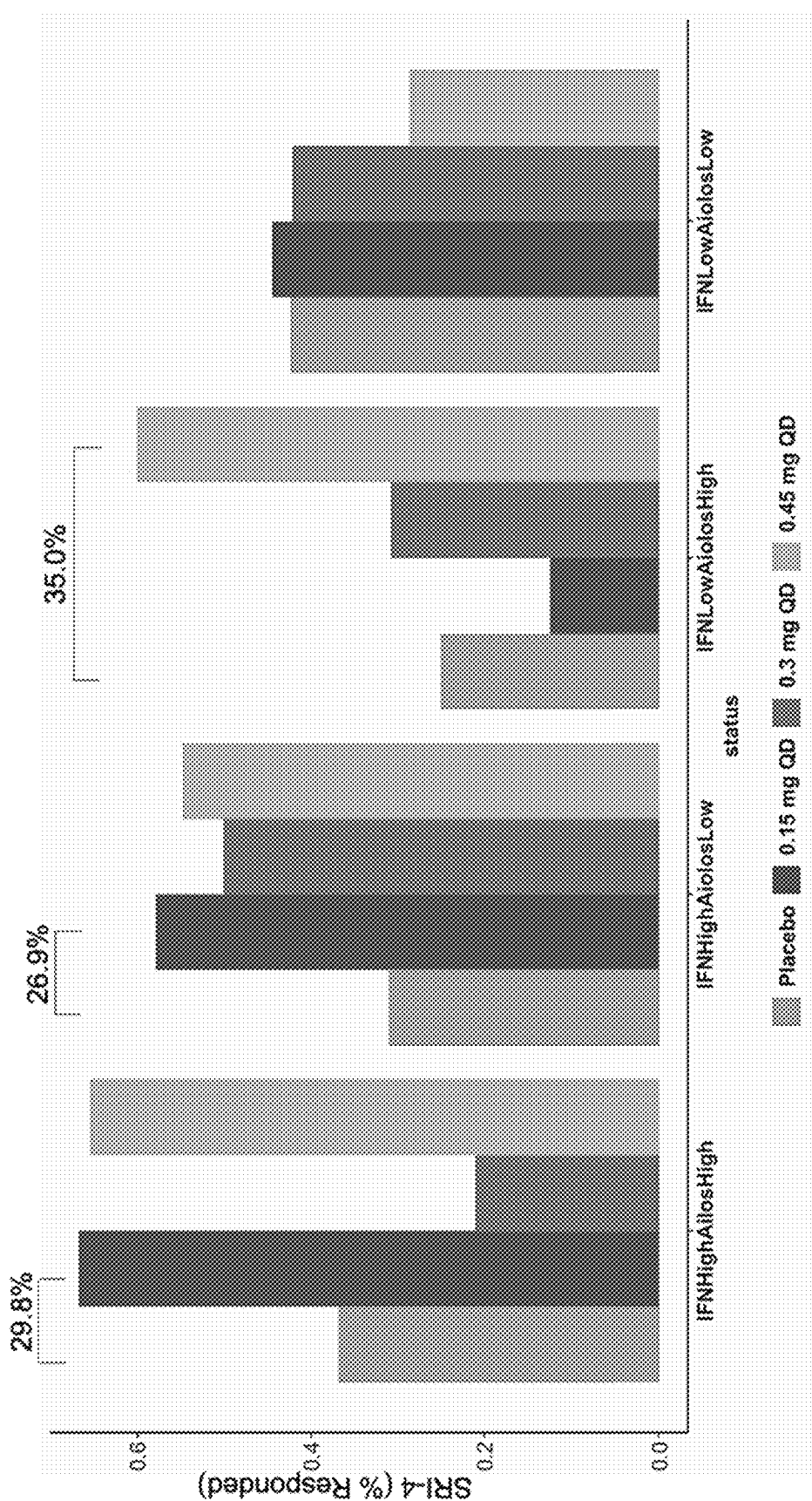
FIG. 3 shows SRI-4 clinical response rate to iberdomide in SLE subsets according to both Type 1 IFN and Aiolos gene expression status.

In addition, as shown in FIG. 3, the low dose 0.15 mg and high 0.45 mg were efficacious in the IFN$^{High}$Aiolos$^{High}$ double-positive population, with similar SRI-4 treatment effect versus placebo of 29.8%. Within the IFN$^{High}$Aiolos$^{Low}$ population, the low dose 0.15 mg had an SRI-4 treatment effect versus placebo of 26.8%, which slightly outperformed the high dose 0.45 mg. Conversely, within the IFN$^{Low}$Aiolos$^{High}$ subset, only the high dose 0.45 mg was clinically efficacious with an SRI-4 treatment effect versus placebo of 35.0%. Finally, in the double-negative IFN$^{Low}$Aiolos$^{Low}$ population, iberdomide had no clinical efficacy (FIG. 3).

Figure 4:
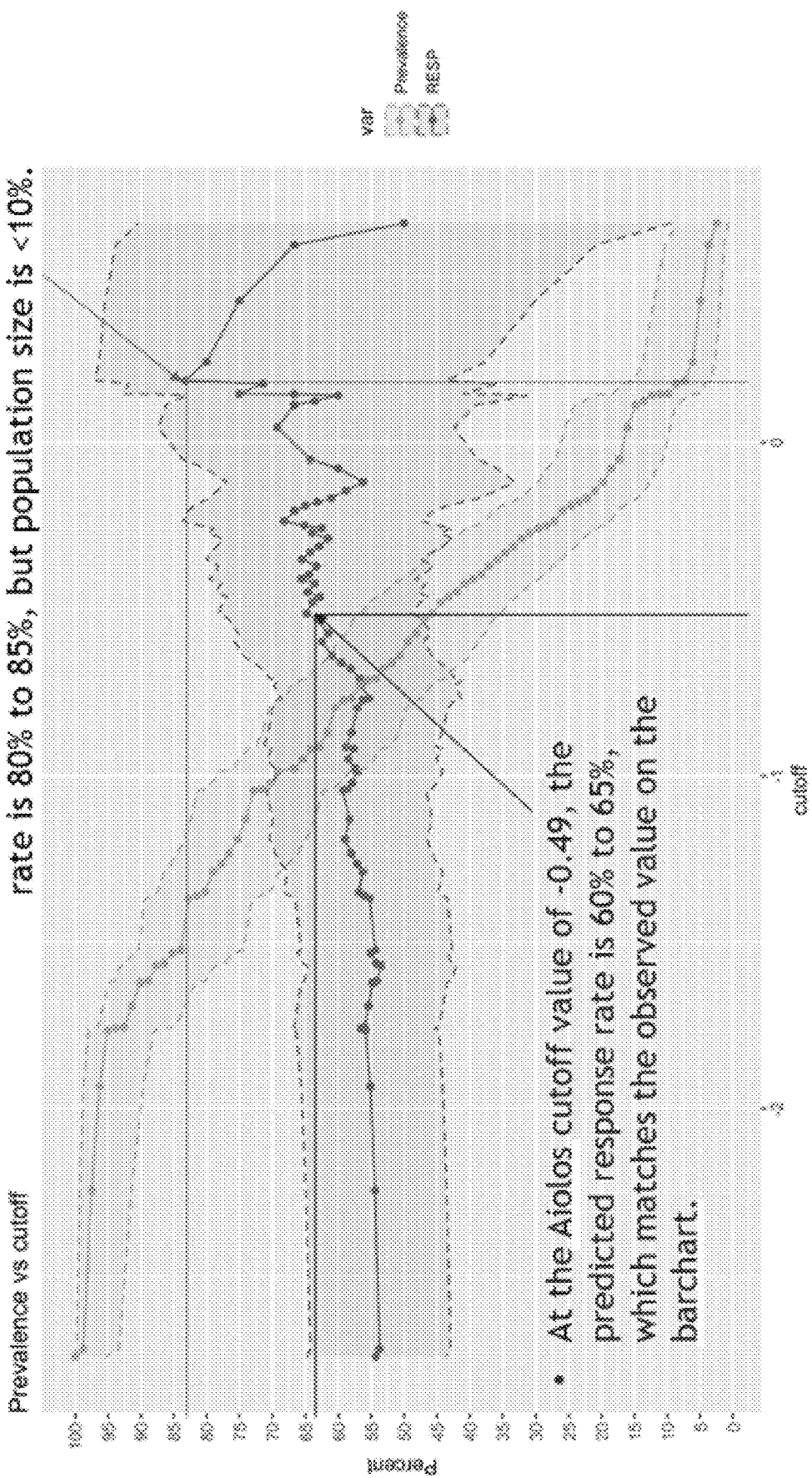
FIG. 4 shows relationship between Aiolos gene expression cutoff value, SRI-4 clinical response rate to the 0.45 mg dose of iberdomide, and prevalence in the SLE study population.

Due to the unimodal distribution of the Aiolos gene expression, the optimal cutoff for Aiolos (IKZF3) gene expression was explored using a prevalence vs. cutoff analysis as described in FIG. 4. At the pre-specified cutoff value of −0.49, the estimated response rate was 60-65%, consistent with the observed results. Using a higher Aiolos cutoff of −0.1, a higher response rate of 80 to 85% may be achieved, however the prevalence of such a subset is small, only 10% of the study population. Given the desired minimum patient subset size of no less than 35%, the pre-specified Aiolos cutoff value of −0.49 is close to optimal (FIG. 4).

Improvement of ≥50% from Baseline in CLASI Activity Score

CLASI activity score at Week 24 was analyzed. Results for improvement of ≥50% from baseline in CLASI activity score at Week 24 were observed. Results are described as follows for overall subjects at each time point and for subgroups based on baseline characteristics and on mRNA and DNA expression as follows:

Differentiation of the 0.45 mg QD iberdomide treatment group compared with the placebo treatment group is evident at Week 8 (stratified difference: 14.3%; 95% CI: −0.17, 28.07; p=0.055), Week 12 (stratified difference: 12.2%; 95% CI: −2.97, 26.66; p=0.118), Week 16 (stratified difference: 18.2%; 95% CI: 2.94, 32.43; p=0.020), and Week 20 (stratified difference: 12.3%; 95% CI: −2.91, 26.80; p=0.117) in the ITT population using NRI. At these time points, the stratified difference from placebo ranged from 0.4% to 6.9% in the 0.30 mg QD iberdomide treatment group and from −0.1% to 4.0% in the 0.15 mg QD iberdomide treatment group.

Among subjects with baseline CLASI activity score ≥8 (81 subjects overall), the stratified differences from placebo in percentage of subjects with improvement of ≥50% from baseline in CLASI activity score ranged from 9.4% (Week 16) to 32.0% (Week 4; 95% CI: 2.05, 54.92; p=0.043) in the 0.45 mg QD iberdomide treatment group, from 3.1 (Week 16) to 23.6% (Week 8) in the 0.30 mg QD iberdomide treatment group, and from 10.6% (Week 16) to 35.3% (Week 20; 95% CI: 1.06, 61.54; p=0.056) in the 0.15 mg QD iberdomide treatment group.

Subgroup analyses of CLASI improvement by mRNA and DNA expression were performed at Week 24 among subjects with baseline CLASI activity score ≥8. Results are summarized as follows for the percentage of subjects with improvement of ≥50% from baseline in CLASI activity score:

IKZF3 high: 77.8% (7/9 subjects), 33.3% (3/9 subjects), and 50.0% (2/4 subjects) for 0.45 mg, 0.30 mg, and 0.15 mg QD iberdomide, respectively, compared with 77.8% (7/9 subjects) for placebo.

Type 1 IFN module high: 61.9% (13/21 subjects), 52.4% (11/21 subjects), and 66.7% (6/9 subjects), respectively, compared with 46.7% (7/15 subjects) for placebo.

Ikaros IFN module high: 63.6% (14/22 subjects), 52.4% (11/21 subjects), 54.5% (6/11 subjects), respectively, compared with 46.7% (7/15 subjects) for placebo.

BILAG-Based Combined Lupus Assessment

Among overall subjects who had baseline BILAG 2004 1A or 2B scores, the percentage of subjects who achieved BICLA response at Week 24 was 37.3% for the 0.45 mg QD iberdomide treatment group (stratified difference from placebo: 1.0%), 33.3% for the 0.30 mg QD iberdomide treatment group (stratified difference from placebo: −3.6%), 37.1% for the 0.15 mg QD iberdomide treatment group (stratified difference from placebo: 0.3%), and 36.9% for the placebo treatment group based on NRI analysis in the ITT population. The treatment comparison with placebo (33.3%) for BICLA was larger in the subgroup of subjects with baseline IKZF3 high, but only for 0.45 mg QD iberdomide (52.0%) and 0.15 mg QD iberdomide (41.7%).

Lupus Low Disease Activity State

Among overall subjects, the percentage of subjects who achieved LLDAS response at Week 24 was 19.8% in the 0.45 mg QD iberdomide treatment group (stratified difference from placebo: 6.9%; 95% CI: −4.82, 18.56; p=0.221), 17.1% in the 0.30 mg QD iberdomide treatment group (stratified difference from placebo: −6.45, 16.49; p=0.357), 19.0% in the 0.15 mg QD iberdomide treatment group (stratified difference from placebo: 6.7%; 95% CI: −6.51, 22.32; p=0.311); and 13.3% in the placebo treatment group based on NRI analysis in the ITT population. The percentages of LLDAS responders for key mRNA and DNA subgroups were as follows:

IKZF1 high: 23.4%, 17.0%, and 14.3% for 0.45 mg, 0.30 mg, and 0.15 mg QD iberdomide, respectively, compared with 12.5% for placebo.

IKZF3 high: 27.8%, 9.4%, 14.3%, respectively, compared with 11.1% for placebo.

Type 1 IFN module high: 17.5%, 14.3%, and 24.0%, respectively, compared with 8.3% for placebo.

Ikaros IFN module high: 16.1%, 14.3%, and 20.0%, respectively, compared with 8.2% for placebo.

Drug Dose, Drug Concentration, and Relationship to Response

PK assessments were performed. Exposure-response analysis included subjects from Study SLE-002 who had both posthoc estimated iberdomide PK metric of $AUC_{ss}$ from the final population PK model and efficacy data.

Logistic regression analysis of binary response SRI(4) (nonresponder or responder) demonstrated no relationship to iberdomide $AUC_{ss}$ in subjects over the dose range of 0.15 mg to 0.45 mg QD iberdomide (p=0.927).

The effect of iberdomide exposure on SRI(4) response was further evaluated by multivariate logistic modeling. Subject characteristics of baseline oral OCS (yes as reference), baseline antimalarials (yes as reference), categorical variables of Type I IFN and IKZF3 (Aiolos) signature (low as reference) were tested in regression analysis. Subjects with IFKZ3 (Aiolos) high gene signature were associated with better response (p=0.033) (Table 2). Other subject characteristics (use of oral corticosteroids or antimalarials at baseline and having an IFN1 high gene signature) did not correlate to response with increased exposure to iberdomide.

TABLE 2

Parameter Estimates of Multivariate Logistic Model for SRI(4)

| Parameters | Estimate | SE | OR | 95% CI of OR | P-value |
|---|---|---|---|---|---|
| Intercept | 0.954 | 0.910 | — | — | 0.2946 |
| $AUC_{ss}$ on IFKZ3 (Aiolos) High Subset | 0.0969 | 0.0456 | 1.102 | (1.010, 1.209) | 0.0333 |

$AUC_{ss}$ = area under the concentration-time curve at steady state;
CI = confidence interval;
IKZF3 = Ikaros family zinc finger 3;
OR = odds ratio;
SE = standard error;
SRI = Systemic Lupus Erythematosus Responder Index.

Efficacy Conclusions

The study met its primary endpoint, which was the proportion of subjects who achieved SRI(4) response at Week 24. The percentage of subjects who achieved SRI(4) response at Week 24 was 54.3% in the 0.45 mg QD iberdomide treatment group compared with 34.9% in the placebo treatment group and the stratified difference from placebo was 19.4% (95% CI: 4.12, 33.42; p=0.011). The stratified differences from placebo for the 0.30 mg QD and 0.15 mg QD iberdomide treatment groups were 5.0% and 11.4%, respectively. The OC analysis supported a linear dose-response relationship, and other sensitivity analyses supported the findings in the main analysis. Subgroup analyses indicated that the placebo response rate for the primary efficacy endpoint was higher (48.6%) than the rate in the overall population (34.9%) in the region of South America including Mexico, which accounted for 42.7% of enrollment. Analyses of biomarker subgroups showed a greater effect of iberdomide treatment compared with overall subjects in subjects with baseline IKZF3 high, Type 1 IFN high, and Ikaros IFN high (stratified differences from placebo in the 0.45 mg QD iberdomide treatment group at Week 24 for the ITT population were 32.9%, 26.8%, and 24.3%, respectively).

Pharmacogenetics Evaluation

Clinical efficacy (SRI[4] response) was evaluated among subjects according to the single nucleotide polymorphism at the Ikaros (IKZF1) locus rs4917014 (0 copies versus 1 or 2 copies). The single nucleotide polymorphism rs4917014 is as described in Westra et al, *Nat Genet.* 45(10): 1238-1243 (2013). Specifically, SNP rs4917014 is located at chr7: 50266267 (GRCh38.p12) (Alleles: T>C/T>G). SNP rs4917014 is associated with SLE and affects expression of IKZF1. For example, the variant rs4917014*T allele strongly increased the 3'-UTR expression levels of IKZF1 and decreases expression of C1QB, two features found in SLE.

Among subjects with 0 copies of the IKZF1 rs4917014 protective minor allele (G), within the 0.45 mg QD iberdomide treated group, the SRI(4) stratified difference from placebo was 6.1% (95% CI: −17.04 to 28.38, p=0.618). Among subjects with 1 or 2 copies of the IKZF1 rs4917014 protective minor allele (G), within the 0.45 mg QD iberdomide treated group, the SRI(4) stratified difference from placebo was 21.3% (95% CI: −0.94 to 41.03, p=0.047). Therefore, clinical efficacy of 0.45 mg QD iberdomide was only observed among subjects with 1 or 2 copies of the IKZF1 rs4917014 protective minor allele (G).

OVERALL CONCLUSIONS

The findings from the 24-week Placebo-controlled Phase of this study suggest that iberdomide may be an effective treatment for active SLE, in particular among patients with high expression of IKZF3 or Type 1 IFN.

From the foregoing, it will be appreciated that, although specific embodiments have been described herein for the purpose of illustration, various modifications may be made without deviating from the spirit and scope of what is provided herein. All of the references referred to above are incorporated herein by reference in their entireties.

What is claimed is:

1. A method of determining a dose of a treatment compound for treating a subject having systemic lupus erythematosus (SLE), comprising:
   (a) measuring the gene expression level of IKZF3 in a sample from the subject; and
   (b) determining the dose of the treatment compound to be 0.45 mg or higher per day if a score calculated based on the gene expression level of IKZF3 in the sample is higher than a reference level,
   wherein the treatment compound is a compound of Formula I:

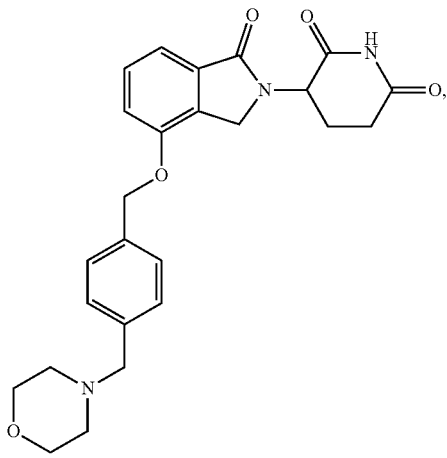

or a pharmaceutically acceptable salt, solvate, hydrate, stereoisomer, tautomer or racemic mixture thereof.

2. The method of claim 1, comprising determining the dose of the treatment compound to be about 0.45 mg per day, if the score is higher than the reference level.

3. The method of claim 1, further comprising administering the dose of 0.45 mg or higher per day of the treatment compound to the subject.

4. A method of treating a subject having systemic lupus erythematosus (SLE), comprising administering to the subject the dose of the treatment compound that is determined according to the method of claim 1.

5. The method of claim 1, wherein the gene expression level is measured by determining the protein level of IKZF3.

6. The method of claim 1, wherein the compound is (S)-3-[4 -(4-morphlin-4-ylmethylbenzyloxy)-1-oxo-1,3-dihydro-isoindo-2-yl]piperidine-2,6-dione or a pharmaceutically acceptable salt, solid form, solvate, hydrate, tautomer, stereoisomer or racemate thereof.

7. The method of claim 1, wherein the score is Log2 of the gene expression level of IKZF3 relative to a reference gene in the sample.

8. The method of claim 1, wherein the score is Log2 of the gene expression level of IKZF3 relative to an average gene expression level of two or more reference genes in the sample.

9. The method of claim 1, wherein the method comprises determining the dose of the treatment compound to be 0.45 mg or higher per day if the score is higher than −0.49.

10. The method of claim 7, wherein the reference gene is selected from a group consisting of TFRC, ACTB, GAPDH, and combinations thereof.

11. The method of claim 8, wherein the two or more reference genes are selected from a group consisting of TFRC, ACTB, GAPDH, and combinations thereof.

12. The method of claim 1, wherein the gene expression level is measured by determining the mRNA level of IKZF3.

13. The method of claim 1, wherein the gene expression level is measured by determining the cDNA level of IKZF3.

14. The method of claim 1, wherein the compound is (S)-3-[4-(4-morphlin-4 -ylmethylbenzyloxy)-1-oxo-1,3-dihydro-isoindo-2-yl]piperidine-2,6-dione.

15. The method of claim 1, wherein the compound is (S)-3-[4-(4-morphlin-4 -ylmethylbenzyloxy)-1-oxo-1,3-dihydro-isoindo-2-yl]piperidine-2,6-dione hydrochloride.

16. The method of claim 1, comprising determining the dose of the treatment compound to be about 0.5 mg per day, if the score is higher than the reference level.

17. The method of claim 1, comprising determining the dose of the treatment compound to be about 0.6 mg per day, if the score is higher than the reference level.

18. The method of claim 1, comprising determining the dose of the treatment compound to be about 0.7 mg per day, if the score is higher than the reference level.

* * * * *